(12) United States Patent
Vasquez et al.

(10) Patent No.: US 10,138,478 B2
(45) Date of Patent: Nov. 27, 2018

(54) ANTIBODY LIBRARIES

(71) Applicant: Adimab, LLC, Lebanon, NH (US)

(72) Inventors: Maximiliano Vasquez, Palo Alto, CA (US); Arvind Sivasubramanian, Santa Clara, CA (US); Michael Feldhaus, Grantham, NH (US)

(73) Assignee: Adimab, LLC, Lebanon, NH (US)

( * ) Notice: Subject to any disclaimer, the term of this patent is extended or adjusted under 35 U.S.C. 154(b) by 79 days.

(21) Appl. No.: 15/151,626

(22) Filed: May 11, 2016

(65) Prior Publication Data

US 2016/0244750 A1    Aug. 25, 2016

Related U.S. Application Data

(62) Division of application No. 13/810,570, filed as application No. PCT/US2011/044063 on Jul. 14, 2011, now Pat. No. 9,354,228.

(60) Provisional application No. 61/365,194, filed on Jul. 16, 2010.

(51) Int. Cl.
| | |
|---|---|
| C40B 50/06 | (2006.01) |
| C12N 15/10 | (2006.01) |
| C07K 16/00 | (2006.01) |
| G01N 33/543 | (2006.01) |
| C40B 40/08 | (2006.01) |
| C40B 50/02 | (2006.01) |

(52) U.S. Cl.
CPC .......... *C12N 15/1089* (2013.01); *C07K 16/00* (2013.01); *G01N 33/543* (2013.01); *C07K 2317/21* (2013.01); *C07K 2317/565* (2013.01); *C07K 2317/567* (2013.01); *C40B 40/08* (2013.01); *C40B 50/02* (2013.01); *C40B 50/06* (2013.01)

(58) Field of Classification Search
None
See application file for complete search history.

(56) References Cited

U.S. PATENT DOCUMENTS

| 4,946,778 A | 8/1990 | Ladner et al. |
| 5,118,605 A | 6/1992 | Urdea |
| 5,223,409 A | 6/1993 | Ladner et al. |
| 5,283,173 A | 2/1994 | Fields et al. |
| 5,380,833 A | 1/1995 | Urdea |
| 5,525,490 A | 6/1996 | Erickson et al. |
| 5,530,101 A | 6/1996 | Queen et al. |
| 5,565,332 A | 10/1996 | Hoogenboom et al. |
| 5,571,698 A | 11/1996 | Ladner et al. |

(Continued)

FOREIGN PATENT DOCUMENTS

| DE | 19624562 A1 | 1/1998 |
| EP | 0469897 A2 | 2/1992 |

(Continued)

OTHER PUBLICATIONS

Abbas et al., "Cellular and Molecular Immunology", 4th ed., p. 43, Figure 3-1,. W.B. Saunders Co. (2000).

(Continued)

*Primary Examiner* — Christian C Boesen
(74) *Attorney, Agent, or Firm* — Brenda Herschbach Jarrell; Robert N. Sahr; Choate, Hall & Stewart LLP

(57) ABSTRACT

The present invention overcomes the inadequacies inherent in the known methods for generating libraries of antibody-encoding polynucleotides by specifically designing the libraries with directed sequence and length diversity.

17 Claims, 15 Drawing Sheets

Specification includes a Sequence Listing.

(56) References Cited

U.S. PATENT DOCUMENTS

| | | |
|---|---|---|
| 5,618,920 A | 4/1997 | Robinson et al. |
| 5,658,727 A | 8/1997 | Barbas et al. |
| 5,688,666 A | 11/1997 | Bass et al. |
| 5,695,941 A | 12/1997 | Brent et al. |
| 5,723,323 A | 3/1998 | Kauffman et al. |
| 5,733,743 A | 3/1998 | Johnson et al. |
| 5,739,281 A | 4/1998 | Thogersen et al. |
| 5,750,373 A | 5/1998 | Garrard et al. |
| 5,767,260 A | 6/1998 | Whitlow et al. |
| 5,780,279 A | 7/1998 | Matthews et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,830,663 A | 11/1998 | Embleton et al. |
| 5,837,242 A | 11/1998 | Holliger et al. |
| 5,837,500 A | 11/1998 | Ladner et al. |
| 5,840,479 A | 11/1998 | Little et al. |
| 5,846,765 A | 12/1998 | Matthews et al. |
| 5,858,657 A | 1/1999 | Winter et al. |
| 5,858,671 A | 1/1999 | Jones |
| 5,863,765 A | 1/1999 | Berry et al. |
| 5,866,344 A | 2/1999 | Georgiou |
| 5,869,250 A | 2/1999 | Cheng et al. |
| 5,871,907 A | 2/1999 | Winter et al. |
| 5,872,215 A | 2/1999 | Osbourne et al. |
| 5,885,793 A | 3/1999 | Griffiths et al. |
| 5,888,773 A | 3/1999 | Jost et al. |
| 5,917,018 A | 6/1999 | Thogersen et al. |
| 5,922,545 A | 7/1999 | Mattheakis et al. |
| 5,928,868 A | 7/1999 | Liu et al. |
| 5,935,831 A | 8/1999 | Quax et al. |
| 5,948,620 A | 9/1999 | Hurd et al. |
| 5,955,275 A | 9/1999 | Kamb |
| 5,962,255 A | 10/1999 | Griffiths et al. |
| 5,965,368 A | 10/1999 | Vidal et al. |
| 5,969,108 A | 10/1999 | McCafferty et al. |
| 5,976,862 A | 11/1999 | Kauffman et al. |
| 5,994,515 A | 11/1999 | Hoxie |
| 5,994,519 A | 11/1999 | Osbourn et al. |
| 6,010,884 A | 1/2000 | Griffiths et al. |
| 6,017,732 A | 1/2000 | Jespers et al. |
| 6,027,910 A | 2/2000 | Klis et al. |
| 6,040,136 A | 3/2000 | Garrard et al. |
| 6,057,098 A | 5/2000 | Buechler et al. |
| 6,057,101 A | 5/2000 | Nandabalan et al. |
| 6,072,036 A | 6/2000 | Marasco et al. |
| 6,083,693 A | 7/2000 | Nandabalan et al. |
| 6,114,147 A | 9/2000 | Frenken et al. |
| 6,132,963 A | 10/2000 | Brent et al. |
| 6,140,471 A | 10/2000 | Johnson et al. |
| 6,159,705 A | 12/2000 | Trueheart et al. |
| 6,171,795 B1 | 1/2001 | Korman et al. |
| 6,172,197 B1 | 1/2001 | McCafferty et al. |
| 6,180,336 B1 | 1/2001 | Osbourn et al. |
| 6,187,535 B1 | 2/2001 | LeGrain et al. |
| 6,200,759 B1 | 3/2001 | Dove et al. |
| 6,225,447 B1 | 5/2001 | Winter et al. |
| 6,248,516 B1 | 6/2001 | Winter et al. |
| 6,291,158 B1 | 9/2001 | Winter et al. |
| 6,291,159 B1 | 9/2001 | Winter et al. |
| 6,291,160 B1 | 9/2001 | Lerner et al. |
| 6,291,161 B1 | 9/2001 | Lerner et al. |
| 6,291,650 B1 | 9/2001 | Winter et al. |
| 6,300,064 B1 | 10/2001 | Knappik et al. |
| 6,300,065 B1 | 10/2001 | Kieke et al. |
| 6,319,690 B1 | 11/2001 | Little et al. |
| 6,342,588 B1 | 1/2002 | Osbourn et al. |
| 6,358,733 B1 | 3/2002 | Motwani et al. |
| 6,406,863 B1 | 6/2002 | Zhu et al. |
| 6,410,246 B1 | 6/2002 | Zhu et al. |
| 6,410,271 B1 | 6/2002 | Zhu et al. |
| 6,420,113 B1 | 7/2002 | Buechler et al. |
| 6,423,538 B1 | 7/2002 | Wittrup et al. |
| 6,489,123 B2 | 12/2002 | Osbourn et al. |
| 6,492,107 B1 | 12/2002 | Kauffman et al. |
| 6,492,123 B1 | 12/2002 | Holliger et al. |
| 6,492,160 B1 | 12/2002 | Griffiths et al. |
| 6,521,404 B1 | 2/2003 | Griffiths et al. |
| 6,531,580 B1 | 3/2003 | Huse et al. |
| 6,544,731 B1 | 4/2003 | Griffiths et al. |
| 6,545,142 B1 | 4/2003 | Winter et al. |
| 6,555,313 B1 | 4/2003 | Griffiths et al. |
| 6,569,641 B1 | 5/2003 | Kauffman et al. |
| 6,582,915 B1 | 6/2003 | Griffiths et al. |
| 6,589,527 B1 | 7/2003 | Winter et al. |
| 6,589,741 B2 | 7/2003 | Pluckthun et al. |
| 6,593,081 B1 | 7/2003 | Griffiths et al. |
| 6,610,472 B1 | 8/2003 | Zhu et al. |
| 6,653,443 B2 | 11/2003 | Zhang et al. |
| 6,664,048 B1 | 12/2003 | Wanker et al. |
| 6,680,192 B1 | 1/2004 | Lerner et al. |
| 6,696,245 B2 | 2/2004 | Winter et al. |
| 6,696,248 B1 | 2/2004 | Knappik et al. |
| 6,696,251 B1 | 2/2004 | Wittrup et al. |
| 6,699,658 B1 | 3/2004 | Wittrup et al. |
| 6,706,484 B1 | 3/2004 | Knappik et al. |
| 6,753,136 B2 | 6/2004 | Lohning |
| 6,806,079 B1 | 10/2004 | McCafferty et al. |
| 6,828,422 B1 | 12/2004 | Achim et al. |
| 6,833,441 B2 | 12/2004 | Wang et al. |
| 6,846,634 B1 | 1/2005 | Tomlinson et al. |
| 6,916,605 B1 | 7/2005 | McCafferty et al. |
| 6,919,183 B2 | 7/2005 | Fandl et al. |
| 6,969,586 B1 | 11/2005 | Lerner et al. |
| 7,005,503 B2 | 2/2006 | Hua et al. |
| 7,063,943 B1 | 6/2006 | McCafferty et al. |
| 7,083,945 B1 | 8/2006 | Chen et al. |
| 7,094,571 B2 | 8/2006 | Harvey et al. |
| 7,138,496 B2 | 11/2006 | Hua et al. |
| 7,166,423 B1 | 1/2007 | Miltenyi et al. |
| 7,189,841 B2 | 3/2007 | Lerner et al. |
| 7,208,293 B2 | 4/2007 | Ladner et al. |
| 7,435,553 B2 | 10/2008 | Fandl et al. |
| 7,465,787 B2 | 12/2008 | Wittrup et al. |
| 7,569,357 B2 | 8/2009 | Kranz et al. |
| 2001/0037016 A1 | 11/2001 | Ning et al. |
| 2001/0041333 A1 | 11/2001 | Short et al. |
| 2002/0004215 A1 | 1/2002 | Osbourn et al. |
| 2002/0026653 A1 | 2/2002 | Allen et al. |
| 2002/0037280 A1 | 3/2002 | Lieber et al. |
| 2002/0169284 A1 | 11/2002 | Ashkenazi et al. |
| 2002/0177170 A1 | 11/2002 | Luo et al. |
| 2002/0197691 A1 | 12/2002 | Sugiyama |
| 2003/0022240 A1 | 1/2003 | Luo et al. |
| 2003/0091995 A1 | 5/2003 | Buechler et al. |
| 2003/0114659 A1 | 6/2003 | Winter et al. |
| 2003/0130496 A1 | 7/2003 | Winter et al. |
| 2003/0148372 A1 | 8/2003 | Tomlinson et al. |
| 2003/0165988 A1 | 9/2003 | Hua et al. |
| 2003/0190674 A1 | 10/2003 | Griffiths et al. |
| 2003/0228302 A1 | 12/2003 | Crea |
| 2003/0232333 A1 | 12/2003 | Ladner et al. |
| 2003/0232395 A1 | 12/2003 | Hufton |
| 2004/0038921 A1 | 2/2004 | Kreutzer et al. |
| 2004/0110941 A2 | 6/2004 | Winter et al. |
| 2004/0146976 A1 | 7/2004 | Wittrup et al. |
| 2004/0157214 A1 | 8/2004 | McCafferty et al. |
| 2004/0157215 A1 | 8/2004 | McCafferty et al. |
| 2004/0219611 A1 | 11/2004 | Racher |
| 2005/0202512 A1 | 9/2005 | Tomlinson et al. |
| 2006/0003334 A1 | 1/2006 | Achim et al. |
| 2006/0019260 A1 | 1/2006 | Lerner et al. |
| 2006/0159673 A1 | 7/2006 | Kojima |
| 2006/0166252 A1 | 7/2006 | Ladner et al. |
| 2006/0234302 A1 | 10/2006 | Hoet et al. |
| 2006/0257937 A1 | 11/2006 | Ladner |
| 2007/0031879 A1 | 2/2007 | Ley et al. |
| 2007/0099267 A1 | 5/2007 | Harvey et al. |
| 2007/0258954 A1 | 11/2007 | Iverson et al. |
| 2008/0108514 A1 | 5/2008 | Mattheus Hoogenboom |
| 2008/0153712 A1 | 6/2008 | Crea |

(56) References Cited

U.S. PATENT DOCUMENTS

| | | |
|---|---|---|
| 2008/0171059 A1 | 7/2008 | Howland et al. |
| 2009/0082213 A1 | 3/2009 | Horowitz et al. |
| 2009/0181855 A1 | 7/2009 | Vasquez et al. |
| 2010/0009866 A1 | 1/2010 | Prinz et al. |
| 2010/0056386 A1 | 3/2010 | Vasquez et al. |
| 2010/0292103 A1 | 11/2010 | Ladner |
| 2011/0009280 A1 | 1/2011 | Hufton et al. |
| 2011/0082054 A1 | 4/2011 | Ladner |
| 2011/0118147 A1 | 5/2011 | Ladner |
| 2011/0136695 A1 | 6/2011 | Crea |
| 2011/0172125 A1 | 7/2011 | Ladner |

FOREIGN PATENT DOCUMENTS

| | | |
|---|---|---|
| EP | 1438400 A1 | 7/2004 |
| JP | H0568599 A | 3/1993 |
| WO | WO-88/01649 A1 | 3/1988 |
| WO | WO-88/06630 A1 | 9/1988 |
| WO | WO-94/01567 A1 | 1/1994 |
| WO | WO-94/07922 A1 | 4/1994 |
| WO | WO-94/18330 A1 | 8/1994 |
| WO | WO-95/26400 A1 | 10/1995 |
| WO | WO-97/08320 A1 | 3/1997 |
| WO | WO-97/20923 A1 | 6/1997 |
| WO | WO-97/49809 A1 | 12/1997 |
| WO | WO-98/49198 A1 | 11/1998 |
| WO | WO-99/06834 A2 | 2/1999 |
| WO | WO-99/28502 A1 | 6/1999 |
| WO | WO-99/36569 A1 | 7/1999 |
| WO | WO-99/50461 A1 | 10/1999 |
| WO | WO-99/53049 A1 | 10/1999 |
| WO | WO-99/55367 A1 | 11/1999 |
| WO | WO-00/18905 A1 | 4/2000 |
| WO | WO-00/54057 A1 | 9/2000 |
| WO | WO-01/79229 A2 | 10/2001 |
| WO | WO-01/79481 A2 | 10/2001 |
| WO | WO-02/055718 A2 | 7/2002 |
| WO | WO-03/029456 A1 | 4/2003 |
| WO | WO-2004/065611 A1 | 8/2004 |
| WO | WO-2005/007121 A2 | 1/2005 |
| WO | WO-2005023993 A2 | 3/2005 |
| WO | WO-2005/054273 A2 | 6/2005 |
| WO | WO-2006/138700 A2 | 12/2006 |
| WO | WO-2007/056441 A2 | 5/2007 |
| WO | WO-2008/019366 A2 | 2/2008 |
| WO | WO-2008/042754 A2 | 4/2008 |
| WO | WO-2008/053275 A2 | 5/2008 |
| WO | WO-2008067547 A2 | 6/2008 |
| WO | WO-2009/036379 A2 | 3/2009 |
| WO | WO-2009/132287 A2 | 10/2009 |
| WO | WO-2010/005863 A1 | 1/2010 |
| WO | WO-2010/054007 A1 | 5/2010 |
| WO | WO-2010/105256 A1 | 9/2010 |
| WO | WO-2012/009568 A2 | 1/2012 |

OTHER PUBLICATIONS

Abbas et al., Cellular and Molecular Immunology, Fourth Edition—Section III Maturation, Activation, and Regulation of Lymphocytes, 125-133 (2000).

Adams, G.P. and Schier, R., "Generating Improved Single-Chain Fv Molecules for Tumor Targeting" Journal of Immunological Methods, 231:249-260 (1999).

Adams, G.P. and Weiner, L. M., "Monoclonal antibody therapy of cancer" Nature Biotechnology, 23(9) 1147-1157 (2005).

Akamatsu, Y. et al., "Construction of a human Ig combinatorial library from genomic V segments and synthetic CDR3 fragments" J. Immunol., 51(9):4651-4659 (1993).

Allen, J.B. et al., "Finding prospective partners in the library: the two-hybrid system and phage display find a match" TIBS, 20:(12):511-516 (1995).

Alt, F.W. and Baltimore, D., "Joining of Immunoglobulin Heavy Chain Gene Segments: Implications from a Chromosome with Evidence of Three D-JH Fusions" PNAS, 79:4118-4122 (1982).

Arden, B., "Conserved motifs in T-cell receptor CDR1 and CDR2: implications for ligand and CDS co-receptor binding" Current Opinion in Immunology, Current Biology LTD., 10(1):74-81 (1998).

Aronheim, Ami et al., "Isolation of an AP-1 Repressor by a Novel Method for Detecting Protein-Protein Interaction" Molecular and Cellular Biology, 17(6):3094-3102 (1997).

Aujame, L. et al., "High affinity human antibodies by phage display" Human Antibodies, 8(4):155-168 (1997).

Ayala, M. et al., "Variable region sequence modulates periplasmic export of a single-chain Fv antibody fragment in *Escherichia coli*" BioTechniques, 18(5):832-838, 840-2 (1995).

Bahler et al., "Clonal Salivary Gland Infiltrates Associated with Myoepithelial Sialadenitis (Sjogren's Syndrome) Begin as Nonmalignant Antigen-Selected Expansions", Blood, 91(6):1864-1872 (1998).

Bakkus et al., "Evidence that Multiple Myeloma Ig Heavy Chain VDJ Genes Contain Somatic Mutations but Show no Intraclonal Variation", Blood, 80(9):2326-2335 (1992).

Balint, R.F. and Larrick, J.W., "Antibody engineering by parsimonious mutagenesis" Gene, 137:109-118 (1993).

Barbas et al., "Molecular Profile of an Antibody Response to HIV-1 as Probed by Combinatorial Libraries", J. Mol. Bioi., 230:812-823 (1993).

Barbas, C.F. 3rd et al., "Human autoantibody recognition of DNA" Proc. Natl. Acad. Sci., 92:2529-2533 (1995).

Barbas, C.F. 3rd et al., "Semisynthetic combinatorial antibody libraries: a chemical solution to the diversity problem" Proceedings of the National Academy of Sciences of USA, 89:4457-4461 (1992).

Barbas, C.F. 3rd, et al., "Assembly of combinatorial antibody libraries on phage surfaces: The gene III site" Proc. Natl. Acad. Sci., 88:7978-7982 (1991).

Basu, M. et al., "Synthesis of compositionally unique DNA by terminal deoxynucleotidyl transferase" Biochem. Biophys. Res. Comm., 111(3):1105-1112 (1983).

Bhatia, S.K. et al., "Rolling adhesion kinematics of yeast engineered to express selectins" Biotech. Prog., 19:1033-1037 (2003).

Binz, H.K. et al., "Engineering novel binding proteins from nonimmunoglobulin domains" Nat. Biotechnol., 23(10):1257-1268 (2005).

Bird, R.E. et al., "Single-chain antigen-binding proteins" Science, 242(4877):423-426 (1988).

Boder and Wittrup, "Yeast Surface Display for Directed Evolution of Protein Expression, Affinity, and Stability" Methods in Enzymology 328:430-444 (2000).

Boder and Wittrup, "Yeast surface display system for antibody engineering" pp. 283 (1996).

Boder et al., "Yeast Surface Display of a Noncovalent MHC Class II Heterodimer Complexed With Antigenic Peptide" Biotechnology and Bioengineering 92(4):485-491 (2005).

Boder, E.T. and Jiang, W., "Engineering Antibodies for Cancer Therapy" Annu. Rev. Chem. Biomol. Eng. 2:53-75 (2011).

Boder, E.T. and Wittrup, K.D., "Optimal screening of surface-displayed polypeptide libraries" Biotechnol Prog.,14(1):55-62 (1998).

Boder, E.T. and Wittrup, K.D., "Yeast surface display for screening combinatorial polypeptide libraries" Nat Biotechnol.,15(6):553-7 (1997).

Boder, E.T. et al., "Directed evolution of antibody fragments with monovalent femtomolar antigen-binding affinity" Proc Natl Acad Sci USA, 97(20):10701-5 (2000).

Borth, N. et al., "Efficient selection of high-producing subclones during gene amplification of recombinant Chinese hamster ovary cells by flow cytometry and cell sorting" Biotechnol. and Bioengin., 71(4):266-273 (2000-2001).

Bradbury, A., "Display Technologies Expand Their Horizons" TIBTECH 17:137-138 (1999).

Bradbury, A., "Molecular Library Technologies at the Millennium", TIBTECH 18:132-133 (2000).

Bradbury, A., "Recent advances in phage display: the report of the Phage Club first meeting" Immunotechnology, 3(3):227-231 (1997).

Breitling, F. et al., "A surface expression vector for antibody screening" Gene, 104(2):147-153 (1991).

(56) References Cited

OTHER PUBLICATIONS

Brezinschek, H.P. et al., "Analysis of the human VH gene repertoire. Differential effects of selection and somatic hypermutation on human peripheral CD5(+)/IgM+ and CD5(−)/IgM+ B cells" The American Society for Clinical Investigation, Inc., 99(10):2488-2501 (1997).
Broder, Y.C. et al., "The ras recruitment system, a novel approach to the study of protein-protein interactions" Current Biology 8(20):1121-1124 (1998).
Brophy et al., "A yeast display system for engineering functional peptide-MHC complexes" Journal of Immunological Methods 272:235-246 (2003).
Burke et al., "Methods in Yeast Genetics", pp. 40-41 (2000).
Burton, D.R. et al., "A large array of human monoclonal antibodies to type 1 human immunodeficiency virus from combinatorial libraries of asymptomatic seropostive individuals" Proc. Natl. Acad. Sci., 88(22):10134-10137 (1991).
Canaán-Haden, L., "Purification and application of a single-chain Fv antibody fragment specific to hepatitis B virus surface antigen" BioTechniques, 19(4) 606-608, 610, 612 passim(1995).
Cappellaro et al., "Mating type-specific cell-cell recognition of *Saccharomyces cerevisiae*: cell wall attachment and active sites of a- and ?-agglutinin1" The EMBO Journal 13(20)4737-4744 (1994).
Carroll et al., "Absence of Ig V Region Gene Somatic Hypermutation in Advanced Burkitt's Lymphoma", J. Immunol., 143(2):692-698 (1989).
Casset, F.et al., "A peptide mimetic of an anti-CD4 monoclonal antibody by rational design" Biochemical and Biophysical Research Communications, 307(1):198-205, (2003).
Castelli, L.A. et al., "High-level secretion of correctly processed beta-lactamase from *Saccharomyces ceravisiae* using a high-copy-number secretion vector" Biomolecular Research Institute, 142(1):113-117 (1994).
Caton, A.J. and Koprowski, H., "Influenza virus hemagglutinin-specific antibodies isolated from a combinatorial expression library are closely related to the immune response of the donor" Proc. Natl. Acad. Science, USA, 87(16):6450-6454 (1990).
Cattaneo, A. and Biocca, S., "The selection of intracellular antibodies" TIBTECH, 17:115-120 (1999).
Chang, C.N. et al., "Expression of antibody Fab domains on bacteriophage surfaces. Potential use for antibody selection" J. Immunol, 147(10):3610-3614. (1991).
Chang, H.C. et al., "A general method for facilitating heterodimeric pairing between two proteins: Application to expression of alpha and beta T-cell receptor extracellular segments" Proc Natl. Acad. Sci., USA, 91:11408-11412 (1994).
Chaudhary, V.K. et al., "A rapid method of cloning functional variable-region antibody genes in *Escherichia coli* as single-chain immunotoxins" Proc. Natl. Acad. Sci., 87(3):1066-1070 (1990).
Chen, W. et al., "Characterization of germline antibody libraries from human umbilical cord blood and selection of monoclonal antibodies to viral envelope glycoproteins: Implications for mechanisms of immune evasion and design of vaccine immunogens" Biochem. Biophys. Res. Commun. 1-6 (2012).
Chiswell, David and McCaffery, John, "Phage antibodies: will new 'coliclonal' antibodies replace monoclonal antibodies?" TIBTECH, 10(3):80-84 (1992).
Cho et al., "A yeast surface display system for the discovery of ligands that trigger cell activation" journal of Immunological Methods 220:179-188 (1998).
Chothia, C. and Lesk, A.M., "Canonical structures for the hypervariable regions of immunoglobulins" J. Mol. Biol., 196(4):901-917 (1987).
Chothia, C. et al., "Conformations of immunoglobulin hypervariable regions" Nature, 342(6252):877-883 (1989).
Chothia, C. et al., "Structural repertoire of the human VH segments" J. Mol. Biol., 227(3):799-817 (1992).
Cioe, L., Cloning and Nucleotide Sequence of a Mouse Erythrocyte beta-Spectrin cDNA, Blood, 70:915-920 (1987).
Clackson, T. and Wells, J.A., "In vitro selection from protein and peptide libraries" Trends Biotechnol., 12(5):173-184 (1994).
Clackson, T. et al., "Making antibody fragments using phage display libraries" Nature, 352(6336):624-628 (1991).
Co, M.S. and Queen, C., "Humanized antibodies for therapy" Nature, 351(6326):501-502 (1991).
Colby et al., "Development of a Human Light Chain Variable Domain (VL) Intracellular Antibody Specific for the Amino Terminus of Huntingtin via Yeast Surface Display" J. Mol. Biol. 901-912 (2004).
Collins, A.M. et al., "Partitioning of rearranged Ig genes by mutation analysis demonstrates D-D fusion and V gene replacement in the expressed human repertoire" J. Immunol., 172(1):340-348 (2004).
Collins, A.M. et al., "The reported germline repertoire of human immunoglobulin kappa chain genes is relatively complete and accurate" Immunogenetics, 60(11):669-676 (2008).
Corbett, S.J. et al., "Sequence of the human immunoglobulin diversity (D) segment locus: a systematic analysis provides no evidence for the use of DIR segments, nverted D egments, "minor" D segments or D-D recombination" J. Mol. Bioi., 270:587-597 (1997).
Courtney, B.C. et al., "A phage display vector with improved stability, applicability and ease of manipulation", Gene, 165(1):139-140 (1995).
Couto, J.R. et al., "Designing human consensus antibodies with minimal positional templates", Cancer Res., (23 Suppl):5973s-5977s (1995).
Crameri, R. and Suter, M., "Display of biologically active proteins on the surface of filamentous phages: a cDNA cloning system for selection of functional gene products linked to the genetic information responsible for their production" Gene, 137(1):69-75 (1993).
Cwirla, S.E., et al., "Peptides on phage: a vast library of peptides for identifying ligands" Proc. Natl. Acad. Sci. USA, 87(16):6378-6382 (1990).
Davi et al., "High Frequency of Somatic Mutations in the VH Genes Expressed in Prolymphocytic Leukemia", Blood, 88 (10):3953-3961 (1996).
Davies, J. and Riechmann, L., "Affinity improvement of single antibody VH domains: residues in all three hypervariable regions affect antigen binding" Immunotechnology 2(3):169-179 (1996).
de Haard et al., "A Large Non-immunized Human Fab Fragment Phage Library That Permits Rapid Isolation and Kinetic Analysis of High Affinity Antibodies" Journal of Biological Chemistry, 274(26):18218-18230 (1999).
De Jaeger, G. et al., "Analysis of the interaction between single-chain variable fragments and their antigen in a reducing intracellular environment using the two-hybrid system" FEBS Lett., 467(2-3):316-320 (2000).
de Kruif, J. et al., "Selection and application of human single chain Fv antibody fragments from a semi-synthetic phage antibody display library with designed CDR3 regions" J. Mol. Biol. 248(1):97-105 (1995).
Delves, P.J. "Antibody production: essential techniques" John Wiley & Sons, New York, pp. 90-113 (1997).
DiPietro et al., "Limited number of immunoglobulin VH regions expressed in the mutant rabbit 'Alicia'", Eur. J. Immunol., 20:1401-1404 (1990).
Dranginis et al., "A Biochemical Guide to Yeast Adhesins: Glycoproteins for Social and Antisocial Occasions" Microbiology and Molecular Biology Reviews 71(2)282-294 (2007).
Esposito et al., "Phage display of a human antibody against Clostridium tetani toxin", Gene, 148:167-168 (1994).
Fan, Z. et al., "Three-dimensional structure of an Fv from a human IgM immunoglobulin" J. Mol. Biol., 228(1):188-207 (1992).
Fellouse, F.A. et al., "High-throughput Generation of Synthetic Antibodies from Highly Functional Minimalist Phage-displayed Libraries" J. Mol. Biol. 373(4):924-940 (2007).
Fellouse, F.A. et al., "Molecular Recognition by a Binary Code" J. Mol, Biol. 348(5):1153-1162 (2005).
Fellouse, F.A. et al., "Synthetic antibodies from a four-amino-acid code: a dominant role for tyrosine in antigen recognition" PNAS, 101(34):12467-12472 (2004).

(56) References Cited

OTHER PUBLICATIONS

Fields, S. and Sternglanz, R., "The two-hybrid system: an assay for protein-protein interactions" Trends Genet.,10(8):286-292 (1994).
Fields. S. and Song, O., "A novel genetic system to detect protein-protein interactions" Nature, 340(6230):245-246 (1989).
Firth, A.E. and Patrick, W.M., "GLUE-IT and PEDEL-AA: new programmes for analyzing protein diversity in randomized libraries" Nucleic Acids Res., 36:W281-W285 (2008).
Frazer, J. K., and J. D. Capra, "Immunoglobulins: Structure and Function", in Fundamental Immunology, Fourth Edition, William E. Paul, ed., Lippincot-Raven Publishers, Philadelphia, pp. 41-43 and 51-52 (1999).
Frykman, S. and Srienc, F., "Quantitating secretion rates of individual cells: design of secretion assays" Biotechnol. & Bioeng., 59(2):214-226 (1998).
Fuh, G., "Synthetic antibodies as therapeutics" Expert Opin. Biol. Ther., 7(1):73-87 (2007).
Fusco, et al., In vivo construction of cDNA libraries for use in the yeast two-hybrid system. Yeast, 15(8):715-720 (1999).
Gietz et al., "Improved method for high efficiency transformation of intact yeast cells" Nucleic Acids Res., 20(6):1425 (1992).
Gietz, R.D. and R.H. Schiestl, "Transforming Yeast with DNA" Methods in Molecular and Cellular Biology (Invited Chapter), 5:255-269 (1995).
Gilfillan, S. et al., "Efficient immune responses in mice lacking N-region diversity" Eur. J. Immunol., 25(11):3115-3122 (1995).
Griffin et al., "Blockade of T Cell Activation Using a Surface-Linked Single-Chain Antibody to CTLA-4 (CD152)" J Immunol. 64(9):4433-4442 (2000).
Griffiths, A.D. et al., "Human anti-self antibodies with high specificity from phage display libraries" EMBO J., 12(2):725-734 (1993).
Griffiths, A.D. et al., "Isolation of high affinity human antibodies directly from large synthetic repertoires," EMBO J., 13(14):3245-3260 (1994).
Hamilton and Gerngross, "Glycosylation engineering in yeast: the advent of fully humanized yeast" Current Opinion in Biotechnology 18:387-392 (2007).
Hanes, J. et al., "Picomolar affinity antibodies from a fully synthetic naive library selected and evolved by ribosome display" Nat Biotechnol. 18:(12):1287-1292 (2000).
Hasan, N. and Szybalski, W., "Control of cloned gene expression by promoter inversion in vivo: construction of improved vectors with a multiple cloning site and the Ptac promoter" Gene, 56(1):145-151 (1987).
Hawkins, R.E. and Winter, G., "Cell selection strategies for making antibodies from variable gene libraries: trapping the memory pool" Eur. J. Immunol., 22(3):867-870 (1992).
He, M. and Taussig, M.J., "Antibody-ribosome-mRNA (ARM) complexes as efficient selection particles for in vitro display and evolution of antibody combining sites" Nucleic Acids Res., 25(24):5132-5134 (1997).
Hoet, R.M. et al., "Generation of high-affinity human antibodies by combining donor-derived and synthetic complementarity-determining-region diversity" Nat. Biotechnol., 23(3):344-348 (2005).
Hoet, R.M. et al., "The importance of the light chain for the epitope specificity of human anti-U1 small nuclear RNA autoantibodies present in systemic lupus erythematosus patients" Journal of Immunology,163(6):3304-3312 (1999).
Holler et al., "In vitro evolution of a T cell recepto with high affinity for peptide / MHC" Proc. Natl. Acad. Sci. 97(10):5387-5392 (2000).
Holmes, P. and Al-Rubeai, M., "Improved cell line development by a high throughput affinity capture surface display technique to select for high secretors" J. Immunol. Methods, 230(1-2):141-147 (1999).
Hoogenboom and Chames, "Natural and designer binding sites made by phage display technology" Immunology Today 21(8):371-378 (2000).
Hoogenboom, H.R. and Winter, G., "By-passing immunisation. Human antibodies from synthetic repertoires of germline VH gene segments rearranged in vitro" J. Mol. Biol., 227(2):381-388 (1992).

Hoogenboom, H.R. et al., "Antibody phage display technology and its applications" Immunotechnology, 4(1):1-20 (1998).
Hoogenboom, H.R. et al., "Multi-subunit proteins on the surface of filamentous phage: methodologies for displaying antibody (Fab) heavy and light chains" Nucleic Acids Research, 19(15):4133-4137 (1991).
Hoogenboom, H.R., "Designing and optimizing library selection strategies for generating high-affinity antibodies" Trends Biotechnol. 15(2):62-70 (1997).
Horwitz A.H. et al., "Secretion of functional antibody and Fab fragments from yeast cells" Proc. Natl. Acad. Sci. USA, 85(22):8678-8682 (1988).
Hoshino, Y. et al., "The rational design of a synthetic polymer nanoparticle that neutralizes a toxic peptide in vivo" PNAS 109(1):33-38 (2012).
Hua, S.B. et al., "Construction of a modular yeast two-hybrid cDNA library from human EST clones for the human genome protein linkage map" Gene, 215(1):143-152 (1998).
Hua, S.B. et al., "Minimum length sequence homology required for in vivo cloning by homologous recombination in yeast" Plasmid, 38(2):91-96 (1997).
Huang et al., "A Majority of Ig H Chain eDNA of Normal Human Adult Blood Lymphocytes Resembles eDNA for Fetal Ig and Natural Autoantibodies", J. Immunol., 151:5290-5300 (1993).
Huang, D. and Shusta, E.V. et al., "Secretion and surface display of green fluorescent protein using the yeast *Saccharomyces cerevisiae*" Biotechnol. Prog., 21(2):349-357 (2005).
Hubberstey and Wildeman, "Use of interplasmid recombination to generate stable selectable markers for yeast transformation: application to studies of actin gene control" Genome 33(5):696-706 (1990).
Huse, W.D. et al., "Generation of a large combinatorial library of the immunoglobin repertoire in phage lambda" Science 246(4935):1275-1281 (1989).
Huston, J.S. et al., "Protein engineering of antibody binding sites: recovery of specific activity in an anti-digoxin single-chain Fv analogue produced in *Escherichia coli*" Proc. Natl. Acad. Sci. USA 85(16):5879-5883 (1988).
Imai and Yamamoto, "The fission yeast mating pheromone P-factor: its molecular structure, gene structure, and ability to induce gene expression and G1 arrest in the mating partner" Genes & Development 8:328-338 (1993).
International Preliminary Report of Patentability for PCT/US2011/044063, dated Jan. 31, 2013.
International Search Report and the Written Opinion of the International Searching Authority for PCT/US2011/044063, dated Feb. 14, 2012.
Ivanov, I.I. et al., "Development of the expressed Ig CDR-H3 repertoire is marked by focusing of constraints in length, amino acid use, and charge that are first established in early B cell progenitors," J. Immunol., 174(12):7773-7780 (2005).
Ivanovski et al., "Somatic Hypermutation, Clonal Diversity, and Preferential Expression of the VH 51 p1/VL kv325 Immunoglobin Gene Combination in Hepatitis C Virus-Associated Immunocytomas", Blood, 91(7):2433-2442 (1998).
Jackson, K.J., et al., "Identifying highly mutated IGHD genes in the junctions of rearranged human immunoglobulin heavy chain genes," J. Immunol. Methods, 324(1-2):26-37 (2007).
Jirholt, P. et al., "Exploiting sequence space: shuffling in vivo formed complementarity determining regions into a master framework", Gene, 215(2):471-476 (1998).
Johns M. et al., "In vivo selection of sFv from phage display libraries" J. Immunol. Methods, 239(1-2):137-151 (2000).
Juul, L. et al., "The normally expressed kappa immunoglobulin light chain gene repertoire and somatic mutations studied by single-sided specific polymerase chain reaction (PCR); frequent occurrence of features often assigned to autoimmunity" Clin. Exp. Immunol., 109(1):194-203 (1997).
Kang, A.S. et al., "Linkage of recognition and replication functions by assembling combinatorial antibody Fab libraries along phage surfaces" Proc. Natl. Acad. Sci., 88(10):4363-4666 (1991).
Karu et al., "Recombinant Antibody Technology" ILAR Journal 37(3) pp. 1-9 (1995).

(56) References Cited

OTHER PUBLICATIONS

Kieke et al., "High Affinity T Cell Receptors from Yeast Display Libraries Block T Cell Activation by Superantigens" J. Mol. Biol. 307:1305-1315 (2001).
Kieke, M.G. et al., "Isolation of anti-T cell receptor scFv mutants by yeast surface display". Protein Eng. 10(11):1303-1310 (1997).
Kieke, M.G. et al., "Selection of functional T cell receptor mutants from a yeast surface-display library" Proc. Natl. Acad. Sci. USA, 96(10):5651-5656 (1999).
Klein, R. et al., "Expressed human immunoglobulin kappa genes and their hypermutation" Eur. J. Immunol., 23(12):3248-3262 (1993).
Knappik, A. et al., "Fully synthetic human combinatorial antibody libraries (HuCAL) based on modular consensus frameworks and CDRs randomized with trinucleotides" J. Mol. Biol., 296(1):57-86 (2000).
Koiwai, O. et al., "Isolation and characterization of bovine and mouse terminal deoxynucleotidyltransferase cDNAs expressible in mammalian cells" Nucleic Acids Res., 14(14):5777-5792 (1986).
Kokubu F. et al., Complete structure and organization of immunoglobulin heavy chain constant region genes in a phylogenetically primitive vertebrate, The EMBO Journal, 7(7):1979-1988 (1988).
Kontermann, R.E. and Müller, R., "Intracellular and cell surface displayed single-chain diabodies", J. Immunol. Methods, 226(1-2):179-188 (1999).
Kostrub, C.F. et al., "Use of gap repair in fission yeast to obtain novel alleles of specific genes" Nucleic Acids Research, 26(20):4783-4784 (1998).
Kranz and Voss, "Restricted reassociation of heavy and light chains from hapten-specific monoclonal antibodies" Proc. Natl. Acad. Sci. 78(9):5807-5811 (1981).
Kretzschmar, T. and von Rüden, T., "Antibody discovery: phage display" Curr. Opin. Biotechnol., 13(6):598-602 (2002).
Lake, D.F. et al., "Generation of diverse single-chain proteins using a universal (Gly4-Ser)3 encoding oligonucleotide" BioTechniques, 19(5):700-702 (1995).
Lee, C.E., et al., "Reconsidering the human immunoglobulin heavy-chain locus: 1. An evaluation of the expressed human IGHD gene repertoire" Immunogenetics, 57(12):917-925 (2006).
Lee, C.V. et al., "High-affinity human antibodies from phage-displayed synthetic Fab libraries with a single framework scaffold" J. Mol. Biol. 340(5):1073-1093 (2004).
Lee, S.Y. et al., "Microbial cell-surface display" Trends Biotechnol., 21(1):45-52 (2003).
Leonard, B. et al., "Co-expression of antibody fab heavy and light chain genes from separate evolved compatible replicons in E. coli" J. Immunol. Methods, 317(1-2):56-63 (2006).
Lerner, R.A. et al., "Antibodies without immunization" Science,258(5086):1313-314 (1992).
Lewin, B., "Genes V", p. 99, Oxford University Press (1994).
Lieber et al., "Lymphoid V(D)J recombination: Nucleotide insertion at signal joints as well as coding joints", Proc. Natl. Acad. Sci. USA, 85:8588-8592 (1988).
Lieber, M.R., "Site-specific recombination in the immune system", FASEB J., 5:2934-2944 (1991).
Lin et al., "Display of a functional hetero-oligomeric catalytic antibody on the yeast cell surface" Appl. Microbiol. Biotechnol. 62:226-232 (2003).
Little, M. et al., "Generation of a large complex antibody library from multiple donors" J. Immunol Methods, 231(1-2):3-9 (1999).
Liu et al., "Normal Human IgD+IgM-31 Germinal Center B Cells can Express up to 80 Mutations in the Variable Region of their IgD Transcripts", Immunity, 4:603-613 (1996).
Liu, Q. et al., "Rapid construction of recombinant DNA by the univector plasmid-fusion system" Methods Enzymol. 328:530-49 (2000).
Love J.C. et al., "A microengraving method for rapid selection of single cells producing antigen-specific antibodies" Nature Biotechnol. 24(6):703-707 (2006).
Lowman, H.B. et al., "Selecting high-affinity binding proteins by monovalent phage display" Biochemistry, 30(45):10832-10838 (1991).

Ma et al., "Association of Transport-Defective Light Chains with Immunoglobulin Heavy Chain Binding Protein" Molecular Immunology 27(7):623-630 (1990).
Ma, H. et al., "Plasmid construction by homologous recombination in yeast" Gene, 58(2-3):201-216 (1987).
MacCallum, R.M. et al., "Antibody-antigen interactions: contact analysis and binding site topography" J. Mol. Biol., 262(5):732-745 (1996).
Manivasakam and Schiestl, High efficiency transformation of *Saccharomyces cerevisiae* by electroporation Nucleic Acids Research 21(18)4414-4415 (1993).
Manz, R. et al., "Analysis and sorting of live cells according to secreted molecules, relocated to a cell-surface affinity matrix" Proc. Natl. Acad. Sci. USA, 92(6):1921-1925 (1995).
Marks, J.D. et al., "By-passing Immunization. Human Antibodies from V-gene Libraries Displayed on Phage" J. Mol. Biol., 222(3):581-597 (1991).
Marks, J.D. et al., "By-passing Immunization: building high affinity human antibodies by chain shuffling" Biotechnology (NY), 10(7):779-783 (1992).
Martin, A.C., "Accessing the Kabat antibody sequence database by computer" Proteins, 25(1):130-133 (1996).
Martin, A.C.and Thornton, J.M., "Structural families in loops of homologous proteins: automatic classification, modelling and application to antibodies" J. Mol. Biol., 263(5):800-815 (1996).
Matolcsy et al., "Molecular Characterization of IgA- and/or IgG-Switched Chronic Lymphocytic Leukemia B Cells", Blood, 89(5):1732-1739 (1997).
Matsuda, F. et al., "The complete nucleotide sequence of the human immunoglobulin heavy chain variable region locus" J. Exp. Med., 188(11):2151-2162 (1998).
Mattila, P.S. et al., "Extensive allelic sequence variation in the J region of the human immunoglobulin heavy chain gene locus" Eur. J. Immunol., 9(:)2578-2582 (1995).
Mazor Y. et al., "Isolation of engineered, full-length antibodies from libraries expressed in *Escherichia coli*" Nature Biotecnol., 25(5):563-565 (2007).
McCafferty, J. et al., "Phage antibodies: filamentous phage displaying antibody variable domains" Nature, 348(6301):552-554 (1990).
McCormack, W.T., Comparison of latent and nominal rabbit Ig VHa1 allotype cDNA sequences. J. Immunol., 141(6):2063-2071 (1988).
Mcintosh et al., "Analysis of Immunoglobulin Gk Antithyroid Peroxidase Antibodies from Different Tissues in Hashimoto's Thyroiditis", J. Clin. Endocrinol. Metab., 82(11):3818-3825 (1997).
Mimran, A. et al., "GCN4-Based Expression System (pGES): Translationally Regulated Yeast Expression Vectors" BioTechniques, 28(3):552-554, 556, 558-560 (2000).
Mollova, S. et al., "Visualising the immune repertoire" BMC Systems Biology, 1(S1):P30 (2007).
Mouquet et al., "Enhanced HIV-1 neutralization by antibody heteroligation", PNAS, published on line before printing, Jan. 4, 2012, doi:10.1073/pnas.1120059109.
Mullinax, R.L. et al., "Identification of human antibody fragment clones specific for tetanus toxoid in a bacteriophage lambda immunoexpression library" Proc. Natl. Acad. Sci., 87(20):8095-8099 (1990).
Mézard, C. et al., "Recombination between similar but not identical DNA sequences during yeast transformation occurs within short stretches of identity" Cell, 70(4):659-670 (1992).
Nakamura, Y. et al., "Development of novel whole-cell immunoadsorbents by yeast surface display of the IgG-binding domain" Appl. Microbiol. Biotechnol., 57(4):500-505 (2001).
Nissim et al., "Antibody fragments from a 'single pot' phage display library as immunochemical reagents", The EMBO Journal, 13(3):692-698 (1994).
Oldenburg, K.R et al., "Recombination-mediated PCR-directed plasmid construction in vivo in yeast" Nucleic Acids Res, 25(2):451-452 (1997).
Onda, T. et al., "A phage display system for detection of T cell receptor-antigen interactions" Mol Immunol., 32(17-18):1387-1397 (1995).

(56) References Cited

OTHER PUBLICATIONS

Orr et al., "Rapid Method for Measuring ScFv Thermal Stability by Yeast Surface Display" Biotechnol. Prog. 19:631-638 (2003).
Panka, D.J. et al., "Variable region framework differences result in decreased or increased affinity of variant anti-digoxin antibodies" Proc. Natl. Acad. Sci. USA, 85(9):3080-3084 (1988).
Parthasarathy, R. et al., "An immobilized biotin ligase: surface display of *Escherichia coli* BirA on *Saccharomyces cerevisiae*" Biotechnol. Prog., 21(6):1627-1631 (2005).
Pasqualini, R. and Ruoslahti, E., "Organ targeting in vivo using phage display peptide libraries" Nature, 380(6572):364-366 (1996).
Patel et al., "Parallel selection of antibody libraries on phage and yeast surfaces via a cross-species display" Protein Engineering, Design & Selection, pp. 1-9 (2011).
Patrick, W.M. et al., "User-friendly algorithms for estimating completeness and diversity in randomized protein-encoding libraries" Protein Engineering, 16(6):451-457 (2003).
Pearson, B.M. et al., "Construction of PCR-ligated long flanking homology cassettes for use in the functional analysis of six unknown open reading frames from the left and right arms of *Saccharomyces cerevisiae* chromosome XV" Yeast, 14(4):391-399 (1998).
Pepper et al., "A Decade of Yeast Surface Display Technology: Where Are We Now?" Combinatorial Chemistry & High Throughput Screening 11:127-134 (2008).
Persson, M.A. et al., "Generation of diverse high-affinity human monoclonal antibodies by repertoire cloning" Proc. Natl. Acad. Sci. USA, 88(6):2432-2436 (1991).
Philibert, P. et al., "A focused antibody library for selected scFvs expressed at high levels in the cytoplasm" BMC Biotechnol., 7:81 (2007).
Pini, A. et al., "Design and use of a phage display library. Human antibodies with subnanomolar affinity against a marker of angiogenesis eluted from a two-dimensional gel" Journal of Biological Chemistry, 273(34):21769-21776 (1998).
Pluckthun, A., "Antibody engineering: Advances from the use of *Escherichia coli* expression systems" Biotechnology (NY) 9(6):545-551 (1991).
Pogue and Goodnow, "Gene Dose-dependent Maturation and Receptor Editing of B Cells Expressing Immumoglobulin (Ig)G1 or IgM/IgG1 Tail Antigen Receptors" J. Exp. Med 191(6) 1031-1043 (2000).
Powell, Richard and McLane, Kathryn Evans, "Construction, assembly and selection of combinatorial antibody libraries." Genetic Engineering with PCR (Horton and Tait, Eds. 1998), vol. 5 of The Current Innovations in Molecular Biol series, Horizon Scientific Press, pp. 155-172.
Prabakaran, P. et al., "Expressed antibody repertoires in human cord blood cells: 454 sequencing and IMGT/High V-QUEST analysis of germline gene usage, junctional diversity, and somatic mutations" Immunogenetics (2011), pp. 1-14.
Prabakaran, P. et al., Supplemental "Expressed antibody repertoires in human cord blood cells: 454 sequencing and IMGT/High V-QUEST analysis of germline gene usage, junctional diversity, and somatic mutations" Immunogenetics (2011), pp. 1-6.
Proba, K. et al., "Antibody scFv fragments without disulfide bonds made by molecular evolution". J Mol Biol. 275(2):245-253 (1998).
Pörtner-Taliana, A. et al., "In vivo selection of single-chain antibodies using a yeast two-hybrid system", J. Immunol. Methods, 238(1-2):161-172 (2000).
Rader, C and Barbas, C.F. 3rd, "Phage display of combinatorial antibody libraries" Curr. Opin. Biotechnol., 8(4):503-508 (1997).
Rader, C. et al., "A phage display approach for rapid antibody humanization: designed combinatorial V gene libraries" Proc. Natl. Acad. Sci. USA, 95(15):8910-8915 (1998).
Rajan, S. and Sidhu, S., "Simplified Synthetic Antibody Libraries" Methods in Enzymology 202 3-23 (2012).
Rakestraw, J.A. and Wittrup, K.D., "Dissertation Abstracts International", 68(1B):43, abstract only (2006).
Rakestraw, J.A. et al., "A Flow Cytometric Assay for Screening Improved Heterologous Protein Secretion in Yeast." Biotechnol. Prog., 22(4):1200-1208 (2006).
Rauchenberger, R. et al., "Human combinatorial Fab library yielding specific and functional antibodies against the human fibroblast growth factor receptor 3" J. Biol. Chem., 278(40):38194-38205 (2003).
Raymond, C.K. et al., "General method for plasmid construction using homologous recombination" BioTechniques, 26(1):134-138, 140-141 (1999).
Retter, I. et al., "VBASE2, an integrative V gene database" Nucleic Acids Res., 33:D671-D674 (2005).
Rhoden, J.J. and Wittrup, K.D., "Dose Dependence of Intratumoral Perivascular Distribution of Monoclonal Antibodies" Journal of Pharmaceutical Sciences 101(2): 860-867 (2012).
Roitt, I. et al., "Immunoglobulins: A Family of Proteins", in Immunology, Sixth Edition, Mosby, Harcourt Publishers Limited, London, pp. 67-70 and 80 (2001).
Rothe, C. et al., The Human Combinatorial Antibody Library HuCAL Gold Combines Diversification of All Six CDRs According to the Natural Immune System with a Novel Display Method for Efficient Selection of High-Affinity Antibodies, J. Mol. Biol., 376:1182-1200 (2008).
Rudikoff, S. et al., "Single amino acid substitution altering antigen-binding specificity" Proc. Natl. Acad. Sci. USA, 79(6):1979-1983 (1982).
Ruiz, M. et al., "The human immunoglobulin heavy diversity (IGHD) and joining (IGHJ) segments." Exp. Clin. lrnrnunogenet, 16(3):173-184 (1999).
Ryu, D.D. and Nam, D.H., "Recent progress in biomolecular engineering" Biotechnol Prog, 16(1):2-16 (2000).
Saada, R. et al., "Models for antigen receptor gene rearrangement: CDR3 length" Immunol. Cell Biol., 85(4):323-332 (2007).
Sahota et al., "Ig VH Gene Mutational Patterns Indicate Different Tumor Cell Status in Human Myeloma and Monoclonal Gammopathy of Undetermined Significance", Blood, 87(2):746-755 (1996).
Sblattero, D. and Bradbury, A., "A definitive set of oligonucleotide primers for amplifying human V regions" Immunotechnology, 3(4):271-278 (1998).
Sblattero, D. and Bradbury, A., "Exploiting recombination in single bacteria to make large phage antibody libraries" Nat. Biotechnol., 18(1):75-80 (2000).
Scaviner, D. et al., "Protein displays of the human immunoglobulin heavy, kappa and lambda variable and joining regions." Exp. Clin. Immunogenet., 16(4):234-240 (1999).
Schable, K.F. and Zachau, H.G., "The variable genes of the human immunoglobulin kappa locus" Biol. Chem. Hoppe Seyler, 374(11):1001-1022 (1993).
Schoonbroodt, S. et al., "Oligonucleotide-assisted cleavage and ligation: a novel directional DNA cloning technology to capture cDNAs. Application in the construction of a human immune antibody phage-display library" Nucleic Acids Research, 33(9):e81:2-14 (2005).
Schreuder et al., "Immobilizing proteins on the surface of yeast cells" Trends Biotechnol. 14(4)115-120 (1996).
Schreuder et al., "Targeting of a Heterologous Protein to the Cell Wall of *Saccharamyces cerevisiae*" Yeast 9:399-409 (1993).
Schwager, J. et al., Amino acid sequence of heavy chain from Xenopus levis IgM deduced from cDNA sequence: Implications for evolution of immunoglobulin domains, Proc. Natl. Acad. Sci. USA, 85:2245-2249 (1988).
Seed, B., "Developments in expression cloning." Current Opinion in Biotechnology, 6(5):567-573 (1995).
Sharifmoghadam, et al., "The fission yeast Map4 protein is a novel adhesin required for mating" FEBS Letters 580:4457-4462 (2006).
Sheets, M.D. et al., "Efficient construction of a large nonimmune phage antibody library: The production of high-affinity human single-chain antibodies to protein antigens." Proc. Natl. Acad. Sci. USA, 95(11):6157-6162 (1998).

(56) References Cited

OTHER PUBLICATIONS

Shen et al., "Delineation of Functional Regions within the Subunits of the *Saccharomyces cerevisiae* Cell Adhesion Molecule a-Agglutinin" The Journal of Biological Chemistry 276(19):15768-15775 (2001).
Shimoda et al., "Natural polyreactive immunoglobulin A antibodies produced in mouse Peyer's patches", Immunology, 97:9-17 (1999).
Short, M.K. et al., "Contribution of antibody heavy chain CDR1 to digoxin binding analyzed by random mutagenesis of phage-displayed Fab 26-10" J. Biol. Chem., 270(48):28541-28550 (1995).
Shusta, E.V. et al., "Directed evolution of a stable scaffold forT-cell receptor engineering" Nat. Biotechnol.,18(7):754-759 (2000).
Shusta, E.V. et al., "Yeast Polypeptide Fusion Surface Display Levels Predict Thermal Stability and Soluble Secretion Efficiency" J. Mol. Biol. 292 949-956 (1999).
Sidhu, S.S, et al., "Phage-displayed antibody libraries of synthetic heavy chain complementarity determining regions" J. Mol. Biol. 338(2):229-310 (2004).
Skerra, A., "Alternative non-antibody scaffolds for molecular recognition" Current Opin. Biotechnol. 18(4):295-304 (2007).
Smith, G., "Homologous Recombination Near and Far from DNA Breaks: Alternative Roles and Contrasting Views" Annu Rev Genet 35:243-274 (2001).
Smith, G.P. and Petrenko, V.A., "Phage Display" Chem. Rev., 97(2):391-410 (1997).
Soderlind, E. et al., "Domain libraries: synthetic diversity for de novo design of antibody V-regions" Gene, 160(2): 269-272 (1995).
Soderlind, E. et al., "The immune diversity in a test tube—non-immunised antibody libraries and functional variability in defined protein scaffolds" Combinatorial Chemistry & High Throughput Screening, 4(5):409-416 (2001).
Souriau and Hudson, "Recombinant antibodies for cancer diagnosis and therapy" Expert Opin. Biol. Ther. 1(5):845-855 (2001).
Souto-Carneiro, M.M. et al., "Characterization of the Human Ig Heavy Chain Antigen Binding Complementarity Determining Region 3 Using a Newly Developed Software Algorithm, JOINSOLVER," J. Immunol., 172(11):6790-6802 (2004).
Starwalt et al., "Directed evolution of a single-chain class II MHC product by yeast display" Protein Engineering 16(2):147-156 (2003).
Stewart, A.K. et al., "High-frequency representation of a single VH gene in the expressed human B cell repertoire" J. Exp. Med., 177(2):409-418 (1993).
Stohl, W. and Hilbert, D.M., "The discovery and development of belimumab: the anti-BLyS-lupus connection" Nature Biology 30(1):69-77 (2012).
Struhl et al., "High-frequency transformation of yeast: Autonomous replication of hybrid DNA molecules" Proc. Natl. Acad. Sci. 76(3):1035-1039 (1979).
Suzuki, M. et al., "Light chain determines the binding property of human anti-dsDNA IgG autoantibodies" Biochem. Biophys. Res. Commun., 271(1):240-243 (2000).
Swers et al., "Integrated Mimicry of B Cell Antibody Mutagenesis Using Yeast Homologous Recombination" Mol. Biotechnol. 46:57-69 (2011).
Swers, J.S. et al., "Shuffled antibody libraries created by in vivo homologous recombination and yeast surface display" Nuc. Acids. Res. 32(3), e36, 1-8 (2004).
Tavladoraki, P. et al., "Transgenic plants expressing a functional single-chain Fv antibody are specifically protected from virus attack" Nature, 366(6454):469-472 (1993).
Terskikh, A.V. et al., "Peptabody: A new type of high avidity binding protein" Proc. Natl. Acad., 94(5):1663-1668 (1997).
Tomlinson, I.M. et al., "The repertoire of human germline VH sequences reveals about fifty groups of VH segments with different hypervariable loops" Journal of Molecular Biology, 227(3):776-798 (1992).
Tomlinson, I.M. et al., "The structural repertoire of the human V kappa domain" EMBO J., 14(18):4628-4638 (1995).
Tsurushita, N. et al., "Phage display vectors for in vivo recombination of immunoglobulin heavy and light chain genes to make large combinatorial libraries" Gene, 172(1):59-63 (1996).
Ueda and Tanaka, "Cell Surface Engineering of Yeast: Construction of Arming Yeast with Biocatalyst" Journal of Bioscience and Bioengineering 90(2):125:136 (2000).
Ueda, M. and Tanaka, A., "Genetic immobilization of proteins on the yeast cell surface" Biotechnology Advances, 18(2):121-140 (2000).
van den Beucken et al., "Affinity maturation of Fab antibody fragments by fluorescent-activated cell sorting of yeast-displayed libraries" FEBS Letters 546:288-294 (2003).
VanAntwerp and Wittrup, "Fine Affinity Discrimination by Yeast Surface Display and Flow Cytometry" Biotechnol. Prog. 16:31-37 (2000).
Vander Vaart, J.M. et al., "Comparison of cell wall proteins of *Saccharomyces cerevisiae* as anchors for cell surface expression of heterologous proteins" Appl. Environ. Microbiol., 63(2):615-620 (1997).
Vaswani, S.K. and Hamilton, R.G., "Humanized antibodies as potential therapeutic drugs" Ann. Allergy Athma Immunol., 81(2):105-115 (1998).
Vendel, M.C. et al., "Secretion from bacterial versus mammalian cells yields a recombinant scFv with variable folding properties" Arch. Biochem. Biophys. 1-6 (2012).
Visintin. M. et al., "Selection of antibodies for intracellular function using a two-hybrid in vivo system.", Proc. Natl. Acad. Sci. USA 96(21):11723-11728 (1999).
Volpe, J.M. and Kepler, T.B., "Genetic correlates of autoreactivity and autoreactive potential in human Ig heavy chains" Immunome Res., 5:1 (2009).
Volpe, J.M. et al., "SoDA: Implementation of a 3D Alignment Algorithm for Inference of Antigen Receptor Recombinations," Bioinforrnatics, 22(4):438-444 (2006).
Vugmeyster, Y. et al., "Complex Pharmacokinetics of a Humanized Antibody Against Human Amyloid Beta Peptide, Anti-Abeta Ab2, in Nonclinical Species" Pharm Res, 28:1696-1706 (2011).
Walhout, A.J. et al., "GATEWAY recombinational cloning: application to the cloning of large numbers of open reading frames or ORFeomes" Methods in Enzymology, 328:575-92 (2000).
Wang, Y. et al., "Many human immunoglobulin heavy-chain IGHV gene polymorphisms have been reported in error" Immunol. Cell. Biol., 86(2):111-115 (epub 2007-2008).
Weaver-Feldhaus, J.M. et al., "Yeast mating for combinatorial Fab library generation and surface display" FEBS Lett., 564(1-2):24-34 (2004).
Welschof et al., "Amino acid sequence based PCR primers for amplification of rearranged human heavy and light chain immunoglobulin variable region genes", J. Immunol. Meth., 179:203-214 (1995).
Wen et al., "T cells recognize the VH complementarity-determining region 3 of the idiotypic protein of B cell non-Hodgkin's lymphoma", Eur. J. Immunol., 27:1043-1047 (1997).
Wentz, A.E. and Shusta, E.V., "A novel high-throughput screen reveals yeast genes that increase secretion of heterologous proteins" Appl. Environ. Microbiol., 73(4):1189-1198 (2007).
Winkler et al., "Analysis of immunoglobulin variable region genes from human IgG anti-DNA hybridomas", Eur. J. Immunol., 22:1719-1728 (1992).
Winter G. and Milstein C., "Man-made antibodies" Nature, 349(6307):293-299 (1991).
Winter, Greg, "Synthetic human antibodies and a strategy for protein engineering", FEBS Letters, 430:92-94 (1998).
Wood et al., "The synthesis and in vivo assembly of functional antibodies in yeast" Nature 314:(6010)446-449 (1985).
Woods and Gietz, "High-Efficiency Transformation of Plasmid DNA into Yeast", Methods in Molecular Biology, 177:85-97 (2001).
Wu, H. et al., "Humanization of a murine monoclonal antibody by simultaneous optimization of framework and CDR residues" J. Mol. Biol., 294(1):151-162 (1999).
Wörn, A. and Plückthun, A., "An intrinsically stable antibody scFv fragment can tolerate the loss of both disulfide bonds and fold correctly." FEBS Lett., 427(3):357-361 (1998).

(56) References Cited

OTHER PUBLICATIONS

Xu, J.L. and Davis, M.M., "Diversity in the CDR3 region of V(H) is sufficient for most antibody specificities" Immunity, 13(1):37-45 (2000).
Yang, W.P. et al., "CDR walking mutagenesis for the affinity maturation of a potent human anti-HIV-1 antibody into the picomolar range" J. Molecular Biology, 254(3):392- 403 (1995).
Yeung and Wittrup, "Quantitative Screening of Yeast Surface-Displayed Polypeptide Libraries by Magnetic Bead Capture" Biotechnol. Prog. 18(2):212-220 (2002).
Zemlin, M. et al., "Expressed murine and human CDR-H3 intervals of equal length exhibit distinct repertoires that differ in their amino acid composition and predicted range of structures" J. Mol. Biol. 334(4):733-749 (2003).
Zeng et al., "CD146, an epithelial-mesenchymal transition inducer, is associated with triple-negative breast cancer", published on line before print Dec. 30, 2011, doi:1010.1073/pnas.1111053108.
Zucconi, A. et al., "Domain repertoires as a tool to derive protein recognition rules" FEBS Letters, 480(1):49-54 (2000).
Flyak, A. et al., In silico analysis of the structure of variable domains of mouse single-chain antibodies specific to the human recombinant interferon beta1b, Cytol Genet, 43(1):54-60 (2009).
Roman, T. et al., Evolution of specific antigen recognition: size reduction and restricted length distribution of the CDRH3 regions in the rainbow trout, Eur J Immunol, 25(1):269-73 (1995).
Foote, J. and Winter, G., Antibody Framework Residues Affecting the Conformation of the Hypervariable Loops, J. Mol. Biol., 224:487-499 (1992).

FIGURE 4

| IGHJ3-02 | | ATGCTTTGATATCT...TCTTCAG |
|---|---|---|
| IGHJ3-02-1 | Mutate 5' doublet | NNTGCTTTGATATCT...TCTTCAG |
| IGHJ3-02-2 | Delete 5' codon | GCTTTGATATCT...TCTTCAG |
| IGHJ3-02-3 | Mutate 5' doublet | NNTTTTGATATCT...TCTTCAG |
| IGHJ3-02-4 | Delete 5' codon | TTTGATATCT...TCTTCAG |
| IGHJ3-02-5 | Mutate 5' doublet | NNGATATCT...TCTTCAG |

| IGHJ1-01 | | GCTGAATACTTCCAG...TCCTCAG |
|---|---|---|
| IGHJ1-01-1 | Mutate 5' doublet | NNTGAATACTTCCAG...TCCTCAG |
| IGHJ1-01-2 | Delete 5' codon | GAATACTTCCAG...TCCTCAG |
| IGHJ1-01-3 | Mutate 5' doublet | NNATACTTCCAG...TCCTCAG |
| IGHJ1-01-4 | Delete 5' codon | TACTTCCAG...TCCTCAG |
| IGHJ1-01-5 | Mutate 5' doublet | NNCTTCCAG...TCCTCAG |

| IGHJ2-01 | | CTACTGGTACTTCGA...TCCTCAG |
|---|---|---|
| IGHJ2-01-1 | Mutate 5' doublet | NNACTGGTACTTCGA...TCCTCAG |
| IGHJ2-01-2 | Delete 5' codon | CTGGTACTTCGA...TCCTCAG |
| IGHJ2-01-3 | Mutate 5' doublet | NNGGTACTTCGA...TCCTCAG |
| IGHJ2-01-4 | Delete 5' codon | GTACTTCGA...TCCTCAG |
| IGHJ2-01-5 | Mutate 5' doublet | NNACTTCGA...TCCTCAG |

FIGURE 8

Based on a set of CDRH3 sequences derived from 55 clinically relevant human mAbs

| Amino acid mismatches in Kabat-H3 region | LUA-141 | Exemplary Library Design 3 (EDLD-3) | Extended Diversity Library Design (EDLD) |
|---|---|---|---|
| 0 | 4 | 7 | 25 |
| 1 | 16 | 27 | 15 |
| 2 | 19 | 5 | 9 |
| 3-or-more | 16 | 16 | 6 |
| Total | 55 | 55 | 55 |

ANTIBODY LIBRARIES

CROSS REFERENCE TO RELATED APPLICATIONS

This application is a divisional of U.S. application Ser. No. 13/810,570, filed on Apr. 1, 2013, which is a national phase entry under 35 U.S.C. § 371 of International Application No. PCT/US2011/044063, filed on Jul. 14, 2011, which claims priority to U.S. Provisional Application No. 61/365,194, filed on Jul. 16, 2010. The disclosure of each of U.S. application Ser. No. 13/810,570 and U.S. Provisional Application No. 61/365,194 are hereby incorporated herein by reference in their entirety.

SEQUENCE LISTING

In accordance with 37 CFR 1.52(e)(5), a Sequence Listing in the form of a text file (entitled "Sequence Listing.txt" created on May 10, 2016 and 2,451 kilo bytes in size) is incorporated by reference in its entirety.

BACKGROUND

Antibodies have profound relevance as research tools and in diagnostic and therapeutic applications. However, the identification of useful antibodies is difficult and once identified, antibodies often require considerable redesign or "humanization" before they are suitable for therapeutic applications in humans.

Many methods for identifying antibodies involve display of libraries of antibodies derived by amplification of nucleic acids from B cells or tissues. Some of these methods have utilized synthetic libraries. However, many of these approaches have limitations. For example, most human antibody libraries known in the art contain only the antibody sequence diversity that can be experimentally captured or cloned from a biological source (e.g., B cells). Accordingly, such libraries may over-represent some sequences, while completely lacking or under-representing other sequences, particularly those binding human antigens. Most synthetic libraries known in the art have other limitations, such as the occurrence of unnatural (i.e., non-human) amino acid sequence motifs that have the potential to be immunogenic.

Accordingly, a need exists for diverse antibody libraries that contain candidate antibodies that are non-immunogenic (i.e., are human) and have desired properties (e.g., the ability to recognize a broad variety of antigens). However, obtaining such libraries requires balancing the competing objectives of generating diverse libraries while still maintaining the human character of the sequences within the library. The current invention provides antibody libraries that have these and other desirable features, and methods of making and using such libraries.

SUMMARY

The invention provides, among other things, improvements in the design and production of synthetic libraries that mimic the diversity of the natural human repertoire of CDRH3, CDRL3, heavy chain, light chain, and/or full-length (intact) antibody sequences. In some embodiments the invention defines and provides methods of generating theoretical segment pools of TN1, DH, N2, and H3-JH segments to consider for inclusion in a physical manifestation of a library (e.g., polynucleotide or polypeptide) comprising or encoding CDRH3 sequences (e.g., an antibody library). In certain embodiments the invention defines and provides methods of matching the individual members of these theoretical segment pools to a reference set of CDRH3 sequences, to determine the frequency of occurrence (or segment usage weight) of each of the segments in the theoretical segment pool in the reference set. While any set of CDRH3 sequences may be used as a reference set, the invention also defines and provides methods of generating particular reference sets or subsets of interest. For example, among other things, the present invention provides methods for filtering an original reference set to obtain a provided reference set with a preimmune character. Also provided are methods to define and/or identify segments that occur within the CDRH3 sequences in the reference set but not in the theoretical segment pool. Such segments can be added to a theoretical segment pool, for example in order to be considered for inclusion in a physical library. Although the frequency of occurrence of a particular segment in a reference set is useful to select segments for inclusion in a physical library, the invention also provides a number of physicochemical and biological properties that can be used (alone or together with any other criterion or criteria) to select segments for inclusion in a physical library.

In some embodiments the invention provides libraries that differ from certain other libraries known in the art in that they are not sitewise-stochastic in composition or sequence, and are therefore intrinsically less random than these certain other libraries of the art (see e.g., Example 14 of US Pub. No. 2009/0181855, incorporated by reference in its entirety, for a discussion of information content and randomness). In some embodiments, degenerate oligonucleotides may be used to further increase the diversity of the members of a library while further improving matching with a reference set of sequences (e.g., CDRH3, CDRL3, heavy chain, light chain, and/or full-length (intact) antibody sequences).

The invention also provides libraries whose members have sequences that are related to one another in that they would be selected for inclusion in a physical library by performing the analyses described herein, for example by generating a CDRH3 reference set as in Example 3; generating theoretical segment pools as in Examples 5-7; matching the members of a theoretical segment pool to the reference set as in Examples 4 and 8; and selecting members of the theoretical segment pool for inclusion in a physical library as in Examples 8-9. Also provided are methods of further increasing diversity in certain sequences by utilizing degenerate oligonucleotides as in Examples 12-16.

In some embodiments, the present invention provides polynucleotide and polypeptide libraries comprising CDRH3, CDRL3, heavy chain, light chain, and/or full-length (intact) antibody sequences, and methods of making and using such libraries.

In some embodiments, the invention provides libraries comprising, consisting essentially of, or consisting of any of the libraries or theoretical segment pools described herein.

In some embodiments, the present invention recognizes that by mimicking the in vivo activity of the enzyme TdT computationally, theoretical segment pools can be generated and subsequently matched to large reference datasets of CDR sequences to choose, for inclusion in a library, those theoretical segments that best recapitulate the CDR sequences in the reference data sets.

In certain embodiments, the invention provides libraries of polynucleotides comprising at least about $10^4$ polynucleotides encoding CDRH3 polypeptides with the structure: [TN1]-[DH]-[N2]-[H3-JH], wherein: TN1 is a polypeptide corresponding to any of the TN1 polypeptides of Tables 9-10 and 18-26, or a polypeptide produced by translation of any of the TN1 polynucleotides of Tables 25-26; DH is a polypeptide corresponding to any of the DH polypeptides of Tables 9, 11, 17-25 and 28, or a polypeptide produced by translation of any of the DH-encoding polynucleotides of Tables 16, 25 and 27; N2 is a polypeptide corresponding to any of the N2 polypeptides of Tables 9, 12, 18-25 and 30, or a polypeptide produced by translation of any of the N2-encoding polynucleotides of Tables 25 and 29; and H3-JH is a polypeptide corresponding to any of the H3-JH polypeptides of Tables 9, 13, 15, 18-25 and 32, or a polypeptide produced by translation of any of the H3-JH-encoding polynucleotides of Tables 14, 25 and 31.

In some embodiments, the invention provides libraries wherein at least about 1%, 5%, or 10% of the sequences in the library have the structure provided above, or that of any of the libraries provided herein.

In certain embodiments, the invention provides libraries comprising polynucleotides encoding CDRH3 polypeptides produced by the sets of TN1, DH, N2, and H3-JH polypeptides provided in any one of Tables 23-25.

In some embodiments, the invention provides libraries comprising polynucleotides encoding CDRH3 polypeptides produced by the set of TN1 polypeptides provided in Table 26, the set of DH polypeptides provided in Table 28, the set of N2 polypeptides provided in Table 30 and the set of H3-JH polypeptides provided in Table 32.

In certain embodiments, the invention provides libraries whose members show (or encode polypeptides that show) at least a certain percent identity with the polypeptides described above, for example, a library comprising at least about $10^4$ polynucleotides encoding CDRH3 polypeptides with the structure: [TN1]-[DH]-[N2]-[H3-JH], wherein: TN1 is a polypeptide at least about 80%, 90%, or 95% identical to any of the TN1 polypeptides of Tables 9-10 and 18-26, or a polypeptide at least about 80%, 90%, or 95% identical to a polypeptide produced by translation of any of the TN1 polynucleotides of Tables 25-26; DH is a polypeptide at least about 80%, 90%, or 95% identical to any of the DH polypeptides of Tables 9, 11, 17-25 and 28, or a polypeptide at least about 80%, 90%, or 95% identical to a polypeptide produced by translation of any of the DH-encoding polynucleotides of Tables 16, 25 and 27; N2 is a polypeptide at least about 80%, 90%, or 95% identical to any of the N2 polypeptides of Tables 9, 12, 18-25 and 30, or a polypeptide at least about 80%, 90%, or 95% identical to a polypeptide produced by translation of any of the N2-encoding polynucleotides of Tables 25 and 29; and H3-JH is a polypeptide at least about 80%, 90%, or 95% identical to any of the H3-JH polypeptides of Tables 9, 13, 15, 18-25 and 32, or a polypeptide at least about 80%, 90%, or 95% identical to a polypeptide produced by translation of any of the H3-JH-encoding polynucleotides of Tables 14, 25 and 31.

In some embodiments, the invention provides libraries comprising polynucleotides encoding light chain variable regions, wherein the light chain variable regions are selected from the group consisting of: (a) a VK1-05 sequence varied at one or more of positions 4, 49, and 46; (b) a VK1-12 sequence varied at one or more of positions 4, 49, 46, and 66; (c) a VK1-33 sequence varied at one or more of positions 4, 49, and 66; (d) a VK1-39 sequence varied at one or more of positions 4, 49, and 46; (e) a VK2-28 sequence varied at one or more of positions 2, 4, 46, and 49; (f) a VK3-11 sequence varied at one or more of positions 2, 4, 36, and 49; (g) a VK3-15 sequence varied at one or more of positions 2, 4, 48, and 49; (h) a VK3-20 sequence varied at one or more of positions 2, 4, 48, and 49; and/or (i) a VK4-1 sequence varied at one or more of positions 4, 46, 49, and 66.

In certain embodiments, the invention provides libraries comprising polynucleotides encoding light chain variable regions that comprise polypeptide sequences at least about 80%, 90%, or 95% identical to two or more of the light chain polypeptide sequences provided in Table 3.

In some embodiments, the invention provides libraries wherein the light chain variable regions comprise the polypeptide sequences provided in Table 3.

In certain embodiments, the invention provides libraries comprising polynucleotides encoding light chain variable regions, wherein the L3-VL polypeptide sequences of the light chain variable regions are varied at two or three residues between positions 89 to 94, inclusive, in comparison to an L3-VL germline sequence. In some embodiments, libraries containing a single light chain germline sequence and its variants are provided. In certain embodiments, variants produced from different light chain germline sequences can be combined to produce libraries encoding multiple light chain germline sequences and their variants. Any of the light chain L3-VL germline sequences provided herein may be varied at two or three residues between positions 89 to 94, inclusive, and one of ordinary skill in the art will recognize that any other L3-VL sequence can also be varied according to the principles described herein to produce libraries provided by the invention. In some embodiments, the present invention comprises libraries containing polynucleotides that encode antibody light chain variable regions, wherein the antibody light chain variable regions comprise one or more of the following L3-VL sequences: (i) an amino acid sequence that is identical to an L3-VL germline sequence (e.g., see Table 1); (ii) an amino acid sequence that contains two substitutions between residues 89-94, inclusive, in comparison to an L3-VL germline sequence; and (iii) an amino acid sequence that contains three substitutions between residues 89-94, inclusive, in comparison to an L3-VL germline sequence. In some embodiments, each antibody light chain variable region on a library includes one or more of the above L3-VL sequences. In some embodiments, such a library is combined with one or more sets of other nucleic acids that may or may not encode antibody light chain variable regions, and may or may not contain such L3-VL sequences. In some embodiments, the present invention comprises libraries containing polynucleotides that encode an antibody light chain variable region having an amino acid sequence as set forth in Table 4, or a polynucleotide sequence as set forth in one or more of Tables 5-7, wherein two or three residues at positions 89-94, inclusive, are varied.

In some embodiments, the present invention comprises libraries containing polynucleotides that encode an antibody light chain variable region, wherein, across the library, all encoded antibody light chain variable regions are identical to one another except for substitutions of residues at positions between residue 89 and residue 94, inclusive and further wherein, across the library, sequences of any two encoded antibody light chain variable regions differ from one another at not more than 3 positions.

In some embodiments, the invention provides libraries comprising polynucleotides encoding light chain variable regions comprising polypeptide sequences at least about 80%, 90%, or 95% identical to polypeptides produced by translation of two or more of the polynucleotide sequences provided in Tables 5-7. In certain embodiments all members of the library are at least about 80%, 90%, or 95% identical to polypeptides produced by translation of two or more of the polynucleotide sequences provided in Tables 5-7.

In certain embodiments, the invention provides a library comprising light chain variable regions that comprise the polypeptides produced by translation of the polynucleotide sequences provided in Tables 5-7. In certain embodiments, all members of the library comprise the polypeptides produced by translation of the polynucleotide sequences provided in Tables 5-7.

In some embodiments, any of the libraries described herein as containing or encoding CDRL3 and/or light chain variable regions, contains or encodes such CDRL3 and/or light chain variable regions in the context of complete light chains. Furthermore, in some embodiments, such libraries (and/or complete light chain libraries) further contain or encode one or more heavy chain CDRH3, variable domains, or intact heavy chains. In some embodiments, provided libraries include or encode intact antibodies such as, for example, intact intact IgGs.

In some embodiments, provided libraries include or encode human antibodies or antibody fragments; in some such embodiments, provided libraries include or encode intact human antibodies.

In certain embodiments, the invention provides libraries that comprise nucleic acid vectors containing library nucleic acids described herein. In many embodiments, each such library member comprises the same vector.

In some embodiments, the invention provides host cells containing one or more provided libraries, for example including a vector. In some embodiments the host cell is a yeast, and in certain embodiments the yeast is *Saccharomyces cerevisiae*.

In some embodiments, the invention provides antibodies isolated from the libraries described herein.

In certain embodiments, the invention provides kits containing any of the libraries described herein.

In some embodiments, the invention provides representations of libraries and/or theoretical segment pools in a computer readable format, for example, the TN1 polypeptides of Tables 10, 23-25 and 26; the DH polypeptides of Tables 11, 23-25 and 28; the N2 polypeptides of Tables 12, 23-25 and 30; the H3-JH polypeptides of Tables 13, 15, 17, 23-25 and 32; the TN1 polynucleotides of Tables 25-26; the DH polynucleotides of Tables 25 and 27; the N2 polynucleotides of Tables 25 and 29; and/or the H3-JH polynucleotides of Tables 25 and 31.

In certain embodiments, the invention provides a representation of the polynucleotide sequences of the Human Preimmune Set (Appendix A), or the polypeptide expression products thereof, in a computer readable format.

In some embodiments, the invention provides a method of making synthetic polynucleotides encoding a CDRH3 library, comprising: (a) providing a theoretical segment pool containing TN1, DH, N2, and H3-JH segments; (b) providing a reference set of CDRH3 sequences; (c) utilizing the theoretical segment pool of (a) to identify the closest match(es) to each CDRH3 sequence in the reference set of (b); (d) selecting segments from the theoretical segment pool for inclusion in a synthetic library; and (e) synthesizing the synthetic CDRH3 library. In certain embodiments, the invention provides libraries made by this method. In some embodiments, the segments selected for inclusion in the synthetic library are selected according to their segment usage weight in the reference set of CDRH3 sequences.

In certain embodiments, the invention provides a method of making synthetic polynucleotides encoding a CDRL3 library, comprising: (i) obtaining a reference set of light chain sequences, wherein the reference set contains light chain sequences with VL segments originating from the same IGVL germline gene and/or its allelic variants; (ii) determining which amino acids occur at each of the CDRL3 positions in the reference set that are encoded by the IGVL gene; (iii) synthesizing light chain variable domain encoding sequences wherein two positions between positions 89 and 94, inclusive, contain degenerate codons encoding two or more of the five most frequently occurring amino acid residues at the corresponding positions in the reference set; and (iv) synthesizing the polynucleotides encoding the CDRL3 library. In certain embodiments, the invention provides libraries made by this method.

In some embodiments, the invention provides a method of using any of the libraries of the invention to isolate an antibody binding an antigen, comprising contacting the polypeptide expression products of said libraries with an antigen and isolating polypeptide expression products that bind to the antigen.

In certain embodiments, the number of N-linked glycosylation sites, deamidation motifs, and/or Cys residues in the libraries of the invention are reduced or eliminated in comparison to libraries produced by amplification of a repertoire from a biological source.

The invention provides a number of polynucleotide and polypeptide sequences and segments that can be used to build larger polynucleotide and polypeptide sequences (e.g., TN1, DH, N2, and H3-JH segments that can be used to build CDRH3). One of ordinary skill in the art will readily recognize that in some instances these sequences can be more succinctly represented by providing consensus sequences after alignment of the sequences provided by the invention, and that these consensus sequences fall within the scope of the invention and may be used to more succinctly represent any of the sequences provided herein.

BRIEF DESCRIPTION OF THE DRAWING

FIG. 4 shows the application of a provided method used to generate nucleotide sequences (SEQ ID NOS 8748-8759, respectively, in order of appearance) encoding the parent H3-JH segments.

FIG. 8 shows that Exemplary Library Design 3 (ELD-3) and the Extended Diversity Library Design both return better matches to clinically relevant CDRH3 sequences than the LUA-141 library.

DETAILED DESCRIPTION OF CERTAIN EMBODIMENTS OF THE INVENTION

Figure 1:
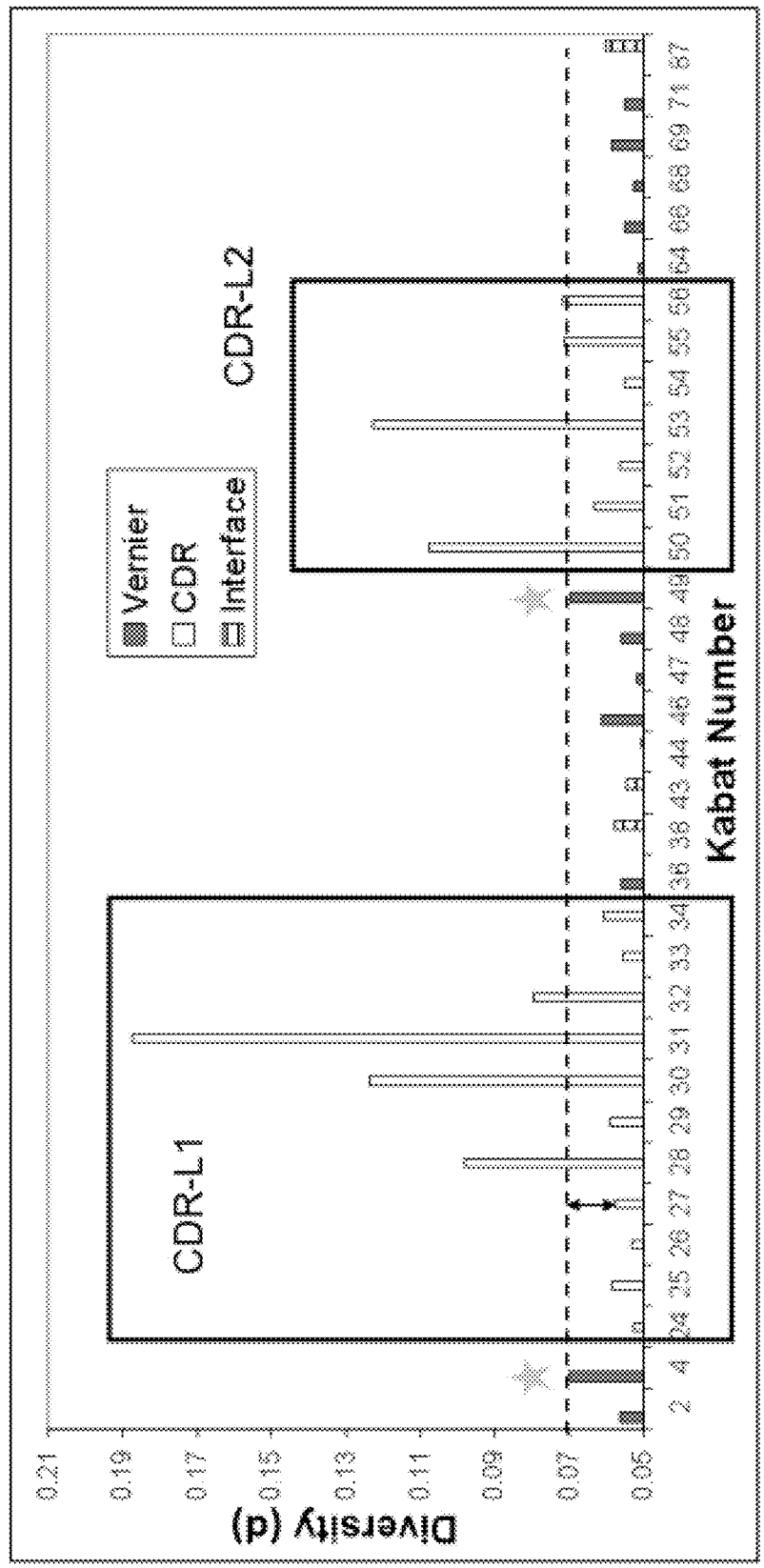
FIG. 1 shows that Vernier residues 4 and 49 (starred) in VK1-39 have a diversity index comparable to or greater than the diversity indices of the CDR positions (i.e., at or above 0.07, in this example).

The present invention provides, among other things, polynucleotide and polypeptide libraries, methods of producing and using the libraries, kits containing the libraries, and computer readable forms of representations of libraries and/or theoretical segment pools disclosed herein. Libraries taught in this application can be described, at least in part, in terms of components (e.g., polynucleotide or polypeptide "segments") from which they are assembled. Among other things, the present invention specifically provides and contemplates these polynucleotide or polypeptide segments, methods of producing and using such segments, and kits and computer readable forms of representations that include such library segments.

In certain embodiments, the invention provides antibody libraries specifically designed based on sequences and CDR length distribution in a naturally occurring human antibody repertoire. It is estimated that, even in the absence of antigenic stimulation, an individual human makes at least about $10^7$ different antibody molecules (Boyd et al., Science Translational Medicine, 2009, 1:1). The antigen-binding sites of many antibodies can cross-react with a variety of related but different epitopes. In addition, the human antibody repertoire is large enough to ensure that there is an antigen-binding site to fit almost any potential epitope, albeit potentially with low affinity.

The mammalian immune system has evolved unique genetic mechanisms that enable it to generate an almost unlimited number of different light and heavy chains in a remarkably economical way, by combinatorially joining chromosomally separated gene segments prior to transcription. Each type of immunoglobulin (Ig) chain (i.e., kappa light, lambda light, and heavy) is synthesized by combinatorial assembly of DNA sequences, selected from two or more families of gene segments, to produce a single polypeptide chain. Specifically, the heavy chains and light chains each consist of a variable region and a constant (C) region. The variable regions of the heavy chains are encoded by DNA sequences assembled from three families of gene sequences: variable (IGHV), diversity (IGHD), and joining (IGHJ). The variable regions of light chains are encoded by DNA sequences assembled from two families of gene sequences for each of the kappa and lambda light chains: variable (IGLV) and joining (IGLJ). Each variable region (heavy and light) is also recombined with a constant region, to produce a full-length immunoglobulin chain.

While combinatorial assembly of the V, D and J gene segments make a substantial contribution to antibody variable region diversity, further diversity is introduced in vivo, at the pre-B cell stage, via imprecise joining of these gene segments and the introduction of non-templated nucleotides at the junctions between the gene segments (see e.g., U.S. Pub. No. 2009/0181855, which is incorporated by reference in its entirety, for more information).

After a B cell recognizes an antigen, it is induced to proliferate. During proliferation, the B cell receptor locus undergoes an extremely high rate of somatic mutation that is far greater than the normal rate of genomic mutation. The mutations that occur are primarily localized to the Ig variable regions and comprise substitutions, insertions and deletions. This somatic hypermutation enables the production of B cells that express antibodies possessing enhanced affinity toward an antigen. Such antigen-driven somatic hypermutation fine-tunes antibody responses to a given antigen.

Synthetic antibody libraries of the instant invention have the potential to recognize any antigen, including antigens of human origin. The ability to recognize antigens of human origin may not be present in other antibody libraries, such as antibody libraries prepared from human biological sources (e.g., from human cDNA), because self-reactive antibodies are removed by the donor's immune system via negative selection.

Still further, the present invention provides strategies that streamline and/or simplify certain aspects of library development and/or screening. For example, in some embodiments, the present invention permits use of cell sorting technologies (e.g., fluorescence activated cell sorting, FACS) to identify positive clones, and therefore bypasses or obviates the need for the standard and tedious methodology of generating a hybridoma library and supernatant screening.

Yet further, in some embodiments, the present invention provides libraries and/or sublibraries that accommodate multiple screening passes. For example, in some embodiments, provided libraries and/or sublibraries can be screened multiple times. In some such embodiments, individual provided libraries and/or sublibraries can be used to discover additional antibodies against many targets.

Before further description of the invention, certain terms are defined.

Definitions

Unless defined otherwise, all technical and scientific terms used herein have the meaning commonly understood by one of ordinary skill in the art relevant to the invention. Unless otherwise specified, the Kabat numbering system is used throughout the application. The definitions below supplement those in the art and are directed to the embodiments described in the current application.

The term "amino acid" or "amino acid residue," as would be understood by one of ordinary skill in the art, typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a non-polar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr).

As would be understood by those of ordinary skill in the art, the term "antibody" is used herein in the broadest sense and specifically encompasses at least monoclonal antibodies, polyclonal antibodies, multi-specific antibodies (e.g., bispecific antibodies), chimeric antibodies, humanized antibodies, human antibodies, and antibody fragments. An antibody is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes.

The term "antibody binding region" refers to one or more portions of an immunoglobulin or antibody variable region capable of binding an antigen(s). Typically, the antibody binding region is, for example, an antibody light chain (or variable region or one or more CDRs thereof), an antibody heavy chain (or variable region or one or more CDRs thereof), a heavy chain Fd region, a combined antibody light and heavy chain (or variable regions thereof) such as a Fab, F(ab)$_2$, single domain, or single chain antibodies (scFv), or any region of a full length antibody that recognizes an antigen, for example, an IgG (e.g., an IgG1, IgG2, IgG3, or IgG4 subtype), IgA1, IgA2, IgD, IgE, or IgM antibody.

"Antibody fragments" comprise a portion of an intact antibody, for example, one or more portions of the antigen-binding region thereof. Examples of antibody fragments include Fab, Fab', F(ab')$_2$, and Fv fragments, diabodies, linear antibodies, single-chain antibodies, and multi-specific antibodies formed from intact antibodies and antibody fragments.

The term "antibody of interest" refers to an antibody that has a property of interest that is identified and/or isolated from a library of the invention. Exemplary properties of interest include, for example, but are not limited to, binding to a particular antigen or epitope, binding with a certain affinity, cross-reactivity, blocking a binding interaction between two molecules, and/or eliciting a certain biological effect.

The term "canonical structure," as understood by those of ordinary skill in the art, refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol., 1996, 263: 800, each of which is incorporated by reference in its entirety). Furthermore, there is a relationship between the adopted loop structure and the amino acid sequences surrounding it. As is known in the art, the conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues. The term "canonical structure" may also include considerations as to the linear sequence of the antibody, for example, as catalogued by Kabat (Kabat et al., in "Sequences of Proteins of Immunological Interest," 5$^{th}$ Edition, U.S. Department of Heath and Human Services, 1992). The Kabat numbering scheme is a widely adopted standard for numbering the amino acid residues of an antibody variable domain in a consistent manner, and is used herein unless indicated otherwise. Additional structural considerations can also be used to determine the canonical structure of an antibody. For example, those differences not fully reflected by Kabat numbering can be described by the numbering system of Chothia et al. and/or revealed by other techniques, for example, crystallography and two or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., and their implications for construing canonical aspects of antibody structure, are described in the literature.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise framework regions. The exact definitional CDR boundaries and lengths are subject to different classification and numbering systems. CDRs may therefore be referred to by Kabat, Chothia, contact or other boundary definitions, including for example the CDRH3 numbering system described below. Despite differing boundaries, each of these systems has some degree of overlap in what constitutes the so called "hypervariable regions" within the variable region. CDR definitions according to these systems may therefore differ in length and boundary areas with respect to the adjacent framework region. See, for example Kabat et al., in "Sequences of Proteins of Immunological Interest," 5$^{th}$ Edition, U.S. Department of Health and Human Services, 1992; Chothia et al., J. Mol. Biol., 1987, 196: 901; and MacCallum et al., J. Mol. Biol., 1996, 262: 732, each of which is incorporated by reference in its entirety.

The "CDRH3 numbering system" used herein defines the first amino acid of CDRH3 as being at position 95 and the last amino acid of CDRH3 as position 102. Note that this is a custom numbering system that is not according to Kabat. The amino acid segment, beginning at position 95 is called "TN1" and, when present, is assigned numbers 95, 96, 96A, 96B, etc. Note that the nomenclature used in the current application is slightly different from that used in U.S. Publication Nos. 2009/0181855 and 2010/0056386, and WO/2009/036379. In those applications, position 95 was designated a "Tail" residue, while here, the Tail (T) has been combined with the N1 segment, to produce one segment, designated "TN1." The TN1 segment is followed by the "DH" segment, which is assigned numbers 97, 97A, 97B, 97C, etc. The DH segment is followed by the "N2" segment, which, when present, is numbered 98, 98A, 98B, etc. Finally, the most C-terminal amino acid residue of the "H3-JH" segment is designated as number 102. The residue directly before (N-terminal) it, when present, is 101, and the one before (if present) is 100. The rest of the H3-JH amino acids are numbered in reverse order, beginning with 99 for the amino acid just N-terminal to 100, 99A for the residue N-terminal to 99, and so forth for 99B, 99C, etc. Examples of CDRH3 sequence residue numbers may therefore include the following:

As used herein, a sequence designed with "directed diversity" has been specifically designed to contain both sequence diversity and length diversity. Directed diversity is not stochastic.

As used herein, the term "diversity" refers to a variety or a noticeable heterogeneity. The term "sequence diversity" refers to a variety of sequences which are collectively representative of several possibilities of sequences, for example, those found in natural human antibodies. For example, CDRH3 sequence diversity may refer to a variety of possibilities of combining the known human TN1, DH, N2, and H3-JH segments to form CDRH3 sequences. The CDRL3 sequence diversity (kappa or lambda) may refer to a variety of possibilities of combining the naturally occurring light chain variable region contributing to CDRL3 (i.e., "L3-VL") and joining (i.e., "L3-JL") segments, to form CDRL3 sequences. As used herein, "H3-JH" refers to the portion of the IGHJ gene contributing to CDRH3. As used herein, "L3-VL" and "L3-JL" refer to the portions of the IGLV and IGLJ genes (kappa or lambda) contributing to CDRL3, respectively.

13 Amino Acid CDR-H3 with TN1 and N2

```
(95) (96) (96A)    (97) (97A) (97B) (97C) (97D)      (98)    (99) (100) (101) (102)
|------------|-------------------------|----|------------------|
     TN1                  DH                  N2           H3-JH
```

10 Amino Acid CDR-H3 without TN1 and N2

```
(97) (97A) (97B) (97C) (97D) (97E) (97F) (97G)       (101) (102)
|--------------------------------------|---------|
                    DH                         H3-JH
```

"Chassis" of the invention are portions of the antibody heavy chain variable (IGHV) or light chain variable (IGLV) domains that are not part of CDRH3 or CDRL3, respectively. A chassis of the invention is defined as the portion of the variable region of an antibody beginning with the first amino acid of FRM1 and ending with the last amino acid of FRM3. In the case of the heavy chain, the chassis includes the amino acids including from position 1 to position 94. In the case of the light chains (kappa and lambda), the chassis are defined as including from position 1 to position 88. The chassis of the invention may contain certain modifications relative to the corresponding germline variable domain sequences. These modifications may be engineered (e.g., to remove N-linked glycosylation sites) or naturally occurring (e.g., to account for naturally occurring allelic variation). For example, it is known in the art that the immunoglobulin gene repertoire is polymorphic (Wang et al., Immunol. Cell. Biol., 2008, 86: 111; Collins et al., Immunogenetics, 2008, 60: 669, each incorporated by reference in its entirety); chassis, CDRs and constant regions representative of these allelic variants are also encompassed by the invention. In some embodiments, the allelic variant(s) used in a particular embodiment of the invention may be selected based on the allelic variation present in different patient populations, for example, to identify antibodies that are non-immunogenic in these patient populations. In certain embodiments, the immunogenicity of an antibody of the invention may depend on allelic variation in the major histocompatibility complex (MHC) genes of a patient population. Such allelic variation may also be considered in the design of libraries of the invention. In certain embodiments of the invention, the chassis and constant regions are contained in a vector, and a CDR3 region is introduced between them via homologous recombination.

As used herein, the term "expression" refers to steps involved in the production of a polypeptide including, but not limited to, transcription, post-transcriptional modification, translation, post-translational modification, and secretion.

The term "framework region" refers to the art-recognized portions of an antibody variable region that exist between the more divergent (i.e., hypervariable) CDRs. Such framework regions are typically referred to as frameworks 1 through 4 (FRM1, FRM2, FRM3, and FRM4) and provide a scaffold for the presentation of the six CDRs (three from the heavy chain and three from the light chain) in three dimensional space, to form an antigen-binding surface.

The term "full-length heavy chain" refers to an immunoglobulin heavy chain that contains each of the canonical structural domains of an immunoglobulin heavy chain, including the four framework regions, the three CDRs, and the constant region.

The term "full-length light chain" refers to an immunoglobulin light chain that contains each of the canonical structural domains of an immunoglobulin light chain, including the four framework regions, the three CDRs, and the constant region.

The term "germline-like," when used with respect to the CDRL3 sequences of the light chains of the invention, means those sequences consisting of combinations of: (i) the first six wild-type residues contributed to CDRL3 by the IGVL germline gene (i.e., positions 89 to 94 in the Kabat numbering system; "L" is kappa or lambda); and (ii) one of several amino acid sequences, two one to four amino acids in length, largely, but not exclusively, derived from the JL segment ("L," again is kappa or lambda). For kappa CDRL3 sequences of the most common lengths (i.e., 8, 9, and 10 residues), the sequences of (ii) number twenty and are: FT, LT, IT, RT, WT, YT, [X]T, [X]PT, [X]FT, [X]LT, [X]IT, [X]RT, [X]WT, [X]YT, [X]PFT, [X]PLT, [X]PIT, [X]PRT, [X]PWT and [X]PYT, where [X] corresponds to the amino acid residue found at position 95 (Kabat) in the respective VK germline sequence. X is most commonly P, but may also be S or any other amino acid residue found at position 95 of a VK germline sequence. For eight exemplified VK chassis exemplified herein, the corresponding 160 germline-like sequences, (i.e., 20 sequences of two to four amino acids in length combined with positions 89 to 94 of each of eight VK germline sequences) are provided in Table 1. A similar approach is applied to define germline-like CDRL3 sequences for lambda light chains. As for the kappa sequences described above, the intact, un-mutated portions of CDRL3 encoded by the IGVL genes (in this case, IGVλ) would be combined with the sequences largely, but not exclusively, derived from the Jλ segment. Here, the latter sequences (corresponding to (ii), above), number five and are: YV, VV, WV, AV or V. In addition, and as described in Example 7 of US 2009/0818155, one could further allow for variation at the last position of the Vλ-gene-encoded portion of CDRL3 by considering partial codons, while still considering the resulting sequences "germline-like." More specifically, the entire "minimalist library" of Example 7 in US 2009/0818155 would be defined as "germline-like." One of ordinary skill in the art will readily recognize that these methods can be extended to other VK and Vλ sequences.

The term "genotype-phenotype linkage," as understood by those of ordinary skill in the art, refers to the fact that the nucleic acid (genotype) encoding a protein with a particular phenotype (e.g., binding an antigen) can be isolated from a library. For the purposes of illustration, an antibody fragment expressed on the surface of a phage can be isolated based on its binding to an antigen (e.g., U.S. Pat. No. 5,837,500). The binding of the antibody to the antigen simultaneously enables the isolation of the phage containing the nucleic acid encoding the antibody fragment. Thus, the phenotype (antigen-binding characteristics of the antibody fragment) has been "linked" to the genotype (nucleic acid encoding the antibody fragment). Other methods of maintaining a genotype-phenotype linkage include those of Wittrup et al. (U.S. Pat. Nos. 6,300,065, 6,331,391, 6,423,538, 6,696,251, 6,699,658, and U.S. Pub. No. 20040146976, each of which is incorporated by reference in its entirety), Miltenyi (U.S. Pat. No. 7,166,423, incorporated by reference in its entirety), Fandl (U.S. Pat. No. 6,919,183, US Pub No. 20060234311, each incorporated by reference in its entirety), Clausell-Tormos et al. (Chem. Biol., 2008, 15: 427, incorporated by reference in its entirety), Love et al. (Nat. Biotechnol., 2006, 24: 703, incorporated by reference in its entirety), and Kelly et al. (Chem. Commun., 2007, 14: 1773, incorporated by reference in its entirety). The term can be used to refer to any method which localizes an antibody protein together with the gene encoding the antibody protein, in a way in which they can both be recovered while the linkage between them is maintained.

The term "heterologous moiety" is used herein to indicate the addition of a moiety to an antibody wherein the moiety is not part of a naturally-occurring antibody. Exemplary heterologous moieties include drugs, toxins, imaging agents, and any other compositions which might provide an activity that is not inherent in the antibody itself.

As used herein, the term "host cell" is intended to refer to a cell comprising a polynucleotide of the invention. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "human antibody CDR library" includes at least a polynucleotide or polypeptide library which has been designed to represent the sequence diversity and length diversity of naturally occurring CDRs in human antibodies (e.g., the term "CDR" in "human antibody CDR library" may be substituted with "CDRL1," "CDRL2," "CDRL3," "CDRH1," "CDRH2," and/or "CDRH3"). Known human CDR sequences are represented in various data sets, including Jackson et al., J. Immunol Methods, 2007, 324: 26; Martin, Proteins, 1996, 25: 130; Lee et al., Immunogenetics, 2006, 57: 917, Boyd et al., Science Translational Medicine, 2009, 1: 1, and WO/2009/036379, each of which is incorporated by reference in its entirety, and the HPS, which is provided in Appendix A.

The term "Human Preimmune Set," or "HPS," refers to a reference set of 3,571 curated human preimmune heavy chain sequences corresponding to the GI Nos. provided in Appendix A.

An "intact antibody" is one comprising full-length heavy- and light-chains (i.e., four frameworks, three CDRs, and a constant region for each of the heavy and light chains). An intact antibody is also referred to as a "full-length" antibody.

The term "length diversity" refers to a variety in the length of a family of nucleotide or amino acid sequence. For example, in naturally occurring human antibodies, the heavy chain CDR3 sequence varies in length, for example, from about 2 amino acids to over about 35 amino acids, and the light chain CDR3 sequence varies in length, for example, from about 5 to about 16 amino acids.

The term "library" refers to a set of entities comprising two or more entities having diversity as described herein, and/or designed according to the methods of the invention. For example, a "library of polynucleotides" refers to a set of polynucleotides comprising two or more polynucleotides having diversity as described herein, and/or designed according to the methods of the invention. A "library of polypeptides" refers to a set of polypeptides comprising two or more polypeptides having diversity as described herein, and/or designed according to the methods of the invention. A "library of synthetic polynucleotides" refers to a set of polynucleotides comprising two or more synthetic polynucleotides having diversity as described herein, and/or designed according to the methods of the invention. Libraries where all members are synthetic are also encompassed by the invention. A "human antibody library" refers to a set of polypeptides comprising two or more polypeptides having diversity as described herein, and/or designed according to the methods of the invention, for example a library designed to represent the sequence diversity and length diversity of naturally occurring human antibodies. In some embodiments, the term "library" may refer to a set of entities sharing similar structural or sequence characteristics, for example, a "heavy chain library," "light chain library," "antibody library," and/or "CDRH3 library."

The term "physical realization" refers to a portion of a theoretical (e.g., computer-based) or synthetic (e.g., oligonucleotide-based) diversity that can actually be physically sampled, for example, by any display methodology. Exemplary display methodology include: phage display, ribosomal display, and yeast display. For synthetic sequences, the size of the physical realization of a library depends on (1) the fraction of the theoretical diversity that can actually be synthesized, and (2) the limitations of the particular screening method. Exemplary limitations of screening methods include the number of variants that can be screened in a particular assay (e.g., ribosome display, phage display, yeast display) and the transformation efficiency of the host cells (e.g., yeast, mammalian cells, bacteria) which are used in a screening assay. For the purposes of illustration, given a library with a theoretical diversity of $10^{12}$ members, an exemplary physical realization of the library (e.g., in yeast, bacterial cells, or ribosome display) that can maximally include $10^{11}$ members will, therefore, sample about 10% of the theoretical diversity of the library. However, if fewer than $10^{11}$ members of the library with a theoretical diversity of $10^{12}$ are synthesized, and the physical realization of the library can maximally include $10^{11}$ members, less than 10% of the theoretical diversity of the library is sampled in the physical realization of the library. Similarly, a physical realization of the library that can maximally include more than $10^{12}$ members would "oversample" the theoretical diversity, meaning that each member may be present more than once (assuming that the entire $10^{12}$ theoretical diversity is synthesized).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety. The representation of nucleotide bases herein follows International Union of Pure and Applied Chemistry (IUPAC) nomenclature (see U.S. Pub. No. 2009/0181855, incorporated by reference in its entirety).

"Preimmune" antibody libraries have sequence diversities and length diversities similar to naturally occurring human antibody sequences before these sequences have undergone negative selection and/or somatic hypermutation. For example, the set of sequences described in Lee et al. (Immunogenetics, 2006, 57: 917, incorporated by reference in its entirety) and the Human Preimmune Set (HPS) described herein (see Appendix A) are believed to represent sequences from the preimmune repertoire. In certain embodiments of the invention, the sequences of the invention will be similar to these sequences (e.g., in terms of composition and length).

As used herein, the term "sitewise stochastic" describes a process of generating a sequence of amino acids, where only the amino acid occurrences at the individual positions are considered, and higher order motifs (e.g., pair-wise correlations) are not accounted for (e.g., see Knappik, et al., J Mol Biol, 2000, 296: 57, and analysis provided in U.S. Publication No. 2009/0181855, each incorporated by reference in its entirety).

The term "split-pool synthesis" refers to a procedure in which the products of a plurality of individual first reactions are combined (pooled) and then separated (split) before participating in a plurality of second reactions. For example, U.S. Publication No. 2009/0181855 (incorporated by reference in its entirety) describes the synthesis of 278 DH segments (products), each in a separate reaction. After synthesis, these 278 segments are combined (pooled) and then distributed (split) amongst 141 columns for the synthesis of the N2 segments. This enables the pairing of each of the 278 DH segments with each of 141 N2 segments.

As used herein, "stochastic" describes a process of generating a random sequence of nucleotides or amino acids, which is considered as a sample of one element from a probability distribution (e.g., see U.S. Pat. No. 5,723,323).

As used herein, the term "synthetic polynucleotide" refers to a molecule formed through a chemical process, as opposed to molecules of natural origin, or molecules derived via template-based amplification of molecules of natural origin (e.g., immunoglobulin chains cloned from populations of B cells via PCR amplification are not "synthetic" as used herein). In some instances, for example, when referring to libraries of the invention that comprise multiple segments (e.g., TN1, DH, N2, and/or H3-JH), the invention encompasses libraries in which at least one, two, three, or four of the aforementioned components is synthetic. By way of illustration, a library in which certain components are synthetic, while other components are of natural origin or derived via template-based amplification of molecules of natural origin, would be encompassed by the invention. Libraries that are fully synthetic would, of course, also be encompassed by the invention.

The term "theoretical diversity" refers to the maximum number of variants in a library design. For example, given an amino acid sequence of three residues, where residues one and three may each be any one of five amino acid types and residue two may be any one of 20 amino acid types, the theoretical diversity is $5 \times 20 \times 5 = 500$ possible sequences. Similarly if sequence X is constructed by combination of 4 amino acid segments, where segment 1 has 100 possible sequences, segment 2 has 75 possible sequences, segment 3 has 250 possible sequences, and segment 4 has 30 possible sequences, the theoretical diversity of fragment X would be $100 \times 75 \times 200 \times 30$, or $5.6 \times 10^5$ possible sequences.

The term "theoretical segment pool" refers to a set of polynucleotide or polypeptide segments that can be used as building blocks to assemble a larger polynucleotide or polypeptide. For example, a theoretical segment pool containing TN1, DH, N2, and H3-JH segments can be used to assemble a library of CDRH3 sequences by concatenating them combinatorially to form a sequence represented by [TN1]-[DH]-[N2]-[H3-JH], and synthesizing the corresponding oligonucleotide(s). The term "theoretical segment pool" can apply to any set of polynucleotide or polypeptide segments. Thus, while a set of TN1, DH, N2, and H3-JH segments are collectively considered a theoretical segment pool, each of the individual sets of segments also comprise a theoretical segment pool, specifically a TN1 theoretical segment pool, a DH theoretical segment pool, an N2 theoretical segment pool, and an H3-JH theoretical segment pool. Any subsets of these theoretical segment pools containing two or more sequences can also be considered theoretical segment pools.

The term "unique," as used herein, refers to a sequence that is different (e.g., has a different chemical structure) from every other sequence within the designed set (e.g., the theoretical diversity). It should be understood that there are likely to be more than one copy of many unique sequences from the theoretical diversity in a particular physical realization. For example, a library comprising three unique sequences at the theoretical level may comprise nine total members if each sequence occurs three times in the physical realization of the library. However, in certain embodiments, each unique sequence may occur only once, less than once, or more than once.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable" regions or "complementarity determining regions" (CDRs). The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al. Sequences of Proteins of Immunological Interest, 5th Ed. Public Health Service, National Institutes of Health, Bethesda, Md., 1991, incorporated by reference in its entirety). The constant domains are not directly involved in antigen binding, but exhibit various effector functions, such as, for example, antibody-dependent, cell-mediated cytotoxicity and complement activation.

Libraries of the invention containing "VKCDR3" sequences and "VλCDR3" sequences refer to the kappa and lambda sub-sets of the light chain CDR3 (CDRL3) sequences, respectively. Such libraries may be designed with directed diversity, to collectively represent the length and sequence diversity of the human antibody CDRL3 repertoire. "Preimmune" versions of these libraries have similar sequence diversities and length diversities as naturally occurring human antibody CDRL3 sequences before these sequences undergo negative selection and/or somatic hypermutation. Known human CDRL3 sequences are represented in various data sets, including the NCBI database, WO/2009/036379, and Martin, Proteins, 1996, 25: 130 each incorporated by reference in its entirety.

General Design of Libraries

Antibody libraries provided by the present invention may be designed to reflect certain aspects of the preimmune repertoire as created by the human immune system. Certain libraries of the invention are based on rational design informed by collections of human V, D, and J genes, and large databases of human heavy and light chain sequences (e.g., publicly known germline sequences and sequences from Jackson et al., J. Immunol Methods, 2007, 324: 26; Lee et al., Immunogenetics, 2006, 57: 917; Boyd et al., Science Translational Medicine, 2009, 1: 1-8, each incorporated by reference in its entirety; and sequences compiled from rearranged VK and Vλ sequences (see WO/2009/036379, also incorporated by reference in its entirety). Additional information may be found, for example, in Scaviner et al., Exp. Clin. Immunogenet., 1999, 16: 234; Tomlinson et al., J. Mol. Biol., 1992, 227: 799; and Matsuda et al., J. Exp. Med., 1998, 188: 2151, each incorporated by reference in its entirety.

In certain embodiments of the invention, segments representing the possible V, D, and J diversity found in the human repertoire, as well as junctional diversity (i.e., TN1 and N2), are synthesized de novo as single or double-stranded DNA oligonucleotides. In certain embodiments of the invention, oligonucleotides encoding CDR sequences are introduced into yeast along with one or more acceptor vectors containing heavy or light chain chassis sequences and constant domains. No primer-based PCR amplification or template-directed cloning steps from mammalian cDNA or mRNA are employed. Through standard homologous recombination, the recipient yeast recombines the CDR segments with the acceptor vectors containing the chassis sequences and constant regions, to create a properly ordered synthetic, full-length human heavy chain and/or light chain immunoglobulin library that can be genetically propagated, expressed, presented, and screened. One of ordinary skill in the art will readily recognize that the acceptor vector can be designed so as to produce constructs other than full-length human heavy chains and/or light chains. For example, in certain embodiments of the invention, the chassis may be designed to encode portions of a polypeptide encoding an antibody fragment or subunit of an antibody fragment, so that a sequence encoding an antibody fragment, or subunit thereof, is produced when the oligonucleotide cassette containing the CDR is recombined with the acceptor vector.

Thus, in certain embodiments, the invention provides a synthetic, preimmune human antibody repertoire the repertoire comprising:

(a) one or more selected human antibody heavy chain chassis (i.e., amino acids 1 to 94 of the heavy chain variable region, using Kabat's definition);

(b) a CDRH3 repertoire (described more fully below), designed based on the human IGHD and IGHJ germline sequences, and the extraction of TN1 and N2 sequences from reference sets of human CDRH3 sequences, the CDRH3 repertoire comprising (i) a TN1 segment; (ii) a DH segment; (iii) an N2 segment; (iv) an H3-JH segment.

(c) one or more selected human antibody kappa and/or lambda light chain chassis; and (d) a CDRL3 repertoire designed based on the human IGLV and IGLJ germline sequences, wherein "L" may be a kappa or lambda light chain.

The instant invention also provides methods for producing and using such libraries, as well as libraries comprising one or more immunoglobulin domains or antibody fragments. Design and synthesis of each component of the antibody libraries of the invention is provided in more detail below.

Design of Antibody Library Chassis Sequences

In certain embodiments, provided libraries are constructed from selected chassis sequences that are based on naturally occurring variable domain sequences (e.g., IGHV and IGLV genes). The selection of such chassis sequences can be done arbitrarily, or through the definition of certain pre-determined criteria. For example, the Kabat database, an electronic database containing non-redundant rearranged antibody sequences, can be queried for those heavy and light chain germline sequences that are most frequently represented. An algorithm such as BLAST, or a more specialized tool such as SoDA (Volpe et al., Bioinformatics, 2006, 22: 438-44, incorporated by reference in its entirety), can be used to compare rearranged antibody sequences with germline sequences (e.g., using the V BASE2 database; see, for example, Retter et al., Nucleic Acids Res., 2005, 33: D671-D674, incorporated by reference in its entirety), or similar collections of human V, D, and J genes, to identify germline families that are most frequently used to generate functional antibodies.

Several criteria can be utilized for the selection of chassis for inclusion in the libraries of the invention. For example, sequences that are known (or have been determined) to express poorly in yeast, or other organisms used in the invention (e.g., bacteria, mammalian cells, fungi, or plants)

can be excluded from the libraries. Chassis may also be chosen based on the representation of their corresponding germline genes in the peripheral blood of humans. In certain embodiments of the invention, it may be desirable to select chassis that correspond to germline sequences that are highly represented in the peripheral blood of humans. In some embodiments, it may be desirable to select chassis that correspond to germline sequences that are less frequently represented, for example, to increase the canonical diversity of the library. Therefore, chassis may be selected to produce libraries that represent the largest and most structurally diverse group of functional human antibodies.

In certain embodiments of the invention, less diverse chassis may be utilized, for example, if it is desirable to produce a smaller, more focused library with less chassis variability and greater CDR variability. In some embodiments of the invention, chassis may be selected based on both their expression in a cell of the invention (e.g., a yeast cell) and the diversity of canonical structures represented by the selected sequences. One may therefore produce a library with a diversity of canonical structures that express well in a cell of the invention.

Design of Heavy Chain Chassis Sequences

The design and selection of heavy chain chassis sequences that can be used in the current invention is described in detail in U.S. Publication Nos. 2009/0181855 and 2010/0056386, and WO/2009/036379, each of which is incorporated by reference in its entirety, and is therefore described only briefly here.

In general, VH domains of the library comprise three components: (1) a VH "chassis," which includes amino acids 1 to 94 (using Kabat numbering), (2) the CDRH3, which is defined herein to include the Kabat CDRH3 proper (positions 95-102), and (3) the FRM4 region, including amino acids 103 to 113 (Kabat numbering). The overall VH domain structure may therefore be depicted schematically (not to scale) as:

these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences. One of ordinary skill in the art will recognize that given the chassis definition provided above, any IGHV-encoding sequence can be adapted for use as a chassis of the invention. As exemplified in U.S. Publication Nos. 2009/0181855 and 2010/0056386, and WO/2009/036379 (each incorporated by reference in its entirety), these chassis can also be varied, particularly by altering the amino acid residues in the CDRH1 and CDRH2 regions, further increasing the diversity of the library.

Design of Light Chain Chassis Sequences

The design and selection of light chain chassis sequences that can be used in the current invention is described in detail in U.S. Publication Nos. 2009/0181855 and 2010/0056386, and WO/2009/036379, each of which is incorporated by reference in its entirety, and is therefore described only briefly here. The light chain chassis of the invention may be based on kappa and/or lambda light chain sequences.

The VL domains of the library comprise three primary components: (1) a VL "chassis", which includes amino acids 1 to 88 (using Kabat numbering), (2) the CDRL3, which is defined herein to include the Kabat CDRL3 proper (positions 89-97), and (3) the FRM4 region, including amino acids 98 to 107 (Kabat numbering). The overall VL domain

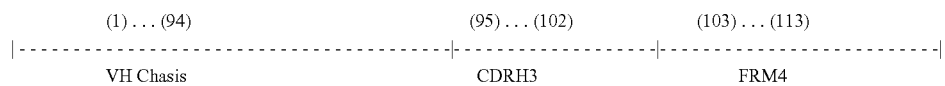

In certain embodiments of the invention, the VH chassis of the libraries may comprise from about Kabat residue 1 to structure may therefore be depicted schematically (not to scale) as:

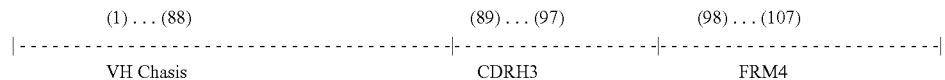

about Kabat residue 94 of one or more of the following IGHV germline sequences: IGHV1-2, IGHV1-3, IGHV1-8, IGHV1-18, IGHV1-24, IGHV1-45, IGHV1-46, IGHV1-58, IGHV1-69, IGH8, IGH56, IGH100, IGHV3-7, IGHV3-9, IGHV3-11, IGHV3-13, IGHV3-15, IGHV3-20, IGHV3-21, IGHV3-23, IGHV3-30, IGHV3-33, IGHV3-43, IGHV3-48, IGHV3-49, IGHV3-53, IGHV3-64, IGHV3-66, IGHV3-72, IGHV3-73, IGHV3-74, IGHV4-4, IGHV4-28, IGHV4-31, IGHV4-34, IGHV4-39, IGHV4-59, IGHV4-61, IGHV4-B, IGHV5-51, IGHV6-1, and/or IGHV7-4-1. In some embodiments of the invention, a library may contain one or more of In certain embodiments of the invention, the VL chassis of the libraries include one or more chassis based on IGKV germline sequences. In certain embodiments of the invention, the VL chassis of the libraries may comprise from about Kabat residue 1 to about Kabat residue 88 of one or more of the following IGKV germline sequences: IGKV1-05, IGKV1-06, IGKV1-08, IGKV1-09, IGKV1-12, IGKV1-13, IGKV1-16, IGKV1-17, IGKV1-27, IGKV1-33, IGKV1-37, IGKV1-39, IGKV1D-16, IGKV1D-17, IGKV1D-43, IGKV1D-8, IGK54, IGK58, IGK59, IGK60, IGK70, IGKV2D-26, IGKV2D-29, IGKV2D-30, IGKV3-11, IGKV3-15, IGKV3-20, IGKV3D-07, IGKV3D-11, IGKV3D-20, IGKV4-1, IGKV5-2, IGKV6-21, and/or IGKV6D-41. In some embodiments of the invention, a library may contain one or more of these sequences, one or more allelic variants of these sequences, or encode an amino acid sequence at least about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 89%, 88%, 87%, 86%, 85%, 84%, 83%, 82%, 81%, 80%, 77.5%, 75%, 73.5%, 70%, 65%, 60%, 55%, or 50% identical to one or more of these sequences.

In certain embodiments of the invention, the VL chassis of the libraries include one or more chassis based on IGλV germline sequences. In certain embodiments of the invention, the VL chassis of the libraries may comprise from about Kabat residue 1 to about Kabat residue 88 of one or more of the following IGλV germline sequences: IGλV3-1, IGλV3-21, IGλ44, IGλV1-40, IGλV3-19, IGλV1-51, IGλV1-44, IGλV6-57, IGλ11, IGλV3-25, IGλ53, IGλV3-10, IGλV4-69, IGλV1-47, IGλ41, IGλV7-43, IGλV7-46, IGλV5-45, IGλV4-60, IGλV10-54, IGλV8-61, IGλV3-9, IGλV1-36, IGλ48, IGλV3-16, IGλV3-27, IGλV4-3, IGλV5-39, IGλV9-49, and/or IGλV3-12. In some embodiments of the invention, a library may contain one or more of these sequences, one or more allelic variants of these sequences, or encode an amino acid sequence at least about 99.9%, 99.5%, 99%, 98%, 97%, 96%, 95%, 94%, 93%, 92%, 91%, 90%, 85%, 80%, 75%, 70%, 65%, 60%, 55%, or 50% identical to one or more of these sequences.

One of ordinary skill in the art will recognize that given the chassis definition provided above, any IGKV- or IGλV-encoding sequence can be adapted for use as a chassis of the invention.

Design and Selection of TN1, DH, N2, and H3-JH Segments

The human germline repertoire contains at least six IGHJ genes (IGHJ1, IGHJ2, IGHJ3, IGHJ4, IGHJ5, and IGHJ6; included in Table 14, where the primary allele is designated "01," and selected allelic variants are designated "02" or "03"), and at least 27 IGHD genes (Table 16, including allelic variants). In some embodiments, the invention comprises a library of CDRH3 polypeptide sequences, or polynucleotide sequences encoding CDRH3 sequences, the library comprising members of any of the theoretical segment pools disclosed herein.

A person of ordinary skill in the art will recognize that not every segment in a theoretical segment pool provided herein is necessary to produce a functional CDRH3 library of the invention. Therefore, in certain embodiments, a CDRH3 library of the invention will contain a subset of the segments of any of the theoretical segment pools described herein. For example, in certain embodiments of the invention, at least about 15, 30, 45, 60, 75, 90, 100, 105, 120, 135, 150, 165, 180, 195, 200, 210, 225, 240, 255, 270, 285, 300, 320, 340, 360, 380, 400, 420, 440, 460, 480, 500, 520, 540, 560, 580, 600, 620, 640, or 643 of the H3-JH segments of any of the theoretical segment pools provided herein, or generated by the methods described herein, are included in a library. In some embodiments of the invention, at least about 15, 30, 45, 60, 75, 90, 100, 105, 120, 135, 150, 165, 180, 195, 200, 250, 300, 350, 400, 450, 500, 550, 600, 650, 700, 750, 800, 850, 900, 950, 1000, 1050, 1100, 1111, 2000, 3000, 4000, 5000, 6000, 7000, 14000, 21000, 28000, 35000, 42000, 49000, 56000, 63000, or 68374 of the DH segments of any of the theoretical segment pools provided herein, or generated by the methods described herein, are included in a library. In some embodiments of the invention, at least about 10, 20, 30, 40, 50, 60, 70, 80, 90, 100, 110, 120, 130, 140, 141, 150, 160, 170, 180, 190, or 200, 220, 240, 260, 280, 300, 320, 340, 360, 380, 400, 420, 424, 440, 460, 480, 500, 550, 600, 650, 700, 727, 750, 800, 850, 900, 950, or 1000 of the TN1 and/or N2 segments of any of the theoretical segment pools provided herein, or generated by the methods described herein, are included in a library. In certain embodiments, a library of the invention may contain less than a particular number of polynucleotide or polypeptide segments, where the number of segments is defined using any one of the integers provided above for the respective segment. In some embodiments of the invention, a particular numerical range is defined, using any two of the integers provided above as lower and upper boundaries of the range, inclusive or exclusive. All combinations of the integers provided, which define an upper and lower boundary, are contemplated.

In certain embodiments, the invention provides CDRH3 libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the segments from any of the theoretical segment pools provided herein. For example, the invention provides libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the TN1, DH, N2, and/or H3-JH segments from any of the theoretical segment pools provided herein. In some embodiments of the invention, a particular percentage range is defined, using any two of the percentages provided above as lower and upper boundaries of the range, inclusive or exclusive. All combinations of the percentages provided, which define an upper and lower boundary, are contemplated.

In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the H3-JH, DH, TN1, and/or N2 segments in a CDRH3 library are H3-JH, DH, TN1, and/or N2 segments of any of the theoretical segment pools provided herein, or generated by the methods described herein. In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the H3-JH, DH, TN1, and/or N2 segments of antibodies isolated from a CDRH3 library (e.g., by binding to a particular antigen and/or generic ligand through one or more rounds of selection) are H3-JH, DH, TN1, and/or N2 segments of any of the theoretical segment pools provided herein, or generated by methods described herein. In certain embodiments, a CDRH3 library of the invention may contain less than a particular percentage of H3-JH, DH, TN1, and/or N2 segments of any of the theoretical segment pools provided herein, or generated by the methods described herein, where the number of segments is defined using any one of the percentages provided above for the respective segment. In some embodiments of the invention, a particular percentage range is defined, using any two of the percentages provided above as lower and upper boundaries of the range, inclusive or exclusive. All combinations of the percentages provided, which define an upper and lower boundary, are contemplated.

One of ordinary skill in the art will appreciate, upon reading the disclosure herein, that given the TN1, DH, N2, and/or H3-JH segments of any of the theoretical segment pools provided herein, or generated by the methods described herein, similar TN1, DH, N2, and/or H3-JH segments, and corresponding CDRH3 libraries, could be produced which, while not 100% identical to those provided in terms of their sequences, may be functionally very similar. Such theoretical segment pools and CDRH3 libraries also fall within the scope of the invention. A variety of techniques well-known in the art could be used to obtain these additional sequences, including the mutagenesis techniques provided herein. Therefore, each of the explicitly enumerated embodiments of the invention can also be practiced using segments that share a particular percent identity to any of the segments of any of the theoretical segment pools provided herein, or generated by the methods described herein. For example, each of the previously described embodiments of the invention can be practiced using TN1, DH, N2, and/or H3-JH segments that are at least about 50%, 55%, 60%, 65%, 70%, 75%, 80%, 85%, 90%, 91%, 92%, 93%, 94%, 95%, 96%, 97%, 98%, 99%, 99.5%, or 99.9% identical to the TN1, DH, N2, and/or H3-JH segments of any of the theoretical segment pools provided herein, or generated by the methods described herein.

In some embodiments, the invention provides libraries produced from one or more VH chassis sequences combined with one or more TN1 segments, one or more DH segments, one or more N2 segments, and one or more H3-JH segments. In certain embodiments at least 1, 2, 5, 10, 20, 50, 75, or 100, of each chassis, TN1, DH, N2, or H3-JH segments are included in a library of the invention.

In some embodiments, the invention provides a method of selecting TN1, DH, N2, and H3-JH segments from a theoretical segment pool for inclusion in a synthetic CDRH3 library, comprising:
(i) providing a theoretical segment pool containing one or more of TN1, DH, N2, and H3-JH segments;
(ii) providing a reference set of CDRH3 sequences;
(iii) utilizing the theoretical segment pool of (i) to identify the closest match(es) to each CDRH3 sequence in the reference set of (ii); and
(iv) selecting segments from the theoretical segment pool for inclusion in a synthetic library.

In some embodiments, the selection process of (iv) can optionally involve any number of additional criteria, including the frequency of occurrence of the segments of (i) in the reference set of (ii); the corresponding segmental usage weights; and any physicochemical properties (see all numerical indices on the world wide web at genome.jp/aaindex/) of the segments (e.g., hydrophobicity, alpha-helical propensity, and/or isoelectric point). Optionally, TN1 and/or N2 segments that do not occur in the theoretical segment pool of (i) but that are found in the reference set of (ii) may be identified and added to prospective theoretical segment pools to produce theoretical segment pools with increased TN1 and/or N2 diversity in the prospective theoretical segment pools and/or synthetic libraries of the invention.

Any characteristic or set of characteristics of the segments can be used to choose them for inclusion in the library, including for example one or more biological properties (e.g., immunogenicity, stability, half-life) and/or one or more physicochemical properties such as the numerical indices provided above. In some embodiments, at least 1, 2, 3, 4, 5, 6, 7, 8, 9, 10, 11, 12, 13, 14, 15 or more such properties is used to select segments for inclusion in a library of the invention. Physiochemical properties included in the index provided above can include, for example, ANDN920101 alpha-CH chemical shifts (Andersen et al., 1992); ARGP820101 Hydrophobicity index (Argos et al., 1982); ARGP820102 Signal sequence helical potential (Argos et al., 1982); ARGP820103 Membrane-buried preference parameters (Argos et al., 1982); BEGF750101 Conformational parameter of inner helix (Beghin-Dirkx, 1975); BEGF750102 Conformational parameter of beta-structure (Beghin-Dirkx, 1975); BEGF750103 Conformational parameter of beta-turn (Beghin-Dirkx, 1975); BHAR880101 Average flexibility indices (Bhaskaran-Ponnuswamy, 1988); BIGC670101 Residue volume (Bigelow, 1967); BIOV880101 Information value for accessibility; average fraction 35% (Biou et al., 1988); BIOV880102 Information value for accessibility; average fraction 23% (Biou et al., 1988); BROC820101 Retention coefficient in TFA (Browne et al., 1982); BROC820102 Retention coefficient in HFBA (Browne et al., 1982); BULH740101 Transfer free energy to surface (Bull-Breese, 1974); BULH740102 Apparent partial specific volume (Bull-Breese, 1974); BUNA790101 alpha-NH chemical shifts (Bundi-Wuthrich, 1979); BUNA790102 alpha-CH chemical shifts (Bundi-Wuthrich, 1979); BUNA790103 Spin-spin coupling constants 3JHalpha-NH (Bundi-Wuthrich, 1979); BURA740101 Normalized frequency of alpha-helix (Burgess et al., 1974); BURA740102 Normalized frequency of extended structure (Burgess et al., 1974); CHAM810101 Steric parameter (Charton, 1981); CHAM820101 Polarizability parameter (Charton-Charton, 1982); CHAM820102 Free energy of solution in water, kcal/mole (Charton-Charton, 1982); CHAM830101 The Chou-Fasman parameter of the coil conformation (Charton-Charton, 1983); CHAM830102 A parameter defined from the residuals obtained from the best correlation of the Chou-Fasman parameter of beta-sheet (Charton-Charton, 1983); CHAM830103 The number of atoms in the side chain labelled 1+1 (Charton-Charton, 1983); CHAM830104 The number of atoms in the side chain labelled 2+1 (Charton-Charton, 1983); CHAM830105 The number of atoms in the side chain labelled 3+1 (Charton-Charton, 1983); CHAM830106 The number of bonds in the longest chain (Charton-Charton, 1983); CHAM830107 A parameter of charge transfer capability (Charton-Charton, 1983); CHAM830108 A parameter of charge transfer donor capability (Charton-Charton, 1983); CHOC750101 Average volume of buried residue (Chothia, 1975); CHOC760101 Residue accessible surface area in tripeptide (Chothia, 1976); CHOC760102 Residue accessible surface area in folded protein (Chothia, 1976); CHOC760103 Proportion of residues 95% buried (Chothia, 1976); CHOC760104 Proportion of residues 100% buried (Chothia, 1976); CHOP780101 Normalized frequency of beta-turn (Chou-Fasman, 1978a); CHOP780201 Normalized frequency of alpha-helix (Chou-Fasman, 1978b); CHOP780202 Normalized frequency of beta-sheet (Chou-Fasman, 1978b); CHOP780203 Normalized frequency of beta-turn (Chou-Fasman, 1978b); CHOP780204 Normalized frequency of N-terminal helix (Chou-Fasman, 1978b); CHOP780205 Normalized frequency of C-terminal helix (Chou-Fasman, 1978b); CHOP780206 Normalized frequency of N-terminal non helical region (Chou-Fasman, 1978b); CHOP780207 Normalized frequency of C-terminal non helical region (Chou-Fasman, 1978b); CHOP780208 Normalized frequency of N-terminal beta-sheet (Chou-Fasman, 1978b); CHOP780209 Normalized frequency of C-terminal beta-sheet (Chou-Fasman, 1978b); CHOP780210 Normalized frequency of N-terminal non beta region (Chou-Fasman, 1978b); CHOP780211 Normalized frequency of C-terminal non beta region (Chou-Fasman, 1978b); CHOP780212 Frequency of the 1st residue in turn (Chou-Fasman, 1978b); CHOP780213 Frequency of the 2nd residue in turn (Chou-Fasman, 1978b); CHOP780214 Frequency of the 3rd residue in turn (Chou-Fasman, 1978b); CHOP780215 Frequency of the 4th residue in turn (Chou-Fasman, 1978b);

CHOP780216 Normalized frequency of the 2nd and 3rd residues in turn (Chou-Fasman, 1978b); CIDH920101 Normalized hydrophobicity scales for alpha-proteins (Cid et al., 1992); CIDH920102 Normalized hydrophobicity scales for beta-proteins (Cid et al., 1992); CIDH920103 Normalized hydrophobicity scales for alpha+beta-proteins (Cid et al., 1992); CIDH920104 Normalized hydrophobicity scales for alpha/beta-proteins (Cid et al., 1992); CIDH920105 Normalized average hydrophobicity scales (Cid et al., 1992); COHE430101 Partial specific volume (Cohn-Edsall, 1943); CRAJ730101 Normalized frequency of middle helix (Crawford et al., 1973); CRAJ730102 Normalized frequency of beta-sheet (Crawford et al., 1973); CRAJ730103 Normalized frequency of turn (Crawford et al., 1973); DAWD720101 Size (Dawson, 1972); DAYM780101 Amino acid composition (Dayhoff et al., 1978a); DAYM780201 Relative mutability (Dayhoff et al., 1978b); DESM900101 Membrane preference for cytochrome b: MPH89 (Degli Esposti et al., 1990); DESM900102 Average membrane preference: AMP07 (Degli Esposti et al., 1990); EISD840101 Consensus normalized hydrophobicity scale (Eisenberg, 1984); EISD860101 Solvation free energy (Eisenberg-McLachlan, 1986); EISD860102 Atom-based hydrophobic moment (Eisenberg-McLachlan, 1986); EISD860103 Direction of hydrophobic moment (Eisenberg-McLachlan, 1986); FASG760101 Molecular weight (Fasman, 1976); FASG760102 Melting point (Fasman, 1976); FASG760103 Optical rotation (Fasman, 1976); FASG760104 pK-N (Fasman, 1976); FASG760105 pK-C (Fasman, 1976); FAUJ830101 Hydrophobic parameter pi (Fauchere-Pliska, 1983); FAUJ880101 Graph shape index (Fauchere et al., 1988); FAUJ880102 Smoothed upsilon steric parameter (Fauchere et al., 1988); FAUJ880103 Normalized van der Waals volume (Fauchere et al., 1988); FAUJ880104 STERIMOL length of the side chain (Fauchere et al., 1988); FAUJ880105 STERIMOL minimum width of the side chain (Fauchere et al., 1988); FAUJ880106 STERIMOL maximum width of the side chain (Fauchere et al., 1988); FAUJ880107 N.m.r. chemical shift of alpha-carbon (Fauchere et al., 1988); FAUJ880108 Localized electrical effect (Fauchere et al., 1988); FAUJ880109 Number of hydrogen bond donors (Fauchere et al., 1988); FAUJ880110 Number of full nonbonding orbitals (Fauchere et al., 1988); FAUJ880111 Positive charge (Fauchere et al., 1988); FAUJ880112 Negative charge (Fauchere et al., 1988); FAUJ880113 pK-a(RCOOH) (Fauchere et al., 1988); FINA770101 Helix-coil equilibrium constant (Finkelstein-Ptitsyn, 1977); FINA910101 Helix initiation parameter at posision i–1 (Finkelstein et al., 1991); FINA910102 Helix initiation parameter at posision 0+0+2 (Finkelstein et al., 1991); FINA910103 Helix termination parameter at posision j–2,j–1,j (Finkelstein et al., 1991); FINA910104 Helix termination parameter at posision j+1 (Finkelstein et al., 1991); GARJ730101 Partition coefficient (Garel et al., 1973); GEIM800101 Alpha-helix indices (Geisow-Roberts, 1980); GEIM800102 Alpha-helix indices for alpha-proteins (Geisow-Roberts, 1980); GEIM800103 Alpha-helix indices for beta-proteins (Geisow-Roberts, 1980); GEIM800104 Alpha-helix indices for alpha/beta-proteins (Geisow-Roberts, 1980); GEIM800105 Beta-strand indices (Geisow-Roberts, 1980); GEIM800106 Beta-strand indices for beta-proteins (Geisow-Roberts, 1980); GEIM800107 Beta-strand indices for alpha/beta-proteins (Geisow-Roberts, 1980) GEIM800108 Aperiodic indices (Geisow-Roberts, 1980); GEI M800109 Aperiodic indices for alpha-proteins (Geisow-Roberts, 1980); GEIM800110 Aperiodic indices for beta-proteins (Geisow-Roberts, 1980); GEIM800111 Aperiodic indices for alpha/beta-proteins (Geisow-Roberts, 1980); GOLD730101 Hydrophobicity factor (Goldsack-Chalifoux, 1973); GOLD730102 Residue volume (Goldsack-Chalifoux, 1973); GRAR740101 Composition (Grantham, 1974); GRAR740102 Polarity (Grantham, 1974) GRAR740103 Volume (Grantham, 1974); GUYH850101 Partition energy (Guy, 1985); HOPA770101 Hydration number (Hopfinger, 1971), Cited by Charton-Charton (1982) HOPT810101 Hydrophilicity value (Hopp-Woods, 1981); HUTJ700101 Heat capacity (Hutchens, 1970); HUTJ700102 Absolute entropy (Hutchens, 1970); HUTJ700103 Entropy of formation (Hutchens, 1970); ISOY800101 Normalized relative frequency of alpha-helix (Isogai et al., 1980); ISOY800102 Normalized relative frequency of extended structure (Isogai et al., 1980); ISOY800103 Normalized relative frequency of bend (Isogai et al., 1980); ISOY800104 Normalized relative frequency of bend R (Isogai et al., 1980); ISOY800105 Normalized relative frequency of bend S (Isogai et al., 1980); ISOY800106 Normalized relative frequency of helix end (Isogai et al., 1980); ISOY800107 Normalized relative frequency of double bend (Isogai et al., 1980); ISOY800108 Normalized relative frequency of coil (Isogai et al., 1980); JANJ780101 Average accessible surface area (Janin et al., 1978); JANJ780102 Percentage of buried residues (Janin et al., 1978); JANJ780103 Percentage of exposed residues (Janin et al., 1978); JANJ790101 Ratio of buried and accessible molar fractions (Janin, 1979); JANJ790102 Transfer free energy (Janin, 1979); JOND750101 Hydrophobicity (Jones, 1975); JOND750102 pK (—COOH) (Jones, 1975); JOND920101 Relative frequency of occurrence (Jones et al., 1992); JOND920102 Relative mutability (Jones et al., 1992)
JUKT750101 Amino acid distribution (Jukes et al., 1975); JUNJ780101 Sequence frequency (Jungck, 1978); KANM800101 Average relative probability of helix (Kanehisa-Tsong, 1980); KANM800102 Average relative probability of beta-sheet (Kanehisa-Tsong, 1980); KANM800103 Average relative probability of inner helix (Kanehisa-Tsong, 1980); KANM800104 Average relative probability of inner beta-sheet (Kanehisa-Tsong, 1980); KARP850101 Flexibility parameter for no rigid neighbors (Karplus-Schulz, 1985); KARP850102 Flexibility parameter for one rigid neighbor (Karplus-Schulz, 1985); KARP850103 Flexibility parameter for two rigid neighbors (Karplus-Schulz, 1985); KHAG800101 The Kerr-constant increments (Khanarian-Moore, 1980); KLEP840101 Net charge (Klein et al., 1984); KRIW710101 Side chain interaction parameter (Krigbaum-Rubin, 1971); KRIW790101 Side chain interaction parameter (Krigbaum-Komoriya, 1979); KRIW790102 Fraction of site occupied by water (Krigbaum-Komoriya, 1979); KRIW790103 Side chain volume (Krigbaum-Komoriya, 1979); KYTJ820101 Hydropathy index (Kyte-Doolittle, 1982); LAWE840101 Transfer free energy, CHP/water (Lawson et al., 1984); LEVM760101 Hydrophobic parameter (Levitt, 1976); LEVM760102 Distance between C-alpha and centroid of side chain (Levitt, 1976); LEVM760103 Side chain angle theta(AAR) (Levitt, 1976); LEVM760104 Side chain torsion angle phi(AAAR) (Levitt, 1976); LEVM760105 Radius of gyration of side chain (Levitt, 1976); LEVM760106 van der Waals parameter RO (Levitt, 1976)
LEVM760107 van der Waals parameter epsilon (Levitt, 1976); LEVM780101 Normalized frequency of alpha-helix, with weights (Levitt, 1978); LEVM780102 Normalized frequency of beta-sheet, with weights (Levitt, 1978); LEVM780103 Normalized frequency of reverse turn, with weights (Levitt, 1978); LEVM780104 Normalized frequency of alpha-helix, unweighted (Levitt, 1978); LEVM780105 Normalized frequency of beta-sheet, unweighted (Levitt, 1978); LEVM780106 Normalized frequency of reverse turn, unweighted (Levitt, 1978); LEWP710101 Frequency of occurrence in beta-bends (Lewis et al., 1971); LIFS790101 Conformational preference for all beta-strands (Lifson-Sander, 1979); LIFS790102 Conformational preference for parallel beta-strands (Lifson-Sander, 1979); LIFS790103 Conformational preference for antiparallel beta-strands (Lifson-Sander, 1979); MANP780101 Average surrounding hydrophobicity (Manavalan-Ponnuswamy, 1978); MAXF760101 Normalized frequency of alpha-helix (Maxfield-Scheraga, 1976); MAXF760102 Normalized frequency of extended structure (Maxfield-Scheraga, 1976); MAXF760103 Normalized frequency of zeta R (Maxfield-Scheraga, 1976); MAXF760104 Normalized frequency of left-handed alpha-helix (Maxfield-Scheraga, 1976); MAXF760105 Normalized frequency of zeta L (Maxfield-Scheraga, 1976); MAXF760106 Normalized frequency of alpha region (Maxfield-Scheraga, 1976); MCMT640101 Refractivity (McMeekin et al., 1964), Cited by Jones (1975); MEEJ800101 Retention coefficient in HPLC, pH7.4 (Meek, 1980); MEEJ800102 Retention coefficient in HPLC, pH2.1 (Meek, 1980); MEEJ810101 Retention coefficient in NaClO4 (Meek-Rossetti, 1981); MEEJ810102 Retention coefficient in NaH2PO4 (Meek-Rossetti, 1981); MEIH800101 Average reduced distance for C-alpha (Meirovitch et al., 1980); MEIH800102 Average reduced distance for side chain (Meirovitch et al., 1980); MEIH800103 Average side chain orientation angle (Meirovitch et al., 1980); MIYS850101 Effective partition energy (Miyazawa-Jernigan, 1985); NAGK730101 Normalized frequency of alpha-helix (Nagano, 1973); NAGK730102 Normalized frequency of bata-structure (Nagano, 1973)

NAGK730103 Normalized frequency of coil (Nagano, 1973); NAKH900101 AA composition of total proteins (Nakashima et al., 1990); NAKH900102 SD of AA composition of total proteins (Nakashima et al., 1990); NAKH900103 AA composition of mt-proteins (Nakashima et al., 1990); NAKH900104 Normalized composition of mt-proteins (Nakashima et al., 1990); NAKH900105 AA composition of mt-proteins from animal (Nakashima et al., 1990); NAKH900106 Normalized composition from animal (Nakashima et al., 1990); NAKH900107 AA composition of mt-proteins from fungi and plant (Nakashima et al., 1990); NAKH900108 Normalized composition from fungi and plant (Nakashima et al., 1990); NAKH900109 AA composition of membrane proteins (Nakashima et al., 1990); NAKH900110 Normalized composition of membrane proteins (Nakashima et al., 1990); NAKH900111 Transmembrane regions of non-mt-proteins (Nakashima et al., 1990); NAKH900112 Transmembrane regions of mt-proteins (Nakashima et al., 1990); NAKH900113 Ratio of average and computed composition (Nakashima et al., 1990); NAKH920101 AA composition of CYT of single-spanning proteins (Nakashima-Nishikawa, 1992); NAKH920102 AA composition of CYT2 of single-spanning proteins (Nakashima-Nishikawa, 1992); NAKH920103 AA composition of EXT of single-spanning proteins (Nakashima-Nishikawa, 1992); NAKH920104 AA composition of EXT2 of single-spanning proteins (Nakashima-Nishikawa, 1992); NAKH920105 AA composition of MEM of single-spanning proteins (Nakashima-Nishikawa, 1992); NAKH920106 AA composition of CYT of multi-spanning proteins (Nakashima-Nishikawa, 1992); NAKH920107 AA composition of EXT of multi-spanning proteins (Nakashima-Nishikawa, 1992); NAKH920108 AA composition of MEM of multi-spanning proteins (Nakashima-Nishikawa, 1992); NISK800101 8 A contact number (Nishikawa-Ooi, 1980); NISK860101 14 A contact number (Nishikawa-Ooi, 1986); NOZY710101 Transfer energy, organic solvent/water (Nozaki-Tanford, 1971); OOBM770101 Average non-bonded energy per atom (Oobatake-Ooi, 1977); OOBM770102 Short and medium range non-bonded energy per atom (Oobatake-Ooi, 1977); OOBM770103 Long range non-bonded energy per atom (Oobatake-Ooi, 1977)

OOBM770104 Average non-bonded energy per residue (Oobatake-Ooi, 1977); OOBM770105 Short and medium range non-bonded energy per residue (Oobatake-Ooi, 1977); OOBM850101 Optimized beta-structure-coil equilibrium constant (Oobatake et al., 1985); OOBM850102 Optimized propensity to form reverse turn (Oobatake et al., 1985); OOBM850103 Optimized transfer energy parameter (Oobatake et al., 1985); OOBM850104 Optimized average non-bonded energy per atom (Oobatake et al., 1985); OOBM850105 Optimized side chain interaction parameter (Oobatake et al., 1985); PALJ810101 Normalized frequency of alpha-helix from LG (Palau et al., 1981); PALJ810102 Normalized frequency of alpha-helix from CF (Palau et al., 1981); PALJ810103 Normalized frequency of beta-sheet from LG (Palau et al., 1981); PALJ810104 Normalized frequency of beta-sheet from CF (Palau et al., 1981); PALJ810105 Normalized frequency of turn from LG (Palau et al., 1981); PALJ810106 Normalized frequency of turn from CF (Palau et al., 1981); PALJ810107 Normalized frequency of alpha-helix in all-alpha class (Palau et al., 1981); PALJ810108 Normalized frequency of alpha-helix in alpha+beta class (Palau et al., 1981); PALJ810109 Normalized frequency of alpha-helix in alpha/beta class (Palau et al., 1981); PALJ810110 Normalized frequency of beta-sheet in all-beta class (Palau et al., 1981); PALJ810111 Normalized frequency of beta-sheet in alpha+beta class (Palau et al., 1981); PALJ810112 Normalized frequency of beta-sheet in alpha/beta class (Palau et al., 1981); PALJ810113 Normalized frequency of turn in all-alpha class (Palau et al., 1981); PALJ810114 Normalized frequency of turn in all-beta class (Palau et al., 1981); PALJ810115 Normalized frequency of turn in alpha+beta class (Palau et al., 1981); PALJ810116 Normalized frequency of turn in alpha/beta class (Palau et al., 1981); PARJ860101 HPLC parameter (Parker et al., 1986); PLIV810101 Partition coefficient (Pliska et al., 1981); PONP800101 Surrounding hydrophobicity in folded form (Ponnuswamy et al., 1980); PONP800102 Average gain in surrounding hydrophobicity (Ponnuswamy et al., 1980); PONP800103 Average gain ratio in surrounding hydrophobicity (Ponnuswamy et al., 1980); PONP800104 Surrounding hydrophobicity in alpha-helix (Ponnuswamy et al., 1980); PONP800105 Surrounding hydrophobicity in beta-sheet (Ponnuswamy et al., 1980); PONP800106 Surrounding hydrophobicity in turn (Ponnuswamy et al., 1980); PONP800107 Accessibility reduction ratio (Ponnuswamy et al., 1980); PONP800108 Average number of surrounding residues (Ponnuswamy et al., 1980); PRAM820101 Intercept in regression analysis (Prabhakaran-Ponnuswamy, 1982); PRAM820102 Slope in regression analysis×1.0E1 (Prabhakaran-Ponnuswamy, 1982); PRAM820103 Correlation coefficient in regression analysis (Prabhakaran-Ponnuswamy, 1982); PRAM900101 Hydrophobicity (Prabhakaran, 1990); PRAM900102 Relative frequency in alpha-helix (Prabhakaran, 1990); PRAM900103 Relative frequency in beta-sheet (Prabhakaran, 1990); PRAM900104 Relative frequency in reverse-turn (Prabhakaran, 1990); PTI0830101 Helix-coil equilibrium constant (Ptitsyn-Finkelstein, 1983);

PTI0830102 Beta-coil equilibrium constant (Ptitsyn-Finkelstein, 1983); QIAN880101 Weights for alpha-helix at the window position of −6 (Qian-Sejnowski, 1988); QIAN880102 Weights for alpha-helix at the window position of −5 (Qian-Sejnowski, 1988); QIAN880103 Weights for alpha-helix at the window position of −4 (Qian-Sejnowski, 1988); QIAN880104 Weights for alpha-helix at the window position of −3 (Qian-Sejnowski, 1988); QIAN880105 Weights for alpha-helix at the window position of −2 (Qian-Sejnowski, 1988); QIAN880106 Weights for alpha-helix at the window position of −1 (Qian-Sejnowski, 1988); QIAN880107 Weights for alpha-helix at the window position of 0 (Qian-Sejnowski, 1988); QIAN880108 Weights for alpha-helix at the window position of 1 (Qian-Sejnowski, 1988); QIAN880109 Weights for alpha-helix at the window position of 2 (Qian-Sejnowski, 1988); QIAN880110 Weights for alpha-helix at the window position of 3 (Qian-Sejnowski, 1988); QIAN880111 Weights for alpha-helix at the window position of 4 (Qian-Sejnowski, 1988); QIAN880112 Weights for alpha-helix at the window position of 5 (Qian-Sejnowski, 1988); QIAN880113 Weights for alpha-helix at the window position of 6 (Qian-Sejnowski, 1988); QIAN880114 Weights for beta-sheet at the window position of −6 (Qian-Sejnowski, 1988); QIAN880115 Weights for beta-sheet at the window position of −5 (Qian-Sejnowski, 1988); QIAN880116 Weights for beta-sheet at the window position of −4 (Qian-Sejnowski, 1988); QIAN880117 Weights for beta-sheet at the window position of −3 (Qian-Sejnowski, 1988); QIAN880118 Weights for beta-sheet at the window position of −2 (Qian-Sejnowski, 1988); QIAN880119 Weights for beta-sheet at the window position of −1 (Qian-Sejnowski, 1988); QIAN880120 Weights for beta-sheet at the window position of 0 (Qian-Sejnowski, 1988); QIAN880121 Weights for beta-sheet at the window position of 1 (Qian-Sejnowski, 1988); QIAN880122 Weights for beta-sheet at the window position of 2 (Qian-Sejnowski, 1988); QIAN880123 Weights for beta-sheet at the window position of 3 (Qian-Sejnowski, 1988); QIAN880124 Weights for beta-sheet at the window position of 4 (Qian-Sejnowski, 1988); QIAN880125 Weights for beta-sheet at the window position of 5 (Qian-Sejnowski, 1988); QIAN880126 Weights for beta-sheet at the window position of 6 (Qian-Sejnowski, 1988); QIAN880127 Weights for coil at the window position of −6 (Qian-Sejnowski, 1988); QIAN880128 Weights for coil at the window position of −5 (Qian-Sejnowski, 1988); QIAN880129 Weights for coil at the window position of −4 (Qian-Sejnowski, 1988); QIAN880130 Weights for coil at the window position of −3 (Qian-Sejnowski, 1988); QIAN880131 Weights for coil at the window position of −2 (Qian-Sejnowski, 1988); QIAN880132 Weights for coil at the window position of −1 (Qian-Sejnowski, 1988); QIAN880133 Weights for coil at the window position of 0 (Qian-Sejnowski, 1988); QIAN880134 Weights for coil at the window position of 1 (Qian-Sejnowski, 1988); QIAN880135 Weights for coil at the window position of 2 (Qian-Sejnowski, 1988); QIAN880136 Weights for coil at the window position of 3 (Qian-Sejnowski, 1988); QIAN880137 Weights for coil at the window position of 4 (Qian-Sejnowski, 1988); QIAN880138 Weights for coil at the window position of 5 (Qian-Sejnowski, 1988); QIAN880139 Weights for coil at the window position of 6 (Qian-Sejnowski, 1988); RACS770101 Average reduced distance for C-alpha (Rackovsky-Scheraga, 1977); RACS770102 Average reduced distance for side chain (Rackovsky-Scheraga, 1977); RACS770103 Side chain orientational preference (Rackovsky-Scheraga, 1977); RACS820101 Average relative fractional occurrence in A0(i) (Rackovsky-Scheraga, 1982); RACS820102 Average relative fractional occurrence in AR(i) (Rackovsky-Scheraga, 1982); RACS820103 Average relative fractional occurrence in AL(i) (Rackovsky-Scheraga, 1982); RACS820104 Average relative fractional occurrence in EL(i) (Rackovsky-Scheraga, 1982); RACS820105 Average relative fractional occurrence in E0(i) (Rackovsky-Scheraga, 1982); RACS820106 Average relative fractional occurrence in ER(i) (Rackovsky-Scheraga, 1982); RACS820107 Average relative fractional occurrence in A0(i-1) (Rackovsky-Scheraga, 1982); RACS820108 Average relative fractional occurrence in AR(i-1) (Rackovsky-Scheraga, 1982); RACS820109 Average relative fractional occurrence in AL(i-1) (Rackovsky-Scheraga, 1982); RACS820110 Average relative fractional occurrence in EL(i-1) (Rackovsky-Scheraga, 1982); RACS820111 Average relative fractional occurrence in E0(i-1) (Rackovsky-Scheraga, 1982); RACS820112 Average relative fractional occurrence in ER(i-1) (Rackovsky-Scheraga, 1982); RACS820113 Value of theta(i) (Rackovsky-Scheraga, 1982); RACS820114 Value of theta(i-1) (Rackovsky-Scheraga, 1982); RADA880101 Transfer free energy from chx to wat (Radzicka-Wolfenden, 1988); RADA880102 Transfer free energy from oct to wat (Radzicka-Wolfenden, 1988); RADA880103 Transfer free energy from yap to chx (Radzicka-Wolfenden, 1988); RADA880104 Transfer free energy from chx to oct (Radzicka-Wolfenden, 1988); RADA880105 Transfer free energy from yap to oct (Radzicka-Wolfenden, 1988); RADA880106 Accessible surface area (Radzicka-Wolfenden, 1988); RADA880107 Energy transfer from out to in (95% buried) (Radzicka-Wolfenden, 1988); RADA880108 Mean polarity (Radzicka-Wolfenden, 1988); RICJ880101 Relative preference value at N" (Richardson-Richardson, 1988); RICJ880102 Relative preference value at N' (Richardson-Richardson, 1988); RICJ880103 Relative preference value at N-cap (Richardson-Richardson, 1988); RICJ880104 Relative preference value at N1 (Richardson-Richardson, 1988); RICJ880105 Relative preference value at N2 (Richardson-Richardson, 1988); RICJ880106 Relative preference value at N3 (Richardson-Richardson, 1988); RICJ880107 Relative preference value at N4 (Richardson-Richardson, 1988); RICJ880108 Relative preference value at N5 (Richardson-Richardson, 1988); RICJ880109 Relative preference value at Mid (Richardson-Richardson, 1988); RICJ880110 Relative preference value at C5 (Richardson-Richardson, 1988); RICJ880111 Relative preference value at C4 (Richardson-Richardson, 1988); RICJ880112 Relative preference value at C3 (Richardson-Richardson, 1988); RICJ880113 Relative preference value at C2 (Richardson-Richardson, 1988); RICJ880114 Relative preference value at C1 (Richardson-Richardson, 1988); RICJ880115 Relative preference value at C-cap (Richardson-Richardson, 1988); RICJ880116 Relative preference value at C' (Richardson-Richardson, 1988); RICJ880117 Relative preference value at C" (Richardson-Richardson, 1988); ROBB760101 Information measure for alpha-helix (Robson-Suzuki, 1976); ROBB760102 Information measure for N-terminal helix (Robson-Suzuki, 1976); ROBB760103 Information measure for middle helix (Robson-Suzuki, 1976); ROBB760104 Information measure for C-terminal helix (Robson-Suzuki, 1976); ROBB760105 Information measure for extended (Robson-Suzuki, 1976); ROBB760106 Information measure for pleated-sheet (Robson-Suzuki, 1976); ROBB760107 Information measure for extended without H-bond (Robson-Suzuki, 1976); ROBB760108 Information measure for turn (Robson-Suzuki, 1976); ROBB760109 Information measure for N-terminal turn (Robson-Suzuki, 1976); ROBB760110 Information measure for middle turn (Robson-Suzuki, 1976); ROBB760111 Information measure for C-terminal turn (Robson-Suzuki, 1976); ROBB760112 Information measure for coil (Robson-Suzuki, 1976); ROBB760113 Information measure for loop (Robson-Suzuki, 1976); ROBB790101 Hydration free energy (Robson-Osguthorpe, 1979); ROSG850101 Mean area buried on transfer (Rose et al., 1985); ROSG850102 Mean fractional area loss (Rose et al., 1985); ROSM880101 Side chain hydropathy, uncorrected for solvation (Roseman, 1988); ROSM880102 Side chain hydropathy, corrected for solvation (Roseman, 1988); ROSM880103 Loss of Side chain hydropathy by helix formation (Roseman, 1988); SIMZ760101 Transfer free energy (Simon, 1976), Cited by Charton-Charton (1982); SNEP660101 Principal component I (Sneath, 1966); SNEP660102 Principal component II (Sneath, 1966); SNEP660103 Principal component III (Sneath, 1966); SNEP660104 Principal component IV (Sneath, 1966); SUEM840101 Zimm-Bragg parameter s at 20 C (Sueki et al., 1984); SUEM840102 Zimm-Bragg parameter sigma× 1.0E4 (Sueki et al., 1984); SWER830101 Optimal matching hydrophobicity (Sweet-Eisenberg, 1983); TANS770101 Normalized frequency of alpha-helix (Tanaka-Scheraga, 1977); TANS770102 Normalized frequency of isolated helix (Tanaka-Scheraga, 1977); TANS770103 Normalized frequency of extended structure (Tanaka-Scheraga, 1977); TANS770104 Normalized frequency of chain reversal R (Tanaka-Scheraga, 1977); TANS770105 Normalized frequency of chain reversal S (Tanaka-Scheraga, 1977); TANS770106 Normalized frequency of chain reversal D (Tanaka-Scheraga, 1977); TANS770107 Normalized frequency of left-handed helix (Tanaka-Scheraga, 1977); TANS770108 Normalized frequency of zeta R (Tanaka-Scheraga, 1977); TANS770109 Normalized frequency of coil (Tanaka-Scheraga, 1977) TANS770110 Normalized frequency of chain reversal (Tanaka-Scheraga, 1977); VASM830101 Relative population of conformational state A (Vasquez et al., 1983); VASM830102 Relative population of conformational state C (Vasquez et al., 1983); VASM830103 Relative population of conformational state E (Vasquez et al., 1983); VELV850101 Electron-ion interaction potential (Veljkovic et al., 1985); VENT840101 Bitterness (Venanzi, 1984); VHEG790101 Transfer free energy to lipophilic phase (von Heijne-Blomberg, 1979); WARP780101 Average interactions per side chain atom (Warme-Morgan, 1978); WEBA780101 RF value in high salt chromatography (Weber-Lacey, 1978); WERD780101 Propensity to be buried inside (Wertz-Scheraga, 1978); WERD780102 Free energy change of epsilon(i) to epsilon (ex) (Wertz-Scheraga, 1978); WERD780103 Free energy change of alpha(Ri) to alpha(Rh) (Wertz-Scheraga, 1978); WERD780104 Free energy change of epsilon(i) to alpha (Rh) (Wertz-Scheraga, 1978); WOEC730101 Polar requirement (Woese, 1973); WOLR810101 Hydration potential (Wolfenden et al., 1981); WOLS870101 Principal property value z1 (Wold et al., 1987); WOLS870102 Principal property value z2 (Wold et al., 1987); WOLS870103 Principal property value z3 (Wold et al., 1987); YUTK870101 Unfolding Gibbs energy in water, pH7.0 (Yutani et al., 1987); YUTK870102 Unfolding Gibbs energy in water, pH9.0 (Yutani et al., 1987); YUTK870103 Activation Gibbs energy of unfolding, pH7.0 (Yutani et al., 1987); YUTK870104 Activation Gibbs energy of unfolding, pH9.0 (Yutani et al., 1987); ZASB820101 Dependence of partition coefficient on ionic strength (Zaslaysky et al., 1982); ZIMJ680101 Hydrophobicity (Zimmerman et al., 1968); ZIMJ680102 Bulkiness (Zimmerman et al., 1968); ZIMJ680103 Polarity (Zimmerman et al., 1968); ZIMJ680104 Isoelectric point (Zimmerman et al., 1968); ZIMJ680105 RF rank (Zimmerman et al., 1968); AURR980101 Normalized positional residue frequency at helix termini N4'(Aurora-Rose, 1998); AURR980102 Normalized positional residue frequency at helix termini N''' (Aurora-Rose, 1998); AURR980103 Normalized positional residue frequency at helix termini N" (Aurora-Rose, 1998); AURR980104 Normalized positional residue frequency at helix termini N'(Aurora-Rose, 1998); AURR980105 Normalized positional residue frequency at helix termini Nc (Aurora-Rose, 1998); AURR980106 Normalized positional residue frequency at helix termini N1 (Aurora-Rose, 1998); AURR980107 Normalized positional residue frequency at helix termini N2 (Aurora-Rose, 1998); AURR980108 Normalized positional residue frequency at helix termini N3 (Aurora-Rose, 1998); AURR980109 Normalized positional residue frequency at helix termini N4 (Aurora-Rose, 1998); AURR980110 Normalized positional residue frequency at helix termini N5 (Aurora-Rose, 1998); AURR980111 Normalized positional residue frequency at helix termini C5 (Aurora-Rose, 1998); AURR980112 Normalized positional residue frequency at helix termini C4 (Aurora-Rose, 1998); AURR980113 Normalized positional residue frequency at helix termini C3 (Aurora-Rose, 1998); AURR980114 Normalized positional residue frequency at helix termini C2 (Aurora-Rose, 1998); AURR980115 Normalized positional residue frequency at helix termini C1 (Aurora-Rose, 1998); AURR980116 Normalized positional residue frequency at helix termini Cc (Aurora-Rose, 1998); AURR980117 Normalized positional residue frequency at helix termini C' (Aurora-Rose, 1998); AURR980118 Normalized positional residue frequency at helix termini C" (Aurora-Rose, 1998); AURR980119 Normalized positional residue frequency at helix termini C''' (Aurora-Rose, 1998); AURR980120 Normalized positional residue frequency at helix termini C4' (Aurora-Rose, 1998); ONEK900101 Delta G values for the peptides extrapolated to 0 M urea (O'Neil-DeGrado, 1990); ONEK900102 Helix formation parameters (delta delta G) (O'Neil-DeGrado, 1990); VINM940101 Normalized flexibility parameters (B-values), average (Vihinen et al., 1994); VINM940102 Normalized flexibility parameters (B-values) for each residue surrounded by none rigid neighbours (Vihinen et al., 1994); VINM940103 Normalized flexibility parameters (B-values) for each residue surrounded by one rigid neighbours (Vihinen et al., 1994); VINM940104 Normalized flexibility parameters (B-values) for each residue surrounded by two rigid neighbours (Vihinen et al., 1994); MUNV940101 Free energy in alpha-helical conformation (Munoz-Serrano, 1994); MUNV940102 Free energy in alpha-helical region (Munoz-Serrano, 1994); MUNV940103 Free energy in beta-strand conformation (Munoz-Serrano, 1994); MUNV940104 Free energy in beta-strand region (Munoz-Serrano, 1994); MUNV940105 Free energy in beta-strand region (Munoz-Serrano, 1994) WIMW960101 Free energies of transfer of AcW1-X-LL peptides from bilayer interface to water (Wimley-White, 1996); KIMC930101 Thermodynamic beta sheet propensity (Kim-Berg, 1993); MONM990101 Turn propensity scale for transmembrane helices (Monne et al., 1999); BLAM930101 Alpha helix propensity of position 44 in T4 lysozyme (Blaber et al., 1993); PARS000101 p-Values of mesophilic proteins based on the distributions of B values (Parthasarathy-Murthy, 2000); PARS000102 p-Values of thermophilic proteins based on the distributions of B values (Parthasarathy-Murthy, 2000); KUMS000101 Distribution of amino acid residues in the 18 non-redundant families of thermophilic proteins (Kumar et al., 2000); KUMS000102 Distribution of amino acid residues in the 18 non-redundant families of mesophilic proteins (Kumar et al., 2000); KUMS000103 Distribution of amino acid residues in the alpha-helices in thermophilic proteins (Kumar et al., 2000); KUMS000104 Distribution of amino acid residues in the alpha-helices in mesophilic proteins (Kumar et al., 2000); TAKK010101 Side-chain contribution to protein stability (kJ/mol) (Takano-Yutani, 2001); FODM020101 Propensity of amino acids within pi-helices (Fodje-Al-Karadaghi, 2002); NADH010101 Hydropathy scale based on self-information values in the two-state model (5% accessibility) (Naderi-Manesh et al., 2001); NADH010102 Hydropathy scale based on self-information values in the two-state model (9% accessibility) (Naderi-Manesh et al., 2001); NADH010103 Hydropathy scale based on self-information values in the two-state model (16% accessibility) (Naderi-Manesh et al., 2001); NADH010104 Hydropathy scale based on self-information values in the two-state model (20% accessibility) (Naderi-Manesh et al., 2001); NADH010105 Hydropathy scale based on self-information values in the two-state model (25% accessibility) (Naderi-Manesh et al., 2001); NADH010106 Hydropathy scale based on self-information values in the two-state model (36% accessibility) (Naderi-Manesh et al., 2001); NADH010107 Hydropathy scale based on self-information values in the two-state model (50% accessibility) (Naderi-Manesh et al., 2001); MONM990201 Averaged turn propensities in a transmembrane helix (Monne et al., 1999); KOEP990101 Alpha-helix propensity derived from designed sequences (Koehl-Levitt, 1999); KOEP990102 Beta-sheet propensity derived from designed sequences (Koehl-Levitt, 1999); CEDJ970101 Composition of amino acids in extracellular proteins (percent) (Cedano et al., 1997); CEDJ970102 Composition of amino acids in anchored proteins (percent) (Cedano et al., 1997); CEDJ970103 Composition of amino acids in membrane proteins (percent) (Cedano et al., 1997); CEDJ970104 Composition of amino acids in intracellular proteins (percent) (Cedano et al., 1997); CEDJ970105 Composition of amino acids in nuclear proteins (percent) (Cedano et al., 1997); FUKS010101 Surface composition of amino acids in intracellular proteins of thermophiles (percent) (Fukuchi-Nishikawa, 2001); FUKS010102 Surface composition of amino acids in intracellular proteins of mesophiles (percent) (Fukuchi-Nishikawa, 2001); FUKS010103 Surface composition of amino acids in extracellular proteins of mesophiles (percent) (Fukuchi-Nishikawa, 2001); FUKS010104 Surface composition of amino acids in nuclear proteins (percent) (Fukuchi-Nishikawa, 2001); FUKS010105 Interior composition of amino acids in intracellular proteins of thermophiles (percent) (Fukuchi-Nishikawa, 2001); FUKS010106 Interior composition of amino acids in intracellular proteins of mesophiles (percent) (Fukuchi-Nishikawa, 2001); FUKS010107 Interior composition of amino acids in extracellular proteins of mesophiles (percent) (Fukuchi-Nishikawa, 2001); FUKS010108 Interior composition of amino acids in nuclear proteins (percent) (Fukuchi-Nishikawa, 2001); FUKS010109 Entire chain composition of amino acids in intracellular proteins of thermophiles (percent) (Fukuchi-Nishikawa, 2001); FUKS010110 Entire chain composition of amino acids in intracellular proteins of mesophiles (percent) (Fukuchi-Nishikawa, 2001); FUKS010111 Entire chain composition of amino acids in extracellular proteins of mesophiles (percent) (Fukuchi-Nishikawa, 2001); FUKS010112 Entire chain composition of amino acids in nuclear proteins (percent) (Fukuchi-Nishikawa, 2001); AVBF000101 Screening coefficients gamma, local (Avbelj, 2000); AVBF000102 Screening coefficients gamma, non-local (Avbelj, 2000); AVBF000103 Slopes tripeptide, FDPB VFF neutral (Avbelj, 2000); AVBF000104 Slopes tripeptides, LD VFF neutral (Avbelj, 2000); AVBF000105 Slopes tripeptide, FDPB VFF noside (Avbelj, 2000); AVBF000106 Slopes tripeptide FDPB VFF all (Avbelj, 2000); AVBF000107 Slopes tripeptide FDPB PARSE neutral (Avbelj, 2000); AVBF000108 Slopes dekapeptide, FDPB VFF neutral (Avbelj, 2000); AVBF000109 Slopes proteins, FDPB VFF neutral (Avbelj, 2000); YANJ020101 Side-chain conformation by gaussian evolutionary method (Yang et al., 2002); MITS020101 Amphiphilicity index (Mitaku et al., 2002); TSAJ990101 Volumes including the crystallographic waters using the ProtOr (Tsai et al., 1999); TSAJ990102 Volumes not including the crystallographic waters using the ProtOr (Tsai et al., 1999); COSI940101 Electron-ion interaction potential values (Cosic, 1994); PONP930101 Hydrophobicity scales (Ponnuswamy, 1993); WILM950101 Hydrophobicity coefficient in RP-HPLC, C18 with 0.1% TFA/MeCN/H2O (Wilce et al. 1995); WILM950102 Hydrophobicity coefficient in RP-HPLC, C8 with 0.1% TFA/MeCN/H2O (Wilce et al. 1995); WILM950103 Hydrophobicity coefficient in RP-HPLC, C4 with 0.1% TFA/MeCN/H2O (Wilce et al. 1995); WILM950104 Hydrophobicity coefficient in RP-HPLC, C18 with 0.1% TFA/2-PrOH/MeCN/H2O (Wilce et al. 1995); KUHL950101 Hydrophilicity scale (Kuhn et al., 1995); GUOD860101 Retention coefficient at pH 2 (Guo et al., 1986); JURD980101 Modified Kyte-Doolittle hydrophobicity scale (Juretic et al., 1998); BASU050101 Interactivity scale obtained from the contact matrix (Bastolla et al., 2005); BASU050102 Interactivity scale obtained by maximizing the mean of correlation coefficient over single-domain globular proteins (Bastolla et al., 2005); BASU050103 Interactivity scale obtained by maximizing the mean of correlation coefficient over pairs of sequences sharing the TIM barrel fold (Bastolla et al., 2005); SUYM030101 Linker propensity index (Suyama-Ohara, 2003); PUNT030101 Knowledge-based membrane-propensity scale from 1D_Helix in MPtopo databases (Punta-Maritan, 2003); PUNT030102 Knowledge-based membrane-propensity scale from 3D_Helix in MPtopo databases (Punta-Maritan, 2003); GEOR030101 Linker propensity from all dataset (George-Heringa, 2003); GEOR030102 Linker propensity from 1-linker dataset (George-Heringa, 2003); GEOR030103 Linker propensity from 2-linker dataset (George-Heringa, 2003); GEOR030104 Linker propensity from 3-linker dataset (George-Heringa, 2003); GEOR030105 Linker propensity from small dataset (linker length is less than six residues) (George-Heringa, 2003); GEOR030106 Linker propensity from medium dataset (linker length is between six and 14 residues) (George-Heringa, 2003); GEOR030107 Linker propensity from long dataset (linker length is greater than 14 residues) (George-Heringa, 2003); GEOR030108 Linker propensity from helical (annotated by DSSP) dataset (George-Heringa, 2003); GEOR030109 Linker propensity from non-helical (annotated by DSSP) dataset (George-Heringa, 2003); ZHOH040101 The stability scale from the knowledge-based atom-atom potential (Zhou-Zhou, 2004); ZHOH040102 The relative stability scale extracted from mutation experiments (Zhou-Zhou, 2004); ZHOH040103 Buriability (Zhou-Zhou, 2004); BAEK050101 Linker index (Bae et al., 2005); HARY940101 Mean volumes of residues buried in protein interiors (Harpaz et al., 1994); PONJ960101 Average volumes of residues (Pontius et al., 1996); DIGM050101 Hydrostatic pressure asymmetry index, PAI (Di Giulio, 2005); WOLR790101 Hydrophobicity index (Wolfenden et al., 1979); OLSK800101 Average internal preferences (Olsen, 1980); KIDA850101 Hydrophobicity-related index (Kidera et al., 1985); GUYH850102 Apparent partition energies calculated from Wertz-Scheraga index (Guy, 1985); GUYH850103 Apparent partition energies calculated from Robson-Osguthorpe index (Guy, 1985); GUYH850104 Apparent partition energies calculated from Janin index (Guy, 1985); GUYH850105 Apparent partition energies calculated from Chothia index (Guy, 1985); ROSM880104 Hydropathies of amino acid side chains, neutral form (Roseman, 1988); ROSM880105 Hydropathies of amino acid side chains, pi-values in pH 7.0 (Roseman, 1988); JACR890101 Weights from the IFH scale (Jacobs-White, 1989); COWR900101 Hydrophobicity index, 3.0 pH (Cowan-Whittaker, 1990) BLAS910101 Scaled side chain hydrophobicity values (Black-Mould, 1991); CASG920101 Hydrophobicity scale from native protein structures (Casari-Sippl, 1992); CORJ870101 NNEIG index (Cornette et al., 1987); CORJ870102 SWEIG index (Cornette et al., 1987); CORJ870103 PRIFT index (Cornette et al., 1987); CORJ870104 PRILS index (Cornette et al., 1987); CORJ870105 ALTFT index (Cornette et al., 1987) CORJ870106 ALTLS index (Cornette et al., 1987); CORJ870107 TOTFT index (Cornette et al., 1987); CORJ870108 TOTLS index (Cornette et al., 1987); MIYS990101 Relative partition energies derived by the Bethe approximation (Miyazawa-Jernigan, 1999); MIYS990102 Optimized relative partition energies –method A (Miyazawa-Jernigan, 1999); MIYS990103 Optimized relative partition energies—method B (Miyazawa-Jernigan, 1999); MIYS990104 Optimized relative partition energies—method C (Miyazawa-Jernigan, 1999); MIYS990105 Optimized relative partition energies—method D (Miyazawa-Jernigan, 1999); ENGD860101 Hydrophobicity index (Engelman et al., 1986); and FASG890101 Hydrophobicity index (Fasman, 1989)

In some embodiments of the invention, degenerate oligonucleotides are used to synthesize one or more of the TN1, DH, N2, and/or H3-JH segments of the invention. In certain embodiments of the invention, the codon at or near the 5' end of the oligonucleotide encoding the H3-JH segment is a degenerate codon. Such degenerate codons may be the first codon from the 5' end, the second codon from the 5' end, the third codon from the 5' end, the fourth codon from the 5' end, the fifth codon from the 5' end, and/or any combination of the above. In some embodiments of the invention, one or more of the codons at or near the 5' and/or 3' ends of the DH segment are degenerate. Such degenerate codons may be the first codon from the 5' and/or 3' end(s), the second codon from the 5' and/or 3' end(s), the third codons from the 5' and/or 3' end(s), the fourth codon from the 5' and/or 3' end(s), the fifth codon from the 5' and/or 3' end(s), and/or any combination of the above. Degenerate codons used in each of the oligonucleotides encoding the segments may be selected for their ability to optimally recapitulate sequences in a theoretical segment pool and/or CDRH3 reference set.

In some embodiments, the invention provides methods of producing a theoretical segment pool of H3-JH segments, as described in the Examples. Theoretical segment pools generated utilizing NNN triplets, instead of or in addition to the NN doublets described in Example 5 also fall within the scope of the invention, as do synthetic libraries incorporating segments from these theoretical segment pools.

In some embodiments, the invention provides methods of producing a theoretical segment pool of DH segments, as described in the Examples. In particular, for example, the invention provides methods of producing a theoretical segment pool of DH segments described by the PYTHON program of Example 6. Example 6 describes the application of this program to produce the 68K theoretical segment pool (minimum length of DNA sequences after progressive deletions=4 bases; and minimum length of peptide sequences for inclusion in the theoretical segment pool=2). An alternative example is provided wherein the minimum length of the DNA sequences after progressive deletions was one base and the minimum length of the peptide sequence is one amino acid. It is also contemplated that other values could be used for these parameters. For example, the minimum length of the DNA sequences after progressive deletions could be set as 1, 2, 3, 4, 5, 6, 7, 8, 9, 10, 11, 12, 13, 14, or 15, and the minimum length of the peptide sequences in the theoretical segment pool could be set as 1, 2, 3, 4, or 5.

Design of CDRH3 Libraries Using the TN1, DH, N2, and H3-JH Segments

The CDRH3 libraries of the invention comprise TN1, DH, N2, and H3-JH segments. Thus, in certain embodiments of the invention, the overall design of the CDRH3 libraries can be represented by the following formula:

[TN1]-[DH]-[N2]-[H3-JH].

In certain embodiments of the invention, a synthetic CDRH3 repertoire is combined with selected VH chassis sequences and heavy chain constant regions, via homologous recombination. Therefore, in certain embodiments of the invention, it may be desirable to include DNA sequences flanking the 5' and 3' ends of the synthetic CDRH3 libraries, to facilitate homologous recombination between the synthetic CDRH3 libraries and vectors containing the selected chassis and constant regions. In certain embodiments, the vectors also contain a sequence encoding at least a portion of the non-truncated region of the IGHJ gene (i.e., FRM4-JH). Thus, a polynucleotide encoding an N-terminal sequence (e.g., CA(K/R/T)) may be added to the synthetic CDRH3 sequences, wherein the N-terminal polynucleotide is homologous with FRM3 of the chassis, while a polynucleotide encoding a C-terminal sequence (e.g., WG(Q/R/K)G) may be added to the synthetic CDRH3, wherein the C-terminal polynucleotide is homologous with FRM4-JH. Although the sequence WG(Q/R)G is presented in this exemplary embodiment, additional amino acids, C-terminal to this sequence in FRM4-JH may also be included in the polynucleotide encoding the C-terminal sequence. The purpose of the polynucleotides encoding the N-terminal and C-terminal sequences, in this case, is to facilitate homologous recombination, and one of ordinary skill in the art would recognize that these sequences may be longer or shorter than depicted below. Accordingly, in certain embodiments of the invention, the overall design of the CDRH3 repertoire, including the sequences required to facilitate homologous recombination with the selected chassis, can be represented by the following formula (regions homologous with vector underlined):

(SEQ ID NO. 8762, SEQ ID NO. 8763, and SEQ ID NO. 8764, respectively)
CA[R/K/T]-[TN1]-[DH]-[N2]-[H3-JH]-WG(Q/R/K)G.

In some embodiments of the invention, the CDRH3 repertoire can be represented by the following formula, which excludes the T residue presented in the schematic above:

(SEQ ID NO. 8762, SEQ ID NO. 8763, and
SEQ ID NO. 8764, respectively)
CA[R/K]-[TN1]-[DH]-[N2]-[H3-JH]-[WG(Q/R/K)G].

References describing collections of V, D, and J genes include Scaviner et al., Exp. Clin, Immunogenet., 1999, 16: 243 and Ruiz et al., Exp. Clin. Immunogenet, 1999, 16: 173, each incorporated by reference in its entirety.

Although homologous recombination is one method of producing the libraries of the invention, a person of ordinary skill in the art will readily recognize that other methods of DNA assembly, such as ligation or site-specific recombination, and/or DNA synthesis, can also be used to produce the libraries of the invention.

CDRH3 Lengths

The lengths of the segments may also be varied, for example, to produce libraries with a particular distribution of CDRH3 lengths. In one embodiment of the invention, the H3-JH segments are about 0 to about 10 amino acids in length, the DH segments are about 0 to about 12 amino acids in length, the TN1 segments are about 0 to about 4 amino acids in length, and the N2 segments are about 0 to about 4 amino acids in length. In certain embodiments, the H3-JH segments are at least about 0, 1, 2, 3, 4, 5, 6, 7, 8, 9, and/or 10 amino acids in length. In some embodiments, the DH segments are at least about 0, 1, 2, 3, 4, 5, 6, 7, 8, 9, 10, 11, and/or 12 amino acids in length. In certain embodiments, the TN1 segments are at least about 0, 1, 2, 3, or 4 amino acids in length. In some embodiments, the N2 amino acids are at least about 0, 1, 2, 3, or 4 amino acids in length. In certain embodiments of the invention, the CDRH3 is about 2 to about 35, about 2 to about 28, or about 5 to about 26 amino acids in length. In some embodiments, the CDRH3 is at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and/or 35 amino acids in length. In some embodiments, the length of any of the segments or CDRH3s of the invention may be less than a particular number of amino acids, where the number of amino acids is defined using any one of the integers provided above for the respective segment or CDRH3. In certain embodiments of the invention, a particular numerical range is defined, using any two of the integers provided above as lower and upper boundaries of the range, inclusive or exclusive. All combinations of the integers provided, which define an upper and lower boundary, are contemplated.

Design of CDRL3 Libraries

The design of CDRL3 libraries, and light chain sequences, is described in detail in U.S. Publication Nos. 2009/0181855 and 2010/0056386, and WO/2009/036379, each of which is incorporated by reference in its entirety, and is therefore only described briefly herein. Libraries described herein are designed according to similar principles, with three important differences, namely that the libraries of the current invention contain (1) variability in CDRL1 and CDRL2; (2) variability in the framework regions; and/or (3) variability in CDRL3 that is designed to produce light chain libraries with CDRL3s that closely resemble human germline-like CDRL3 sequences, as defined above (Table 1).

A CDRL3 library of the invention may be a VKCDR3 library and/or a VλCDR3 library. In certain embodiments of the invention, patterns of occurrence of particular amino acids at defined positions within VL sequences are determined by analyzing data available in public or other databases, for example, the NCBI database (see, for example, WO/2009/036379). In certain embodiments of the invention, these sequences are compared on the basis of identity and assigned to families on the basis of the germline genes from which they are derived. The amino acid composition at each position of the sequence, in each germline family, may then be determined. This process is illustrated in the Examples provided herein.

Light Chains with Framework Variability

In some embodiments, the invention provides a library of light chain variable domains wherein the light chain variable domains are varied at one or more of framework positions 2, 4, 36, 46, 48, 49, and 66. In some embodiments, the invention provides a library of light chain variable domains comprising at least a plurality of light chain variable domains whose amino acid sequences are identical to one another except for substitutions at one or more of positions 2, 4, 36, 46, 48, 49, and 66. In certain embodiments, the invention provides a library of light chain variable domains comprising at least a plurality of light chain variable domains whose amino acid sequences are at least about 70%, 75%, 80%, 85%, 90%, 95%, 96%, 97%, 98%, 99%, and/or 99.5% to any of the light chain variable domain sequences disclosed herein, and further have substitutions at one or more of positions 2, 4, 36, 46, 48, 49, and 66. In some embodiments, the amino acids selected for inclusion in these positions are selected from amongst about the most 2, 3, 4, 5, 6, 7, 8, 9, and/or 10 most frequently occurring amino acids at the corresponding position in a reference set of light chain variable domains.

In some embodiments, the invention provides systems and methods of selecting framework positions to be varied in a light chain variable domain, comprising:
  (i) obtaining a reference set of light chain sequences, wherein the reference set contains light chain sequences with VL segments selected from the group consisting of sequences found in, or encoded by, a single IGVL germline gene and/or sequences found in, or encoded by, allelic variants of the single IGVL germline gene;
  (ii) determining which framework positions within the reference set have a degree of variability that is similar to the degree of variability occurring in one more CDR positions of the sequences in the reference set (e.g., the variability in a framework position is at least about 70%, 80%, 90%, or 95%, 100%, or more of the variability found in a CDR position of the sequences in the reference set);
  (iii) determining the frequency of occurrence of amino acid residues for each of the framework positions identified in (ii);
  (iv) synthesizing light chain variable domain encoding sequences wherein the framework positions identified in (ii) are varied to include the 2, 3, 4, 5, 6, 7, 8, 9, 10, 11, 12, 13, 14, 15, 16, 17, 18, 19, or 20 most frequently occurring amino acid residues (identified in (iii)) at the corresponding position.

One of ordinary skill in the art, reading the present disclosure will appreciate that the present invention provides analogous methods for developing framework variants of heavy chain sequences.

Light Chains with CDR1 and/or CDR2 Variability

In some embodiments, the invention provides a library of light chain variable domains wherein the light chain variable domains are varied at one or more of CDRL1 positions 28, 29, 30, 30A, 30B, 30E, 31, and 32 (Chothia-Lesk numbering scheme; Chothia and Lesk, J. Mol. Biol., 1987, 196: 901). In some embodiments, the invention provides a library of light chain variable domains wherein the light chain variable domains are varied at one or more of CDRL2 positions 50, 51, 53, and 55. In some embodiments, the amino acids selected for inclusion in these CDRL1 and/or CDRL2 positions are selected from amongst about the most 2, 3, 4, 5, 6, 7, 8, 9, 10, 11, 12, 13, 14, 15, 16, 17, 18, 19, and/or 20 most frequently occurring amino acids at the corresponding position in a reference set of light chain variable domains.

In some embodiments, the invention provides systems and methods for selecting CDRL1 and/or CDRL2 positions to be varied in a light chain variable domain, comprising:
 (i) obtaining a reference set of light chain sequences, wherein the reference set contains light chain sequences with VL segments selected from the group consisting of sequences found in, or encoded by, a single IGVL germline gene and sequences found in, or encoded by, allelic variants of the single IGVL germline gene;
 (ii) determining which CDRL1 and/or CDRL2 positions are variable within the reference set;
 (iii) synthesizing light chain variable domain encoding sequences wherein the CDRL1 and/or CDRL2 positions identified in (ii) are varied to include the 2, 3, 4, 5, 6, 7, 8, 9, 10, 11, 12, 13, 14, 15, 16, 17, 18, 19, or 20 most frequently occurring amino acid residues at the corresponding position.

One of ordinary skill in the art, reading the present disclosure will appreciate that the present invention provides analogous methods for developing CDRH2 and/or CDRH2 variants of heavy chain sequences.

Light Chain Sequences

In some embodiments, the invention provides a light chain library comprising one or more of any of the light chain sequences provided herein, for example, the polypeptide sequences of Table 3 and/or Table 4 and/or the polynucleotide sequences of Table 5, Table 6, and/or Table 7. A person of ordinary skill in the art will recognize that not every light chain sequence provided herein is necessary to produce a functional light chain library of the invention. Therefore, in certain embodiments, a light chain library of the invention will contain a subset of the sequences described above. For example, in certain embodiments of the invention, at least about 10, 100, 200, 300, 400, 500, 600, 700, 800, 900, $10^3$, $10^4$, and/or $10^5$ of the light chain polynucleotide and/or polypeptide sequences provided herein are included in a library. In some embodiments, a library of the invention may contain less than a particular number of polynucleotide or polypeptide segments, where the number of segments is defined using any one of the integers provided above for the respective segment. In certain embodiments of the invention, a particular numerical range is defined, using any two of the integers provided above as lower and upper boundaries of the range, inclusive or exclusive. All combinations of the integers provided, which define an upper and lower boundary, are contemplated.

In certain embodiments, the invention provides light chain libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the sequences from any of the sets of light chain sequences provided herein. For example, the invention provides libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences provided in Table 3, Table 4, Table 5, Table 6, and/or Table 7. In some embodiments of the invention, a particular percentage range is defined, using any two of the percentages provided above as lower and upper boundaries of the range, inclusive or exclusive. All combinations of the percentages provided, which define an upper and lower boundary, are contemplated.

In some embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences in a library are light chain sequences provided herein. In certain embodiments of the invention, at least about 1%, 2.5%, 5%, 10%, 15%, 20%, 25%, 30%, 40%, 45%, 50%, 55%, 60%, 65%, 70%, 75%, 80%, 85%, 90%, 95%, or 99% of the light chain sequences isolated from a light chain library (e.g., by binding to a particular antigen and/or generic ligand) are light chain sequences provided herein. In some embodiments, a light chain library of the invention may contain less than a particular percentage of light chain sequences provided herein, where the percentage of light chain sequences is defined using any one of the percentages provided above. In certain embodiments of the invention, a particular percentage range is defined, using any two of the percentages provided above as lower and upper boundaries of the range, inclusive or exclusive. All combinations of the percentages provided, which define an upper and lower boundary, are contemplated.

One of ordinary skill in the art will further recognize that given the light chain sequences provided herein, similar light chain sequences could be produced which share a designated level of overall sequence identity and/or one or more characteristic sequence elements described herein, which overall degree of sequence identity and/or characteristic sequence elements may confer common functional attributes. Those of ordinary skill in the art will be well familiar with a variety of techniques for preparing such related sequences, including the mutagenesis techniques provided herein. Therefore, each of the explicitly enumerated embodiments of the invention can also be practiced using light chain sequences that share a particular percent identity to any of the light chain sequences provided herein. For example, each of the previously described embodiments of the invention can be practiced using light chain sequences that are at least about 70%, 75%, 80%, 85%, 90%, 91%, 92%, 93%, 94%, 95%, 96%, 97%, 98%, 99%, 99.5%, or 99.9% identical to the light chain sequences provided herein. For example, in some embodiments, light chain libraries provided by the invention comprise light chain variable domains at least about 70%, 75%, 80%, 85%, 90%, 91%, 92%, 93%, 94%, 95%, 96%, 97%, 98%, 99%, 99.5%, or 99.9% identical to the light chain sequences provided herein, with substitutions in one or more of framework positions 2, 4, 36, 46, 48, 49, and 66, CDRL1 positions 28, 29, 30, 30A, 30B, 30E, 31, and 32 (Chothia-Lesk numbering scheme), and/or CDRL2 positions 50, 51, 53, and 55.

In some embodiments, the invention provides systems and methods for varying positions within the portion of CDRL3s encoded by a particular IGVL germline gene, comprising:
 (i) obtaining a reference set of light chain sequences, wherein the reference set contains light chain sequences with VL segments originating from the same IGVL germline gene and/or its allelic variants;

(ii) determining which amino acids occur at each of the CDRL3 positions in the reference set that are encoded by the IGVL gene (i.e., positions 89-94, inclusive);

(iii) synthesizing light chain variable domain encoding sequences wherein two positions in each light chain variable domain encoding sequence contain degenerate codons encoding the 2, 3, 4, 5, 6, 7, 8, 9, 10, 11, 12, 13, 14, 15, 16, 17, 18, 19, or 20 most frequently occurring amino acid residues at the corresponding positions in the reference set.

As described in the examples, the degenerate codons of (iii) can be chosen to best reproduce the amino acid diversity contained in the reference set for each of the two positions varied in each light chain. Finally, while the methods and systems described above are described with respect to CDRL3, one of ordinary skill in the art will readily recognize that the same principles can be applied to CDRH1 and/or CDRH2 of the heavy chain, which are encoded entirely by the IGHV gene.

CDRL3 Lengths

In some embodiments, as an alternative or in addition to other features described herein, the present invention provides libraries in which lengths of CDRL3s may be varied. The present invention therefore provides, among other things, libraries with a particular distribution of CDRL3 lengths. Although CDRL3 libraries of lengths 8, 9, and 10 are exemplified, one of ordinary skill in the art will readily recognize that the methods described herein can be applied to produce light chains with CDRL3s of different lengths (e.g., about 5, 6, 7, 11, 12, 13, 14, 15, and/or 16) that also fall within the scope of the invention. In some embodiments, the length of any of the CDRL3s of the invention may be less than a particular number of amino acids, where the number of amino acids is defined using any one of the integers provided above. In some embodiments of the invention, a particular numerical range is defined, using any two of the integers provided above as lower and upper boundaries of the range, inclusive or exclusive. All combinations of the integers provided, which define an upper and lower boundary, are contemplated.

Synthetic Antibody Libraries

In some embodiments of the invention, provided libraries include one or more synthetic polynucleotides. In some embodiments, provided libraries may comprise synthetic polynucleotides selected from (a) heavy chain chassis polynucleotides; (b) light chain chassis polynucleotides; (c) CDR3 polynucleotides; (d) constant domain polynucleotides; and (e) combinations thereof. Those of ordinary skill in the art will appreciate that such synthetic polynucleotides may be linked to other synthetic or non-synthetic polynucleotides in provided libraries.

Synthetic polynucleotides provided herein may be prepared by any available method. For example, in some embodiments, synthetic polynucleotides can be synthesized by split pool DNA synthesis as described in Feldhaus et al., Nucleic Acids Research, 2000, 28: 534; Omstein et al., Biopolymers, 1978, 17: 2341; Brenner and Lerner, PNAS, 1992, 87: 6378, U.S. Publication Nos. 2009/0181855 and 2010/0056386, and WO/2009/036379 (each incorporated by reference in its entirety).

In some embodiments of the invention, segments representing the possible TN1, DH, N2, and JH diversity found in the human repertoire are synthesized de novo either as double-stranded DNA oligonucleotides, single-stranded DNA oligonucleotides representative of the coding strand, or single-stranded DNA oligonucleotides representative of the non-coding strand. Such sequences can then be introduced into a host cell along with an acceptor vector containing a chassis sequence and, in some cases a portion of FRM4 and a constant region. No primer-based PCR amplification from mammalian cDNA or mRNA or template-directed cloning steps from mammalian cDNA or mRNA need be employed.

Construction of Libraries by Yeast Homologous Recombination

In certain embodiments, the invention exploits the inherent ability of yeast cells to facilitate homologous recombination at high efficiency. The mechanism of homologous recombination in yeast and its applications are briefly described below (also see e.g., U.S. Pat. Nos. 6,406,863; 6,410,246; 6,410,271; 6,610,472; and 7,700,302, each of which is incorporated by reference in its entirety).

As an illustrative embodiment, homologous recombination can be carried out in, for example, *Saccharomyces cerevisiae*, which has genetic machinery designed to carry out homologous recombination with high efficiency. Exemplary *S. cerevisiae* strains include EM93, CEN.PK2, RM11-1a, YJM789, and BJ5465. This mechanism is believed to have evolved for the purpose of chromosomal repair, and is also called "gap repair" or "gap filling". By exploiting this mechanism, mutations can be introduced into specific loci of the yeast genome. For example, a vector carrying a mutant gene can contain two sequence segments that are homologous to the 5' and 3' open reading frame (ORF) sequences of a gene that is intended to be interrupted or mutated. The vector may also encode a positive selection marker, such as a nutritional enzyme allele (e.g., URA3) and/or an antibiotic resistant marker (e.g., Geneticin/G418), flanked by the two homologous DNA segments. Other selection markers and antibiotic resistance markers are known to one of ordinary skill in the art.

In some embodiments of the invention, this vector (e.g., a plasmid) is linearized and transformed into the yeast cells. Through homologous recombination between the plasmid and the yeast genome, at the two homologous recombination sites, a reciprocal exchange of the DNA content occurs between the wild type gene in the yeast genome and the mutant gene (including the selection marker gene(s)) that is flanked by the two homologous sequence segments. By selecting for the one or more selection markers, the surviving yeast cells will be those cells in which the wild-type gene has been replaced by the mutant gene (Pearson et al., Yeast, 1998, 14: 391, incorporated by reference in its entirety). This mechanism has been used to make systematic mutations in all 6,000 yeast genes, or open reading frames (ORFs), for functional genomics studies. Because the exchange is reciprocal, a similar approach has also been used successfully to clone yeast genomic DNA fragments into a plasmid vector (Iwasaki et al., Gene, 1991, 109: 81, incorporated by reference in its entirety).

By utilizing the endogenous homologous recombination machinery present in yeast, gene fragments or synthetic oligonucleotides can also be cloned into a plasmid vector without a ligation step. In this application of homologous recombination, a target gene fragment (i.e., the fragment to be inserted into a plasmid vector, e.g., a CDR3) is obtained (e.g., by oligonucleotides synthesis, PCR amplification, restriction digestion out of another vector, etc.). DNA sequences that are homologous to selected regions of the plasmid vector are added to the 5' and 3' ends of the target gene fragment. These homologous regions may be fully synthetic, or added via PCR amplification of a target gene fragment with primers that incorporate the homologous sequences. The plasmid vector may include a positive selection marker, such as a nutritional enzyme allele (e.g., URA3), or an antibiotic resistance marker (e.g., Geneticin/G418). The plasmid vector is then linearized by a unique restriction cut located in-between the regions of sequence homology shared with the target gene fragment, thereby creating an artificial gap at the cleavage site. The linearized plasmid vector and the target gene fragment flanked by sequences homologous to the plasmid vector are co-transformed into a yeast host strain. The yeast is then able to recognize the two stretches of sequence homology between the vector and target gene fragment and facilitate a reciprocal exchange of DNA content through homologous recombination at the gap. As a consequence, the target gene fragment is inserted into the vector without ligation.

The method described above has also been demonstrated to work when the target gene fragments are in the form of single stranded DNA, for example, as a circular M13 phage derived form, or as single stranded oligonucleotides (Simon and Moore, Mol. Cell Biol., 1987, 7: 2329; Ivanov et al., Genetics, 1996, 142: 693; and DeMarini et al., 2001, 30: 520, each incorporated by reference in its entirety). Thus, the form of the target that can be recombined into the gapped vector can be double stranded or single stranded, and derived from chemical synthesis, PCR, restriction digestion, or other methods.

Several factors may influence the efficiency of homologous recombination in yeast. For example, the efficiency of the gap repair is correlated with the length of the homologous sequences flanking both the linearized vector and the target gene. In certain embodiments, about 20 or more base pairs may be used for the length of the homologous sequence, and about 80 base pairs may give a near-optimized result (Hua et al., Plasmid, 1997, 38: 91; Raymond et al., Genome Res., 2002, 12: 190, each incorporated by reference in its entirety). In certain embodiments of the invention, at least about 5, 10, 15, 20, 21, 22, 23, 24, 25, 26, 27, 28, 29, 30, 31, 32, 33, 34 35, 36, 37, 38, 39, 40, 45, 50, 55, 60, 65, 70, 75, 80, 85, 90, 95, 100, 110, 120, 130, 140, 150, 160, 170, 180, 187, 190, or 200 homologous base pairs may be used to facilitate recombination. In certain embodiments, between about 20 and about 40 base pairs are utilized. In addition, the reciprocal exchange between the vector and gene fragment is strictly sequence-dependent, i.e. it does not cause a frame shift. Therefore, gap-repair cloning assures the insertion of gene fragments with both high efficiency and precision. The high efficiency makes it possible to clone two, three, or more targeted gene fragments simultaneously into the same vector in one transformation attempt (Raymond et al., Biotechniques, 1999, 26: 134, incorporated by reference in its entirety). Moreover, the nature of precision sequence conservation through homologous recombination makes it possible to clone selected genes or gene fragments into expression or fusion vectors for direct functional examination (El-Deiry et al., Nature Genetics, 1992, 1: 4549; Ishioka et al., PNAS, 1997, 94: 2449, each incorporated by reference in its entirety).

Libraries of gene fragments have also been constructed in yeast using homologous recombination. For example, a human brain cDNA library was constructed as a two-hybrid fusion library in vector pJG4-5 (Guidotti and Zervos, Yeast, 1999, 15: 715, incorporated by reference in its entirety). It has also been reported that a total of 6,000 pairs of PCR primers were used for amplification of 6,000 known yeast ORFs for a study of yeast genomic protein interactions (Hudson et al., Genome Res., 1997, 7: 1169, incorporated by reference in its entirety). In 2000, Uetz et al. conducted a comprehensive analysis-of protein-protein interactions in *Saccharomyces cerevisiae* (Uetz et al., Nature, 2000, 403: 623, incorporated by reference in its entirety). The protein-protein interaction map of the budding yeast was studied by using a comprehensive system to examine two-hybrid interactions in all possible combinations between the yeast proteins (Ito et al., PNAS, 2000, 97: 1143, incorporated by reference in its entirety), and the genomic protein linkage map of Vaccinia virus was studied using this system (McCraith et al., PNAS, 2000, 97: 4879, incorporated by reference in its entirety).

In certain embodiments of the invention, a synthetic CDR3 (heavy or light chain) may be joined by homologous recombination with a vector encoding a heavy or light chain chassis, a portion of FRM4, and a constant region, to form a full-length heavy or light chain. In certain embodiments of the invention, the homologous recombination is performed directly in yeast cells. In some embodiments, such a method comprises:

(a) transforming into yeast cells:
  (i) a linearized vector encoding a heavy or light chain chassis, a portion of FRM4, and a constant region, wherein the site of linearization is between the end of FRM3 of the chassis and the beginning of the constant region; and
  (ii) a library of CDR3 insert nucleotide sequences that are linear and double stranded, wherein each of the CDR3 insert sequences comprises a nucleotide sequence encoding CDR3 and 5'- and 3'-flanking sequences that are sufficiently homologous to the termini of the vector of (i) at the site of linearization to enable homologous recombination to occur between the vector and the library of CDR3 insert sequences; and
(b) allowing homologous recombination to occur between the vector and the CDR3 insert sequences in the transformed yeast cells, such that the CDR3 insert sequences are incorporated into the vector, to produce a vector encoding full-length heavy chain or light chain.

As specified above, CDR3 inserts may have a 5' flanking sequence and a 3' flanking sequence that are homologous to the termini of the linearized vector. When the CDR3 inserts and the linearized vectors are introduced into a host cell, for example, a yeast cell, the "gap" (the linearization site) created by linearization of the vector is filled by the CDR3 fragment insert through recombination of the homologous sequences at the 5' and 3' termini of these two linear double-stranded DNAs (i.e., the vector and the insert). Through this event of homologous recombination, libraries of circular vectors encoding full-length heavy or light chains comprising variable CDR3 inserts is generated. Particular instances of these methods are presented in the Examples.

Subsequent analysis may be carried out to determine, for example, the efficiency of homologous recombination that results in correct insertion of the CDR3 sequences into the vectors. For example, PCR amplification of the CDR3 inserts directly from selected yeast clones may reveal how many clones are recombinant. In certain embodiments, libraries with minimum of about 90% recombinant clones are utilized. In certain embodiments libraries with a minimum of about 1%, 5% 10%, 15%, 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% recombinant clones are utilized. The same PCR amplification of selected clones may also reveal the insert size.

To verify the sequence diversity of the inserts in the selected clones, a PCR amplification product with the correct size of insert may be "fingerprinted" with restriction enzymes known to cut or not cut within the amplified region. From a gel electrophoresis pattern, it may be determined whether the clones analyzed are of the same identity or of the distinct or diversified identity. The PCR products may also be sequenced directly to reveal the identity of inserts and the fidelity of the cloning procedure, and to prove the independence and diversity of the clones.

Expression and Screening Systems

Libraries of polynucleotides generated by any of the techniques described herein, or other suitable techniques, can be expressed and screened to identify antibodies having desired structure and/or activity. Expression of the antibodies can be carried out, for example, using cell-free extracts (and e.g., ribosome display), phage display, prokaryotic cells (e.g., bacterial display), or eukaryotic cells (e.g., yeast display). In certain embodiments of the invention, the antibody libraries are expressed in yeast.

In some embodiments, polynucleotides are engineered to serve as templates that can be expressed in a cell-free extract. Vectors and extracts as described, for example in U.S. Pat. Nos. 5,324,637; 5,492,817; 5,665,563, (each incorporated by reference in its entirety) can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553, each incorporated by reference in its entirety).

Alternatively or additionally, polynucleotides of the invention can be expressed in an *E. coli* expression system, such as that described by Pluckthun and Skerra. (Meth. Enzymol., 1989, 178: 476; Biotechnology, 1991, 9: 273, each incorporated by reference in its entirety). Mutant proteins can be expressed for secretion in the medium and/or in the cytoplasm of the bacteria, as described by Better and Horwitz, Meth. Enzymol., 1989, 178: 476, incorporated by reference in its entirety. In some embodiments, the single domains encoding VH and VL are each attached to the 3' end of a sequence encoding a signal sequence, such as the ompA, phoA or pelB signal sequence (Lei et al., J. Bacteriol., 1987, 169: 4379, incorporated by reference in its entirety). These gene fusions are assembled in a dicistronic construct, so that they can be expressed from a single vector, and secreted into the periplasmic space of *E. coli* where they will refold and can be recovered in active form. (Skerra et al., Biotechnology, 1991, 9: 273, incorporated by reference in its entirety). For example, antibody heavy chain genes can be concurrently expressed with antibody light chain genes to produce antibodies or antibody fragments.

In some embodiments of the invention, antibody sequences are expressed on the membrane surface of a prokaryote, e.g., *E. coli*, using a secretion signal and lipidation moiety as described, e.g., in US2004/0072740; US2003/0100023; and US2003/0036092 (each incorporated by reference in its entirety).

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the invention. Typically, antibodies expressed in mammalian cells are designed to be secreted into the culture medium, or expressed on the surface of the cell. Antibody or antibody fragments can be produced, for example, as intact antibody molecules or as individual VH and VL fragments, Fab fragments, single domains, or as single chains (scFv) (Huston et al., PNAS, 1988, 85: 5879, incorporated by reference in its entirety).

Alternatively or additionally, antibodies can be expressed and screened by anchored periplasmic expression (APEx 2-hybrid surface display), as described, for example, in Jeong et al., PNAS, 2007, 104: 8247 (incorporated by reference in its entirety) or by other anchoring methods as described, for example, in Mazor et al., Nature Biotechnology, 2007, 25: 563 (incorporated by reference in its entirety).

In some embodiments of the invention, antibodies can be selected using mammalian cell display (Ho et al., PNAS, 2006, 103: 9637, incorporated by reference in its entirety).

Screening of the antibodies derived from the libraries of the invention can be carried out by any appropriate means. For example, binding activity can be evaluated by standard immunoassay and/or affinity chromatography. Screening of antibodies of the invention for catalytic function, e.g., proteolytic function can be accomplished using a standard assays, e.g., the hemoglobin plaque assay as described in U.S. Pat. No. 5,798,208 (incorporated by reference in its entirety). Determining the ability of candidate antibodies to bind therapeutic targets can be assayed in vitro using, e.g., a BIACORE™ instrument, which measures binding rates of an antibody to a given target or antigen based on surface plasmon resonance. In vivo assays can be conducted using any of a number of animal models and then subsequently tested, as appropriate, in humans. Cell-based biological assays are also contemplated.

One feature of the instant invention is the speed at which the antibodies of the library can be expressed and screened. In certain embodiments of the invention, the antibody library can be expressed in yeast, which have a doubling time of less than about 3, 4, 5, 6, 7, 8, 9, 10, 11, 12, 13, 14, 15, 16, 17, 18, 19, 20, 21, 22, 23, or 24 hours. In some embodiments, the doubling times are about 1 to about 3 hours, about 2 to about 4, about 3 to about 8 hours, about 3 to about 24, about 5 to about 24, about 4 to about 6 about 5 to about 22, about 6 to about 8, about 7 to about 22, about 8 to about 10 hours, about 7 to about 20, about 9 to about 20, about 9 to about 18, about 11 to about 18, about 11 to about 16, about 13 to about 16, about 16 to about 20, or about 20 to about 30 hours. In certain embodiments of the invention, an antibody library is expressed in yeast with a doubling time of about 16 to about 20 hours, about 8 to about 16 hours, or about 4 to about 8 hours. Thus, an antibody library of the instant invention can be expressed and screened in a matter of hours, as compared to previously known techniques which take several days to express and screen antibody libraries. A limiting step in the throughput of such screening processes in mammalian cells is typically the time required to iteratively regrow populations of isolated cells, which, in some cases, have doubling times greater than the doubling times of the yeast used in the current invention.

In certain embodiments of the invention, the composition of a library may be defined after one or more enrichment steps (for example by screening for antigen binding, binding to a generic ligand, or other properties). For example, a library with a composition comprising about x % sequences or libraries of the invention may be enriched to contain about 2x %, 3x %, 4x %, 5x %, 6x %, 7x %, 8x %, 9x %, 10x %, 20x %, 25x %, 40x %, 50x %, 60x % 75x %, 80x %, 90x %, 95x %, or 99x % sequences or libraries of the invention, after one or more screening steps. In some embodiments of the invention, the sequences or libraries of the invention may be enriched about 2-fold, 3-fold, 4-fold, 5-fold, 6-fold, 7-fold, 8-fold, 9-fold, 10-fold, 100-fold, 1,000-fold, or more, relative to their occurrence prior to the one or more enrichment steps. In certain embodiments of the invention, a library may contain at least a certain number of a particular type of sequence(s), such as CDRH3s, CDRL3s, heavy chains, light chains, or whole antibodies (e.g., at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$). In certain embodiments, these sequences may be enriched during one or more enrichment steps, to provide libraries comprising at least about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, or $10^{19}$ of the respective sequence(s).

Mutagenesis Approaches for Affinity Maturation

As described above, antibody leads can be identified through a selection process that involves screening the antibodies of a library of the invention for binding to one or more antigens, or for a biological activity. Coding sequences of these antibody leads may be further mutagenized in vitro or in vivo to generate secondary libraries with diversity introduced in the context of the initial antibody leads. Such mutagenized antibody leads can then be further screened for binding to target antigens or biological activity, in vitro or in vivo, following procedures similar to those used for the selection of the initial antibody lead from the primary library. Such mutagenesis and selection of primary antibody leads effectively mimics the affinity maturation process naturally occurring in a mammal that produces antibodies with progressive increases in the affinity to an antigen.

In some embodiments of the invention, only the CDRH3 region is mutagenized. In some embodiments of the invention, the whole variable region is mutagenized. In some embodiments of the invention one or more of CDRH1, CDRH2, CDRH3, CDRL1, CDRL2, and/ CDRL3 may be mutagenized. In some embodiments of the invention, "light chain shuffling" may be used as part of the affinity maturation protocol. In certain embodiments, this may involve pairing one or more heavy chains with a number of light chains, to select light chains that enhance the affinity and/or biological activity of an antibody. In certain embodiments of the invention, the number of light chains to which the one or more heavy chains can be paired is at least about 2, 5, 10, 100, $10^3$, $10^4$, $10^5$, $10^6$, $10^7$, $10^8$, $10^9$, or $10^{10}$. In certain embodiments of the invention, these light chains are encoded by plasmids. In some embodiments of the invention, the light chains may be integrated into the genome of the host cell.

Coding sequences of antibody leads may be mutagenized using any of wide variety of methods. Examples of methods of mutagenesis include, but are not limited to site-directed mutagenesis, error-prone PCR mutagenesis, cassette mutagenesis, and random PCR mutagenesis. Alternatively or additionally, oligonucleotides encoding regions with the desired mutations can be synthesized and introduced into the sequence to be mutagenized, for example, via recombination or ligation.

Site-directed mutagenesis or point mutagenesis may be used to gradually change the CDR sequences in specific regions. For example, this may be accomplished by using oligonucleotide-directed mutagenesis or PCR. For example, a short sequence of an antibody lead may be replaced with a synthetically mutagenized oligonucleotide in either the heavy chain or light chain region, or both. Such a method may not be efficient for mutagenizing large numbers of CDR sequences, but may be used for fine tuning of a particular lead to achieve higher affinity toward a specific target protein.

Cassette mutagenesis may alternatively or additionally be used to mutagenize the CDR sequences in specific regions. In a typical cassette mutagenesis, a sequence block, or a region, of a single template is replaced by a completely or partially randomized sequence. However, the maximum information content that can be obtained may be statistically limited by the number of random sequences of the oligonucleotides. Similar to point mutagenesis, this method may also be used for fine tuning of a particular lead to achieve higher affinity towards a specific target protein.

Error-prone PCR, or "poison" PCR, may be used to mutagenize the CDR sequences, for example, by following protocols described in U.S. Pat. No. 6,153,745; Caldwell and Joyce, PCR Methods and Applications, 1992, 2: 28; Leung et al., Technique, 1989, 1: 11; Shafikhani et al., Biotechniques, 1997, 23: 304; and Stemmer et al., PNAS, 1994, 91: 10747 (each of which is incorporated by reference in its entirety).

Conditions for error prone PCR may include, for example, (a) high concentrations of $Mn^{2+}$ (e.g., about 0.4 to about 0.6 mM) that efficiently induces malfunction of Taq DNA polymerase; and/or (b) a disproportionally high concentration of one nucleotide substrate (e.g., dGTP) in the PCR reaction that causes incorrect incorporation of this high concentration substrate into the template and produces mutations. Alternatively or additionally, other factors such as, the number of PCR cycles, the species of DNA polymerase used, and the length of the template, may affect the rate of misincorporation of "wrong" nucleotides into the PCR product. Commercially available kits may be utilized for the mutagenesis of the selected antibody library, such as the "Diversity PCR random mutagenesis kit" (CLONTECH™).

Primer pairs used in PCR-based mutagenesis may, in certain embodiments, include regions matched with the homologous recombination sites in the expression vectors. Such a design allows facile re-introduction of the PCR products back into the heavy or light chain chassis vectors, after mutagenesis, via homologous recombination.

Other PCR-based mutagenesis methods can also be used, alone or in conjunction with the error prone PCR described above. For example, the PCR amplified CDR segments may be digested with DNase to create nicks in the double stranded DNA. These nicks can be expanded into gaps by other exonucleases such as Bal 31. Gaps may then be filled by random sequences by using DNA Klenow polymerase at a low concentration of regular substrates dGTP, dATP, dTTP, and dCTP with one substrate (e.g., dGTP) at a disproportionately high concentration. This fill-in reaction should produce high frequency mutations in the filled gap regions. Such methods of DNase digestion may be used in conjunction with error prone PCR to create a high frequency of mutations in the desired CDR segments.

CDR or antibody segments amplified from the primary antibody leads may also be mutagenized in vivo by exploiting the inherent ability of mutation in pre-B cells. The Ig genes in pre-B cells are specifically susceptible to a high-rate of mutation. The Ig promoter and enhancer facilitate such high rate mutations in a pre-B cell environment while the pre-B cells proliferate. Accordingly, CDR gene segments may be cloned into a mammalian expression vector that contains a human Ig enhancer and promoter. Such a construct may be introduced into a pre-B cell line, such as 38B9, which allows the mutation of the VH and VL gene segments naturally in the pre-B cells (Liu and Van Ness, Mol. Immunol., 1999, 36: 461, incorporated by reference in its entirety). The mutagenized CDR segments can be amplified from the cultured pre-B cell line and re-introduced back into the chassis-containing vector(s) via, for example, homologous recombination.

In some embodiments, a CDR "hit" isolated from screening the library can be re-synthesized, for example using degenerate codons or trinucleotides, and re-cloned into the heavy or light chain vector using gap repair.

Other Variants of Polynucleotide Sequences of the Invention

In certain embodiments, the invention provides a polynucleotide that hybridizes with a polynucleotide taught herein, or that hybridizes with the complement of a polynucleotide taught herein. For example, an isolated polynucleotide that remains hybridized after hybridization and washing under low, medium, or high stringency conditions to a polynucleotide taught herein or the complement of a polynucleotide taught herein is encompassed by the present invention.

Exemplary low stringency conditions include hybridization with a buffer solution of about 30% to about 35% formamide, about 1 M NaCl, about 1% SDS (sodium dodecyl sulphate) at about 37° C., and a wash in about 1× to about 2×SSC (20×SSC=3.0 M NaCl/0.3 M trisodium citrate) at about 50° C. to about 55° C.

Exemplary moderate stringency conditions include hybridization in about 40% to about 45% formamide, about 1 M NaCl, about 1% SDS at about 37° C., and a wash in about 0.5× to about 1×SSC at abut 55° C. to about 60° C.

Exemplary high stringency conditions include hybridization in about 50% formamide, about 1 M NaCl, about 1% SDS at about 37° C., and a wash in about 0.1×SSC at about 60° C. to about 65° C.

Optionally, wash buffers may comprise about 0.1% to about 1% SDS.

The duration of hybridization is generally less than about 24 hours, usually about 4 to about 12 hours.

Sublibraries and Larger Libraries Comprising Libraries or Sub-Libraries of the Invention Libraries comprising combinations of the libraries described herein (e.g., CDRH3 and CDRL3 libraries) are encompassed by the invention. Sublibraries comprising portions of the libraries described herein are also encompassed by the invention (e.g., a CDRH3 library in a particular heavy chain chassis or a sub-set of the CDRH3 libraries, for example based on length).

Moreover, libraries containing one of the libraries or sublibraries of the invention also fall within the scope of the invention. For example, in certain embodiments of the invention, one or more libraries or sublibraries of the invention may be contained within a larger library (theoretical or physical), which may include sequences derived by other means, for example, non-human or human sequence derived by stochastic or sitewise-stochastic synthesis. In certain embodiments of the invention, at least about 1% of the sequences in a polynucleotide library may be those of the invention (e.g., CDRH3 sequences, CDRL3 sequences, VH sequences, VL sequences), regardless of the composition of the other 99% of sequences. For the purposes of illustration only, one of ordinary skill in the art would readily recognize that a library containing $10^9$ total members, where $10^7$ members are members of the libraries of the invention (i.e., 1%) would have utility, and that members of the libraries of the invention could be isolated from such a library. In some embodiments of the invention, at least about 0.001%, 0.01%, 0.1%, 2%, 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% of the sequences in any polynucleotide library may be those of the invention, regardless of the composition of the other sequences. In some embodiments, the sequences of the invention may comprise about 0.001% to about 1%, about 1% to about 2%, about 2% to about 5%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, or about 95% to about 99% of the sequences in any polynucleotide library, regardless of the composition of the other sequences. Thus, libraries more diverse than one or more libraries or sublibraries of the invention, but yet still comprising one or more libraries or sublibraries of the invention, in an amount in which the one or more libraries or sublibraries of the invention can be effectively screened and from which sequences encoded by the one or more libraries or sublibraries of the invention can be isolated, also fall within the scope of the invention.

Alternative Scaffolds

As would be evident to one of ordinary skill in the art, the CDRH3 and/or CDRL3 polypeptides provided by the invention may also be displayed on alternative scaffolds. Several such scaffolds have been shown to yield molecules with specificities and affinities that rival those of antibodies. Exemplary alternative scaffolds include those derived from fibronectin (e.g., AdNectin), the β-sandwich (e.g., iMab), lipocalin (e.g., Anticalin), EETI-II/AGRP, BPTI/LACI-D1/ITI-D2 (e.g., Kunitz domain), thioredoxin (e.g., peptide aptamer), protein A (e.g., Affibody), ankyrin repeats (e.g., DARPin), γB-crystallin/ubiquitin (e.g., Affilin), $CTLD_3$ (e.g., Tetranectin), and $(LDLR-A\ module)_3$ (e.g., Avimers). Additional information on alternative scaffolds is provided, for example, in Binz et al., Nat. Biotechnol., 2005 23: 1257 and Skerra, Current Opin. in Biotech., 2007 18: 295-304, each of which is incorporated by reference in its entirety.

Additional Embodiments of the Invention

Library Sizes

In some embodiments of the invention, a library comprises about $10^1$ to about $10^{20}$ different polynucleotide or polypeptide sequences (encoding or comprising e.g., antibodies, heavy chains, CDRH3s, light chains, and/or CDRL3s). In some embodiments, the libraries of the invention are designed to include at least about $10^1$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$, or more different antibody, heavy chain, CDRH3, light chain, and/or CDRL3 polynucleotide or polypeptide sequences. In some embodiments, a library of the invention may contain less than a particular number of polynucleotide or polypeptide sequences, where the number of sequences is defined using any one of the integers provided above. In certain embodiments of the invention, a particular numerical range is defined, using any two of the integers provided above as lower and upper boundaries of the range, inclusive or exclusive. All combinations of the integers provided, which define an upper and lower boundary, are contemplated.

In some embodiments, the invention provides libraries wherein a fraction of the members of the library are members produced according to the methods, systems, and compositions provided herein. One important property of the libraries of the invention is that they favorably mimic certain aspects of the human preimmune repertoire, including length diversity and sequence diversity. One or ordinary skill in the art will readily recognize that libraries provided by the invention include libraries where a subset of the members of the library are members produced according to the methods, systems, and compositions provided herein. For example, a library containing $10^8$ members wherein $10^6$ members are produced according to the methods, systems, and compositions provided herein, would contain 1% sequences produced according to the methods, systems, and compositions provided herein. One of ordinary skill in the art would recognize that one or more of the $10^6$ members could readily be isolated using screening techniques known in the art. Therefore, said libraries fall within the scope of the invention. More specifically, libraries comprising at least about 1%, 2.5%, 5%, 10%, 15%, 20%, 25%, 30%, 40%, 45%, 50%, 55%, 60%, 65%, 70%, 75%, 80%, 85%, 90%, 95%, or 99% CDRH3, CDRL3, light chain, or heavy chain, and/or full-length antibody sequences provided herein fall within the scope of the invention. Libraries comprising at least about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ CDRH3, CDRL3, light chain, heavy chain, and/or full-length antibody sequences provided herein also fall within the scope of the invention.

Human Preimmune Set

In some embodiments, the invention comprises the set of 3,571 curated human preimmune antibody sequences contained within the HPS, their corresponding CDRH3 sequences (Appendix A), and/or a representation of these CDRH3 sequences (and/or TN1, DH, N2, and/or H3-JH segments thereof) in a computer readable format. In certain embodiments, the invention comprises a method of producing a CDRH3 library, the method comprising matching candidate segments (i.e., TN1, DH, N2, and H3-JH) from a theoretical segment pool with CDRH3 sequences in the HPS and/or any other repertoire of CDRH3 sequences. In some embodiments, the invention comprises the candidate segments from the theoretical segment pools disclosed herein and/or the segments selected for inclusion in a physical library.

Embodiments

While the methods described herein demonstrate the production of theoretical segment pools of H3-JH and DH segments using a limited number of allelic variants, one of ordinary skill in the art will recognize that methods taught herein may be applied to any IGHJ and IGHD genes, including any other allelic variants and all non-human IGHJ and IGHD genes. Alternatively or additionally, methods described herein may be applied to any reference set of CDRH3 sequences, for example to extract additional TN1 and/or N2 segments. Alternatively or additionally, one of ordinary skill in the art will recognize that each of the described embodiments of the invention may be in polynucleotide or polypeptide form, within a vector, virus, or microorganism (e.g., a yeast or bacteria). Furthermore, since the invention involves synthetic libraries that are fully enumerated, certain embodiments of the invention relate to any of the embodiments described above in a computer readable format, and uses thereof.

Non-human antibody libraries also fall within the scope of the invention.

The present disclosure describes the removal of sequences containing Cys residues, N-linked glycosylation motifs, deamidation motifs, and highly hydrophobic sequences from the libraries of the invention. One of ordinary skill in the art will recognize that one or more of these criteria (i.e., not necessarily all) can be applied to remove undesirable sequences from any library of the invention. However, libraries containing one or more of these types of sequences also fall within the scope of the invention. Other criteria can also be used; those described herein are not limiting.

In certain embodiments, the invention provides libraries in which the number of times a particular sequence is repeated within the library (either theoretical, synthetic, or physical realization) is limited. For example, in some embodiments, the invention provides libraries wherein the frequency of occurrence of any of the sequences in the library (e.g., CDRH3, CDRL3, heavy chain, light chain, full-length antibody) is less than about 2, 5, 10, 15, 20, 25, 30, 35, 40, 45, 50, 55, 60, 65, 70, 75, 80, 85, 90, 95, 100, 200, 300, 400, 500, 600, 700, 800, 900, or 1000. In some embodiments, the frequency of occurrence of any of the sequences in the library is less than a multiple of the frequency of occurrence of any other sequence in the library, for examples less than about 2, 5, 10, 15, 20, 25, 30, 35, 40, 45, 50, 55, 60, 65, 70, 75, 80, 85, 90, 95, 100, 200, 300, 400, 500, 600, 700, 800, 900, or 1000 times the frequency of occurrence of any other sequence in the library.

In some embodiments, libraries are defined by the combinatorial diversity of the segments used to produce CDRH3 sequences, in particular the number of non-degenerate segment combinations that can be used to produce a particular CDRH3 sequence. In some embodiments, this metric may be calculated using, for example, a sample of about 2000, 5000, 10000, 20000, 50000, 100000, or more sequences from the CDRH3 library and "self-matching" using the segments used to generate the CDRH3 sequences of that library. In certain embodiments, the invention provides libraries wherein at least about 95%, 90%, 85%, 80%, 75%, 70%, 65%, 60%, 55%, 50%, 45%, 40%, 35%, 30%, 25%, 20%, 15%, 10%, or 5% of the CDRH3 sequences in the library may be formed by a single combination of segments.

In certain embodiments of the invention, a statistical bootstrap analysis was used to generate CDRH3 reference sets. While it may be advantageous to use this method, it is not required for every embodiment of the invention.

In some embodiments, the invention provides methods and systems of selecting polynucleotides to encode polypeptides of the invention, comprising selecting polynucleotide segments lacking (or containing) certain restriction sites individually and/or after combinatorial concatenation with other segments (e.g., see Example 9.3.7).

The exemplary libraries provided herein are not limiting and provided for exemplification only.

EXAMPLES

This invention is further illustrated by the following examples which should not be construed as limiting. The contents of all references, patents and published patent applications cited throughout this application are hereby incorporated by reference.

In general, the practice of the present invention employs, unless otherwise indicated, conventional techniques of chemistry, molecular biology, recombinant DNA technology, PCR technology, immunology (especially, e.g., antibody technology), expression systems (e.g., yeast expression, cell-free expression), phage display, ribosome display, and PROFUSION™), and any necessary cell culture that are within the skill of the art and are explained in the literature. See, e.g., Sambrook, Fritsch and Maniatis, *Molecular Cloning: Cold Spring Harbor Laboratory Press* (1989); *DNA*

Cloning, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols* (Methods in Molecular Biology), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); *Current Protocols in Molecular Biology*, eds. Ausubel et al., John Wiley & *Sons* (1992); *Large-Scale Mammalian Cell Culture Technology*, Lubiniecki, A., Ed., Marcel Dekker, Pub., (1990); *Phage Display: A Laboratory Manual*, C. Barbas (Ed.), CSHL Press, (2001); *Antibody Phage Display*, P O'Brien (Ed.), Humana Press (2001); Border et al., Nature Biotechnology, 1997, 15: 553; Border et al., Methods Enzymol., 2000, 328: 430; ribosome display as described by Pluckthun et al. in U.S. Pat. No. 6,348,315, and Profusion™ as described by Szostak et al. in U.S. Pat. Nos. 6,258,558; 6,261,804; and 6,214,553; and bacterial periplasmic expression as described in US20040058403A1. Each of the references cited in this paragraph is incorporated by reference in its entirety.

Further details regarding antibody sequence analysis using Kabat conventions and programs to analyze aligned nucleotide and amino acid sequences may be found, e.g., in Johnson et al., Methods Mol. Biol., 2004, 248: 11; Johnson et al., Int. Immunol., 1998, 10: 1801; Johnson et al., Methods Mol. Biol., 1995, 51: 1; Wu et al., Proteins, 1993, 16: 1; and Martin, Proteins, 1996, 25: 130. Each of the references cited in this paragraph is incorporated by reference in its entirety.

Further details regarding antibody sequence analysis using Chothia conventions may be found, e.g., in Chothia et al., J. Mol. Biol., 1998, 278: 457; Morea et al., Biophys. Chem., 1997, 68: 9; Morea et al., J. Mol. Biol., 1998, 275: 269; Al-Lazikani et al., J. Mol. Biol., 1997, 273: 927. Bane et al., Nat. Struct. Biol., 1994, 1: 915; Chothia et al., J. Mol. Biol., 1992, 227: 799; Chothia et al., Nature, 1989, 342: 877; and Chothia et al., J. Mol. Biol., 1987, 196: 901. Further analysis of CDRH3 conformation may be found in Shirai et al., FEBS Lett., 1999, 455: 188 and Shirai et al., FEBS Lett., 1996, 399: 1. Further details regarding Chothia analysis are described, for example, in Chothia et al., Cold Spring Harb. Symp. Quant Biol., 1987, 52: 399. Each of the references cited in this paragraph is incorporated by reference in its entirety.

Further details regarding CDR contact considerations are described, for example, in MacCallum et al., J. Mol. Biol., 1996, 262: 732, incorporated by reference in its entirety.

Further details regarding the antibody sequences and databases referred to herein are found, e.g., in Tomlinson et al., J. Mol. Biol., 1992, 227: 776, VBASE2 (Retter et al., Nucleic Acids Res., 2005, 33: D671); BLAST (world wide web at ncbi.nlm.nih.gov/BLAST/); CDHIT (bioinformaticslj crfedu/cd-hi/); EMBOSS (world wide web at hgmp.mr-c.ac.uk/Software/EMBOSS/); PHYLIP (evolution.genetics.washington.edu/phylip.html); and FASTA (fasta.bioch.virginia.edu). Each of the references cited in this paragraph is incorporated by reference in its entirety.

Light Chain Libraries

Example 1. Light Chain Libraries with Framework and/or CDRL1 and/or CDRL2 Variability Although the diversity in antibody sequences is concentrated in the CDRs, certain residues in the framework regions can also influence antigen recognition and/or modulate affinity (Queen et al., Proc. Natl. Acad. Sci. USA, 1989, 86: 10029; Carter et al., Proc. Natl. Acad. Sci. USA, 1992, 89: 4285, each incorporated by reference in its entirety). These residues have been cataloged and used to make framework substitutions that improve antibody affinity, for example, during the process of antibody humanization (e.g., see the "Vernier" residues in Foote and Winter, J. Mol. Biol., 1992, 224: 487, incorporated by reference in its entirety). In the heavy chain, the Vernier residues include Kabat-numbered residues 2, 27-30, 47-49, 67, 69, 71, 73, 78, 93-94, and 103. In the light chain, the Vernier residues include Kabat residues 2, 4, 35-36, 46-49, 64, 66, 68-69, 71, and 98. The Vernier residue numbers are the same for kappa and lambda light chain sequences (see Table 4 in Chothia et al., J. Mol. Biol., 1985, 186: 651, which is incorporated by reference in its entirety). Additionally, framework positions at the VL-VH interface may also influence affinity. In the heavy chain, the interface residues include Kabat residues 35, 37, 39, 45, 47, 91, 93, 95, 100, and 103 (Chothia et al., J. Mol. Biol., 1985, 186: 651, incorporated by reference in its entirety). In the light chain, the interface residues include Kabat residues 34, 36, 38 44, 46, 87, 89, 91, 96, and 98.

The following procedure was used to select the framework residues to be varied and the amino acids to which they should be varied:
a. A collection of human VK light chain DNA sequences was obtained from NCBI (see Appendix A of WO/2009/036379 for GI Nos.). These sequences were classified according to the germline origin of their VK germline segment.
b. Patterns of variation at each of the Vernier and interface positions were examined as follows:
  i. Equation 1 (from Makowski & Soares, Bioinformatics, 2003, 19: 483, incorporated by reference in its entirety) was used to calculate a diversity index for the Vernier positions, interface positions, CDRL1, and CDRL2.

$$d = \frac{1}{N \sum p_i^2} \qquad \text{Equation 1}$$

Here, d is the diversity index, N is 20, the total number of amino acid types, and $p_i$ is the fraction of amino acid of type "i" at the position of interest. The sum is carried out over the 20 amino acid types. The parameter d will attain its minimum value of 0.05 or 1/20, when a single amino acid type is observed at a given position: $p_i$ is 1 for one type and zero for all the rest. Conversely, when all the amino acid types are equally probable (e.g., $p_i$ is 0.05 for all i), d will attain its maximum value of 1.0.
  ii. The diversity index for each of the Vernier and interface positions were compared to the diversity index for the positions in CDRL1 and CDRL2.
  iii. The interface positions were found to be relatively invariant, with d values very close to the minimum of 0.05, and were thus not altered. The Vernier residues with a diversity index comparable to or larger than that of the CDR positions (i.e., at or above 0.07 for the particular example provided in FIG. 1) were selected as candidates for variance (see FIG. 1). The amino acid residues included in these positions were selected from amongst the two to three amino acids most frequently occurring in that position in the sequences in the collection of human VK light chains, for each particular VK germline.

iv. Table 2 shows the positions selected for variance in each of nine exemplified light chain germlines. The alternative framework positions represent positions with a diversity index less than the primary framework positions, but where variability may still be incorporated to influence antigen binding.

v. The amino acid residues in the framework positions selected for variance were varied as follows (Table 3 provides the polypeptide sequences of these variants):
  1. Position 2: Germline I was optionally changed to V.
  2. Position 4: Germline M or L was optionally changed to L or M. In some embodiments, changes from M to L, but not the reverse, may be preferred, because M may undergo oxidation during production, processing, or storage, potentially altering the properties of the antibody.
  3. Position 36: Germline Y was optionally changed to F and H.
  4. Position 46: Germline L was optionally changed to V.
  5. Position 48: Germline I was optionally changed to L.
  6. Position 49: Germline Y was optionally changed to S, F, and H.
  7. Position 66: Germline G was optionally changed to R and E.

One of ordinary skill in the art would readily recognize that the procedure outlined above could also be used to select positions to vary in Vλ germline sequences, and that libraries containing Vλ chains also fall within the scope of the invention.

In addition to the framework mutations, variability was also introduced into CDRL1 and CDRL2. This was performed by determining which residues in CDRL1 and CDRL2 were variable, within a particular germline, in the VK dataset used above and incorporating the most frequently occurring 2 to 4 variants into CDRL1 and CDRL2 in the synthetic libraries of the invention. With the exception of position 50 of CDRL2 of the VK1-5 germline, these alternatives did not arise from allelic variation. Table 3 shows the polypeptide sequences of nine light chain chassis and their framework and CDR L1/L2 variants for the currently exemplified embodiment of the invention. The amino acid residues in the CDRL1/L2 positions selected for variance were varied as follows (using the Chothia-Lesk numbering system; Chothia and Lesk, J. Mol. Biol., 1987, 196: 901):
  1. Position 28: Germline S or G were optionally changed to G, A, or D.
  2. Position 29: Germline V was optionally changed to I.
  3. Position 30: Germline S was optionally changed to N, D, G, T, A, or R.
  4. Position 30A: Germline H was optionally changed to Y
  5. Position 30B: Germline S was optionally changed to R or T.
  6. Position 30E: Germline Y was optionally changed to N.
  7. Position 31: Germline S was optionally changed to D, R, I, N, or T.
  8. Position 32: Germline Y or N were optionally changed to F, S, or D.
  9. Position 50: Germline A, D, or G were optionally changed to G, S, E, K, or D.
  10. Position 51: Germline G or A were optionally changed to A, S, or T.
  11. Position 53: Germline S or N were optionally changed to N, H, S, K, or R.
  12. Position 55: Germline E was optionally changed to A or Q.

Example 2. Light Chain Libraries with Enhanced Diversity in CDRL3

Figure 2:
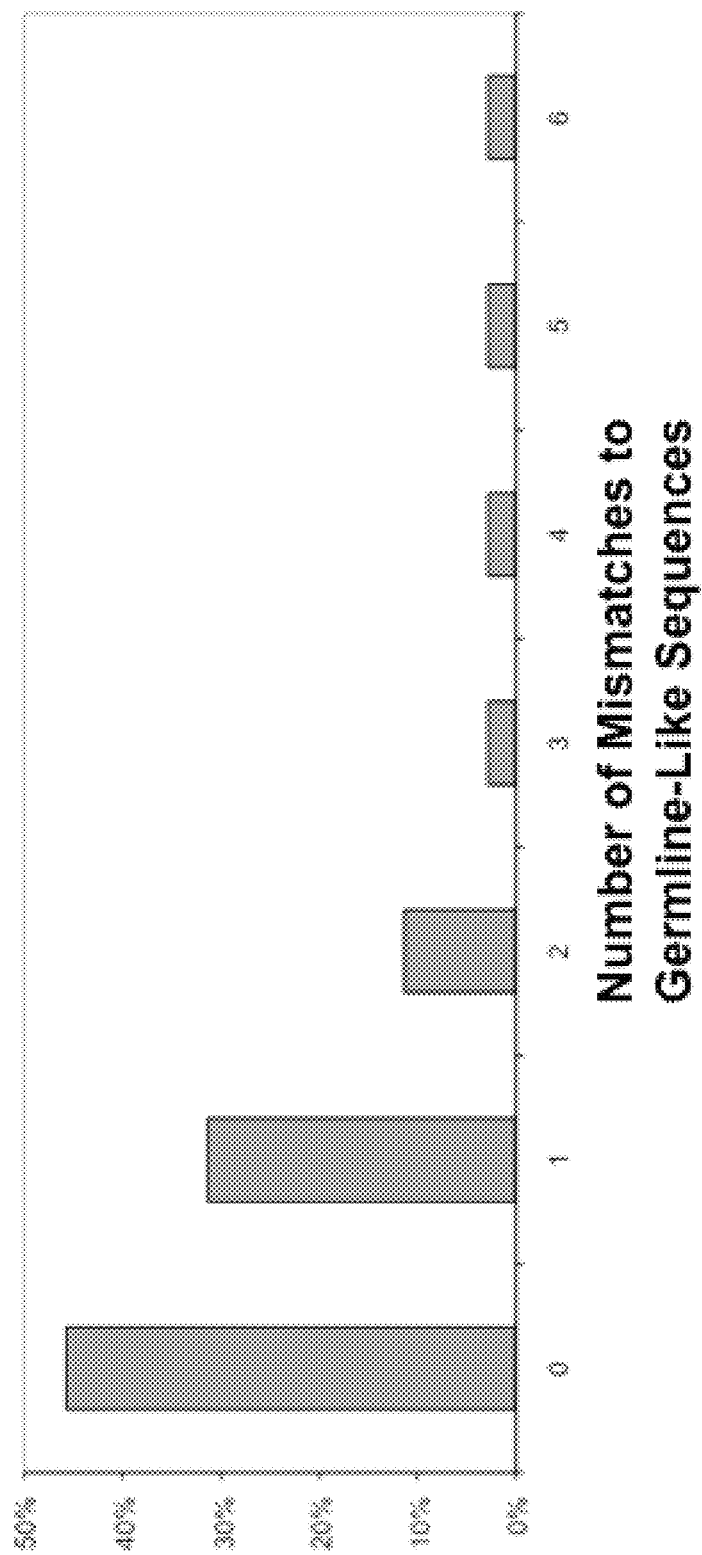
FIG. 2 shows that clinically validated CDRL3 sequences deviate little from germline-like sequences (n=35).

A variety of methods of producing light chain libraries are known in the art (e.g., see U.S. Publication Nos. 2009/0181855, 2010/0056386, and WO/2009/036379). An analysis of clinically validated antibody sequences indicated that these sequences have very little deviation from germline-like VL-JL (where "L" can be a kappa or lambda germline sequence) rearrangements prior to somatic mutation (FIG. 2). Here, a germline-like rearrangement is one where neither the V nor J portion differ from the respective germline genes and, for the purposes of this particular example, where the length of CDRL3 is restricted to 8, 9 or 10 amino acids (see U.S. Publication Nos. 2009/0181855, 2010/0056386, and WO/2009/036379). For the IGHJK1 gene, however, both WT (Trp-Thr) and RT (Arg-Thr) sequences (the first two N-terminal residues) are considered "germline-like" and so are full L3 rearrangements containing such sequences. Therefore, new light chain libraries were designed and constructed with the objectives of simultaneously (1) minimizing deviation from germline-like sequences, as defined above; and (2) generating maximal diversity. In particular, the overarching goal was to maximize the type of diversity that is indicated to be most favorable by clinically validated antibody sequences. In particular, the designed library sought to maximize the diversity of CDRL3 sequences that differ from length-matched germline sequences by two amino acids or fewer.

This was accomplished by utilizing a "jumping dimer" or "jumping trimer" approach to light chain oligonucleotide design. The jumping dimer approach involves the incorporation of degenerate codons at each of the six positions of CDRL3 encoded by the VL segment (L3-VL). At most two positions vary from germline in each individual L3-VL sequence, but the two positions do not have to be adjacent to one another. Thus, the total number of designed degenerate oligonucleotides synthesized per VL chassis is 6!/(4!2!), or fifteen (accounting for six of the most commonly occurring amino acids at the junction (position 96) between VL and JL for each kappa germline chassis (namely F, L, I, R, W, Y, and P; see U.S. Publication Nos. 2009/0181855 and 2010/0056386, and WO/2009/036379, each of which is incorporated by reference in its entirety, for more details on the junctional amino acids at position 96). The jumping trimer approach is analogous to the jumping dimer approach, but with three positions varying from germline in each individual L3-VL sequence, instead of two as in the jumping dimer. The degenerate codons selected for each position in the jumping dimer and trimer approaches were chosen to (1) reproduce the diversity contained in the known repertoire of publicly available human VK sequences (see Appendix A of WO/2009/036379); and (2) to minimize or eliminate undesirable sequences within the CDRL3s of the resulting synthetic light chains, such as N-linked glycosylation motifs (NXS/NXT), Cys residues, stop codons, and deamidation-prone NG motifs. Table 4 shows the fifteen degenerate oligonucleotides encoding the VK1-39 CDRL3 sequences with a length of nine amino acids and F or Y as the junctional amino acid, and the corresponding degenerate polypeptide sequences. Table 5, Table 6, and Table 7 provide the oligonucleotide sequences for each of the VK sequences of the exemplary jumping dimer and trimer libraries, for CDRL3 lengths of 8, 9, and 10, respectively, and the sequences for the corresponding CDRL3s.

The number of unique CDRL3 sequences within each germline library was then enumerated and compared to the number of unique CDRL3 sequences in a different light chain library, designated "VK-v1.0" (see Example 6.2 in US Publication No. 2009/0181855), for each of the three lengths. Table 8 provides the number of unique CDRL3 sequences in each of the respective germline libraries.

Figure 3:
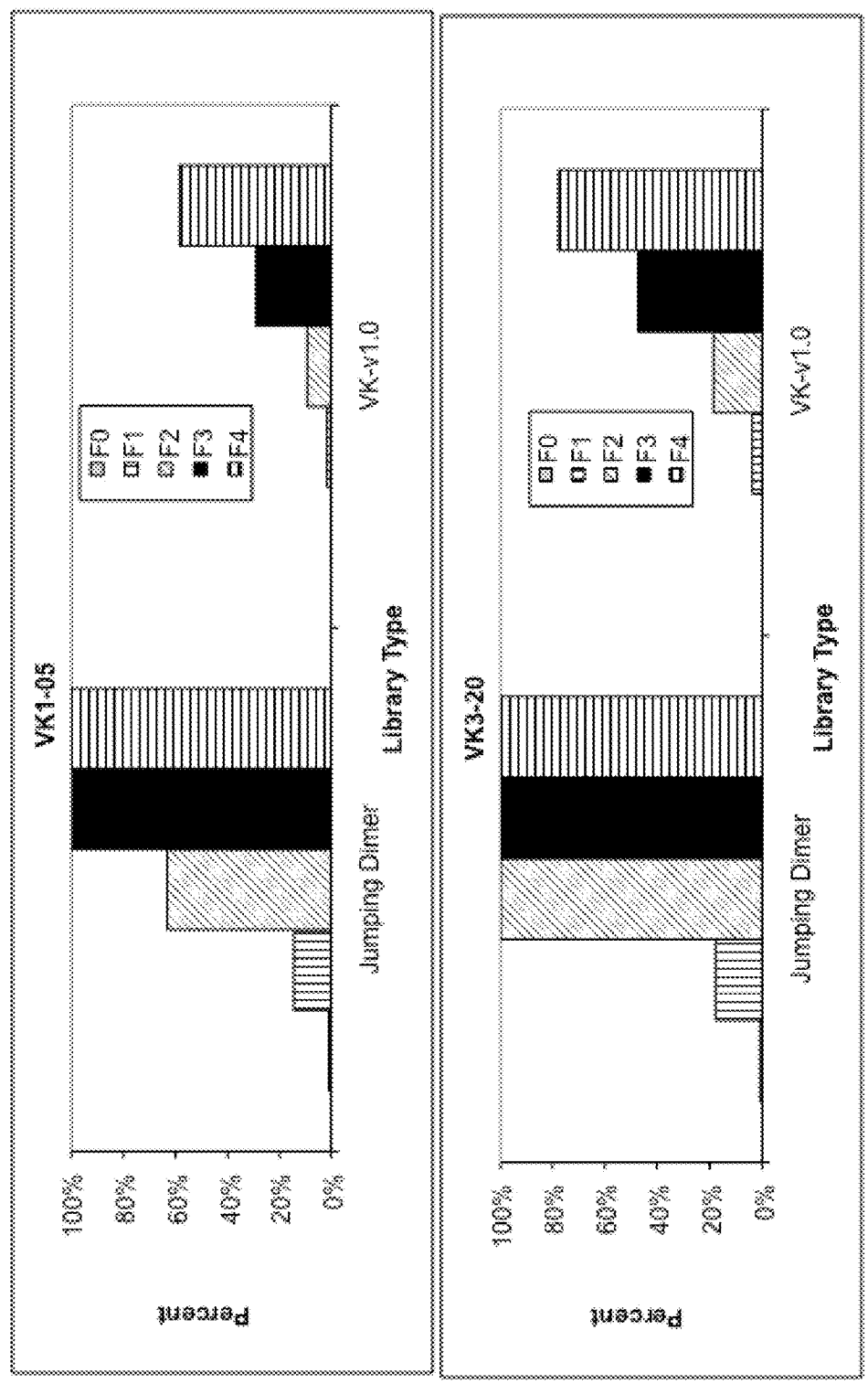
FIG. 3 shows the percent of sequences in the jumping dimer CDRL3 libraries of the invention and a previous CDRL3 library, VK-v1.0, with X or fewer mutations from germline. Here, FX is the percentage of sequences in a library with X or fewer mutations from germline.

FIG. 3 provides the percentage of sequences in the jumping dimer and VK-v1.0 libraries with CDRL3 length of nine amino acids that contain no mutations from germline-like sequences (Table 1) or 1, 2, 3, or 4 or fewer mutations from germline-like sequences. Naturally-occurring VK1-05 sequences are almost as likely to have Ser (germline amino acid type) as Pro at Kabat position 95, thus both residues (S and P) were incorporated in the synthetic libraries representing VK1-05 repertoires. However, as indicated in Table 1, only Ser was considered to be a germline-like residue at position 95 for the purposes of this analysis when the VK gene is VK1-05. The plot for VK3-20 is representative of the remaining chassis in the library for a length nine. All of the sequences in the VK1-05 library were within three amino acids of human germline sequences, and approximately 63% of the sequences were within two amino acids of human germline-like sequences. For the rest of the libraries, and as designed, 100% of the sequences were within two amino acids of human germline-like sequences; thus, over 95% of the sequences of length 9 in the jumping dimer library considered as a whole were within 2 amino acids of germline-like sequences. By comparison, only 16% of the members of the VK-v1.0 libraries of length nine amino acids are within two amino acids of the corresponding human germline-like sequences. For length 8, about 98% of the sequences in the jumping dimer libraries were within two amino acids of germline-like, versus about 19% for VK-v1.0. For length 10, more than 95% of the sequences of the jumping dimer library were within two amino acids of germline-like, versus about 8% for VK-v1.0.

In some embodiments, to concentrate the diversity in positions most likely to be solvent-exposed in the folded antibody, positions 89 and 90 (Kabat numbering) are not modified from germline—these are most often QQ, but the sequence is MQ for the VK2-28 chassis. Other VK germline genes have different sequences at positions 88-89, and the use of these genes as chassis also falls within the scope of the invention. For example, VK1-27 has QK, VK1-17 and VK1-6 both have LQ, and so on. The sequences in these positions are known in the art and can be obtained, for example, from Scaviner et al., Exp. Clin. Immunogenet., 1999, 16: 234 (see FIG. 2), which is incorporated by reference in its entirety.

CDRH3 Libraries

The following examples describe methods and compositions useful for the design and synthesis of antibody libraries with improved CDRH3 sequences in comparison to libraries known in the art. The CDRH3 sequences of the invention have enhanced diversity in comparison to libraries known in the art, while retaining the character of human sequences, improving combinatorial efficiency of the synthetic CDRH3 segments, and/or improving the matching between synthetic CDRH3 sequences and human CDRH3 sequences in one or more reference sets.

Example 3. Generating a Curated Reference Set of Human Preimmune CDRH3 Sequences A file containing approximately 84,000 human and mouse heavy chain DNA sequences was downloaded from the BLAST public resource (ftp.ncbi.nih.gov/blast/db/FASTA/; filename: igSeqNt.gz; download date: Aug. 29, 2008). Of these approximately 84,000 sequences, approximately 34,000 sequences were identified as human heavy chain sequences based on analysis of the sequence header annotation. These sequences were then filtered as follows: First, all sequences were classified, via their VH-region, according to their corresponding (closest matched) VH germline. Sequences that were of an incorrect or insufficient length, or that could not be matched due to extensive mutation, were discarded. Second, any sequences containing more than five mutations, at the DNA level, when compared to their corresponding germline VH sequence were also discarded. It was assumed, consistent with Rada and Milstein, EMBO J., 2001, 20: 4570, that mutations (or lack thereof) in the N-terminal portion of the variable region may be used as conservative surrogates for mutations (or lack thereof) in the C-terminal portion of the variable region, in particular in CDRH3. Therefore, selecting only sequences with five or fewer nucleotide mutations in VH, which is N-terminal to CDRH3 is highly likely to also select for CDRH3 sequences that are either lightly mutated or not mutated at all (i.e., having preimmune character).

After translating the remaining DNA sequences into their amino acid counterparts, the appropriate reading frame containing the heavy chain germline amino acid sequence was identified and used to identify the sequences of the CDRs, including that of the CDRH3. The list of CDRH3 sequences obtained at this point was further filtered to eliminate members that did not differ from any other sequence in the set by at least three amino acids (after matching for length). This process yielded 11,411 CDRH3 sequences, with 3,571 sequences annotated as originating from healthy adults ("Healthy Preimmune Set" or "HPS"; see Appendix A for GI Nos.) and the other 7,840 sequences annotated as originating from individuals suffering from disease, of fetal origin, or of antigen-specific origin. The methods described below were then used to deconvolute each of the sequences in the HPS into the four segments that constitute the CDRH3: (1) TN1, (2) DH, (3) N2, and (4) H3-JH.

Example 4. Method to Match Segments from a Theoretical Segment Pool to CDRH3s in a Reference Set This example describes the method used to identify the TN1, DH, N2, and H3-JH segments of the CDRH3s in the HPS. The currently exemplified approach to the design and synthesis of human CDRH3 sequences mimics the segmental V-D-J gene recombination processes by which the human immune system generates the preimmune CDRH3 repertoire. The matching method described here determines which TN1, DH, N2 and H3-JH segments have been used to produce a particular CDRH3 across a reference set of CDRH3s (e.g., the HPS). This information is then used, optionally in conjunction with other information described below (e.g., physicochemical properties), to determine which TN1, DH, N2, and H3-JH segments from a theoretical segment pool (or segments extracted from the CDRH3 sequences in the reference set, in the case of the TN1 and N2) should be included in a synthetic CDRH3 library.

The inputs to the matching method are: (1) a reference set of CDRH3 sequences (e.g., the human CDRH3 sequences in the HPS), and (2) a theoretical segment pool, containing a plurality of TN1, DH, N2 and/or H3-JH segments. Methods by which the members of the theoretical segment pool are generated are more fully described below. For each CDRH3 in the reference set, the matching method generates two outputs: (i) a list of the closest matched CDRH3 sequences that can be generated using the segments of the theoretical segment pool, and (ii) the one or more segment combinations from the theoretical segment pool that can be used to create these closest matched CDRH3 sequences.

The matching method was performed as follows: Each TN1 segment in the theoretical segment pool was aligned at its first amino acid with the first amino acid (position 95) of the CDRH3 sequence from the reference set. For each segment length, all (i.e., one or more) of the segments returning the best matches are retained, and the remaining segments are discarded. The retained TN1 segments are then concatenated with all DH segments from the theoretical segment pool, to create [TN1]-[DH] segments. These segments are then aligned as above, and all the best matches for each of the [TN1]-[DH] segments are retained. The procedure is repeated with [TN1]-[DH]-[N2] and [TN1]-[DH]-[N2]-[H3-JH] segments until the length of the CDRH3 sequence from the reference set is identically recapitulated by the segment combinations from the theoretical segment pool. All segment combinations returning the best match to the CDRH3s in the reference set are retained as the output of the matching method.

Table 9 provides an example of the output of the matching method, specifically the output for four individual sequences from the HPS, using a theoretical segment pool designated "Theoretical Segment Pool 1," or "TSP1". TSP1 contains several theoretical segment pools, namely: 212 TN1 segments (Table 10), 1,111 DH segments (Table 11), 141 N2 segments (Table 12), and 285 H3-JH segments (Table 13). The CDRH3 sequence in Test Case 1 contains an identical match in TSP1 that is reached via a unique combination of the four segments. Test Cases 2.1 and 2.2 each return an identical match, but via two distinct combinations that differ in the TN1 and DH segments. In Test Cases 3.1, 4.1, and 4.2, the closest matches are all a single amino acid away from the reference CDRH3, and can be reached via one (3.1) or two (4.1 and 4.2) combinations of segments from TSP1. This approach can be generalized to find all of the closest matches to any reference CDRH3 sequence within any theoretical segment pool and all combinations of the segments within the theoretical segment pool that can produce the reference CDRH3 sequence exactly and/or its closest matches.

Example 5. Deriving Theoretical Segment Pools of H3-JH Segments

In order to produce theoretical segment pools of H3-JH segments for consideration for inclusion in a synthetic CDRH3 library, the following method was applied to generate mutants of seven (IGHJ1-01, IGHJ2-01, IGHJ3-02, IGHJ4-02, IGHJ5-02, IGHJ6-02 and IGHJ6-03) of the twelve germline IGHJ sequences of Table 14. These seven alleles were chosen because they were among the most commonly occurring alleles in human sequences. Libraries where all sequences of Table 14 (some differing only in FRM4) are used to generate H3-JH and/or JH (i.e., H3-JH and FRM4) also fall within the scope of the invention. The method is intended to simulate the creation of junctional diversity during the V-D-J recombination process in vivo, which occurs via enzyme-mediated addition and deletion of nucleotides to the germline gene segments. The method proceeds as follows, and results in a fully enumerated theoretical segment pool of H3-JH segments:

1. A pre-treatment was applied to the IGHJ genes that contain a partial codon consisting of two nucleotide bases at their 5' terminus (IGHJ3-02, IGHJ4-02, IGHJ5-02, IGHJ6-02 and IGHJ6-03), prior to the first nucleotide encoding the translation of the JH segment that produces the well-known JH framework regions. For example, the IGHJ3-02 gene contains an AT dinucleotide sequence prior to the first nucleotide encoding the translation of the JH segment that produces the JH framework region (FIG. 4, top). All partial codons consisting of two nucleotide bases were completed, using all possible nucleotide doublets (i.e., NN) at their two most 5' positions (FIG. 4, top, second row for IGHJ3-02). More specifically, the most 5' nucleotide in the germline sequence was mutated to N and an additional N was added 5' to that nucleotide.
2. IGHJ genes IGHJ1-01 (FIG. 4, center) and IGHJ2-01 (FIG. 4, bottom) contain zero and one nucleotide base(s) at their 5' termini, prior to the first nucleotide encoding the translation of the JH segment that produces the JH framework region. For these genes, the pre-treatment described in step 1 was not performed. Instead, the 5' doublets were mutated to NN (FIG. 4, middle and bottom, second row of each). Therefore, after performing this step, each of the seven IGHJ genes enumerated above was converted to a variant with an NN doublet as its first two 5' positions.
3. The 5' codons of the sequences produced via steps 1 and 2 were then deleted, and the first two bases of the resulting DNA sequence were subsequently mutated to an NN doublet (FIG. 4, rows 3-4 for all).
4. The 5' codons of the sequences produced in step 3 were then deleted, and the first two bases of the resulting DNA sequence were subsequently mutated to an NN doublet (FIG. 4, rows 5-6 for all).
5. Each of the polynucleotide sequences generated by steps (1)-(4) were then translated, to obtain a theoretical segment pool consisting of 248 parent H3-JH polypeptide segments (Table 15) from the reading frame for each sequence that produced the JH framework region.
6. The parent H3-JH polypeptide segments were truncated at their N-termini, by removing one amino acid at a time until only the portion of the JH segment comprising FW4 remains (i.e., an H3-JH segment with a length of zero amino acids).

The methods described above resulted in the production of a theoretical segment pool of 285 H3-JH segments (Table 13).

Example 6. Deriving Theoretical Segment Pools of DH Segments

Two theoretical pools of DH segments were generated, using one or more of two translation methods, designated "Translation Method 0" (TM0), or "Translation Method 1" ("TM1"), each performed in the three forward reading frames of 27 human germline IGHD DNA sequences or segments derived therefrom (Table 16).

The 1K DH Theoretical Segment Pool (1K DH)

TM1 was used to generate the "1K DH Theoretical Segment Pool" ("1K DH"; see the 1,111 DH segments of Table 11). In TM1, IGHD sequences that had a partial codon containing two untranslated bases after translation in any of the three forward reading frames were completed to produce a full codon only if the two bases could encode only a single amino acid upon completion. For example, a DNA sequence such as TTA-GCT-<u>CG</u> has two full codons that would be translated to LA, and a remaining partial codon (<u>CG</u>) that can only encode R, as any of CGA, CGC, CGG, or CGT will encode R. Thus, applying TM1 to this sequence will yield LAR. For sequences with partial codons that could encode more than one amino acid (e.g., GA or AG), the partial codons were ignored. Applying TM1 to the 27 IGHD sequences of Table 16 generated a theoretical segment pool containing the 73 DH parent segments of Table 17 (some containing stop codons ("Z") and unpaired Cys residues). These sequences were then progressively deleted at the amino acid level, at their N- and C-termini, until only two amino acids remained. Truncated segments were discarded if they contained a stop codon, unpaired Cys residues, N-linked glycosylation motifs, or deamidation motifs. This process yielded the 1,111 DH segments of Table 11.

The 68K DH Theoretical Segment Pool (68K DH)

The 27 IGHD genes and alleles of Table 16 were progressively deleted on either or both of their 5' and 3' ends until four bases remained, yielding 5,076 unique polynucleotide sequences of four or more nucleotides. These 5,076 sequences were subjected to systematic addition of 0, 1 and/or 2 N nucleotides their 5' and/or 3' ends. The resulting sequences were translated using TM0. In TM0, only full codons are translated; partial codons (i.e., 1 or 2 bases) are ignored. This method yielded 68,374 unique DH polypeptide segments after elimination of segments with stop codons, unpaired Cys residues, Asn in the last or next to last position that can lead to N-linked glycosylation motifs, and deamidation motifs (the "68K DH Theoretical Segment Pool"). Using the IGHD genes of Table 16 as an input for the PYTHON computer code provided below will reproduce the exact theoretical segment pool of 68,374 DH segments. There are two free parameters in this program: (1) the minimum length of the DNA sequences remaining after progressive deletions (4 bases in this example), and (2) the minimum length of the peptide sequences (2 amino acids in this example) acceptable for inclusion in the theoretical segment pool. These parameters can be changed to alter the output of the program. For example, changing the first parameter to one base and the second parameter to one amino acid would lead to a larger theoretical segment pool with 68,396 unique sequences, including 18 single-amino acid segments. DH segments progressively truncated to different lengths also fall within the scope of the invention; for example those truncated to 1, 2, 3, or 4 or more amino acids, or 1, 2, 3, 4, 5, 6, 7, 8, 9, 10, or more nucleotides prior to translation.

PYTHON Computer Program to Generate 68,374 DH Segments

```
import math, sys, string
class genes:
    name = 'x'
    seq = 'x'
    progdel = set( )
```

PYTHON Computer Program to Generate 68,374 DH Segments

```
class table:
    name = 'x'
    dna = 'x'
    dna_n = 20 * ['x']
    prot = 60 * ['x']
    uprot = set( )
pepcod = { 'A':0, 'C':1, 'D':2, 'E': 3, 'F': 4, 'G': 5, 'H': 6,
'I':7, 'K':8, 'L': 9, 'M': 10,
'N':11, 'P':12, 'Q':13, 'R': 14, 'S': 15, 'T': 16, 'V':17,
'W':18, 'Y': 19, 'Z': 20}
codpep = 21 * ['']
codpep [0] = 'A'
codpep [1] = 'C'
codpep [2] = 'D'
codpep [3] = 'E'
codpep [4] = 'F'
codpep [5] = 'G'
codpep [6] = 'H'
codpep [7] = 'I'
codpep [8] = 'K'
codpep [9] = 'L'
codpep [10] = 'M'
codpep [11] = 'N'
codpep [12] = 'P'
codpep [13] = 'Q'
codpep [14] = 'R'
codpep [15] = 'S'
codpep [16] = 'T'
codpep [17] = 'V'
codpep [18] = 'W'
codpep [19] = 'Y'
# Z represents a stop codon
codpep [20] = 'Z'
bases = 'ACGT'
def translate_dna(sequence):
# Translation of input DNA sequence using standard genetic code
# Only full codons are considered with any remaining 1 or 2 bp
being ignored
# Z represents a stop codon
    code = {
        'ATA':'I', 'ATC':'I', 'ATT':'I', 'ATG':'M',
        'ACA':'T', 'ACC':'T', 'ACG':'T', 'ACT':'T',
        'AAC':'N', 'AAT':'N', 'AAA':'K', 'AAG':'K',
        'AGC':'S', 'AGT':'S', 'AGA':'R', 'AGG':'R',
        'CTA':'L', 'CTC':'L', 'CTG':'L', 'CTT':'L',
        'CCA':'P', 'CCC':'P', 'CCG':'P', 'CCT':'P',
        'CAC':'H', 'CAT':'H', 'CAA':'Q', 'CAG':'Q',
        'CGA':'R', 'CGC':'R', 'CGG':'R', 'CGT':'R',
        'GTA':'V', 'GTC':'V', 'GTG':'V', 'GTT':'V',
        'GCA':'A', 'GCC':'A', 'GCG':'A', 'GCT':'A',
        'GAC':'D', 'GAT':'D', 'GAA':'E', 'GAG':'E',
        'GGA':'G', 'GGC':'G', 'GGG':'G', 'GGT':'G',
        'TCA':'S', 'TCC':'S', 'TCG':'S', 'TCT':'S',
        'TTC':'F', 'TTT':'F', 'TTA':'L', 'TTG':'L',
        'TAC':'Y', 'TAT':'Y', 'TAA':'Z', 'TAG':'Z',
        'TGC':'C', 'TGT':'C', 'TGA':'Z', 'TGG':'W',
    }
    proteinseq = ''
    for n in range(0, len(sequence), 3):
        if code.has_key(sequence [n:n+3]) == True:
            proteinseq += code [sequence [n:n+3]]
    return proteinseq
# main body starts here
# open input and output files
in1 = open(sys.argv [1], 'r')
ou1 = open(sys.argv [2], 'w')
# read DNA sequences for input DH segments
data = in1.readlines( )
nseg = len(data)
seqs = [ genes( ) for i in range(nseg) ]
for i in range(nseg):
    line = data [i]
    words = string.split(line)
    seqs [i].name = words[0]
    seqs [i].seq = words[1]
    seqs [i].progdel = set( )
# Define here minimum length for DNA (4) and for protein (2)
```

PYTHON Computer Program to Generate 68,374 DH Segments

```
minlen = 4
minp = 2
# Implement progressive base by base deletion from 5' or 3' or
both ends
alln = 0
for i in range(nseg):
    seq = seqs [i].seq
    lseq = len(seq)
    nt = ct = lseq
    for n in range(nt):
        for c in range(ct):
            nseq = seq [n:lseq-c]
            if (len(nseq) >= minlen):
                seqs [i].progdel.add(nseq)
    alln += len(seqs [i].progdel)
# Collect unique DNA sequences across all DH genes of origin
and ignore redundant ones
progdel = [ table( ) for i in range(alln) ]
n = 0
for i in range(nseg):
    for kk in seqs [i].progdel:
        unix = 1
        for j in range(n):
            if (kk == progdel [j].dna):
                unix = 0
                break
        if (unix == 1):
            progdel [n].name = seqs [i].name
            progdel [n].dna = kk
            n += 1
# Add none, 1 or 2 bp on one or both ends
# extras 20 + 20 * (21) = 20 + 420 = 440
# allocate memory for all variants
for i in range(n):
    progdel [i].dna_n = 440 * ['x']
    progdel [i].prot = 441 *3 * ['x']
    progdel [i].uprot = set( )
# add 1 or 2 bases at each end of input segment
tot = 0
for i in range(n):
# Step over each unique DNA sequence
    k = 0
# One base on 5' end combined with 1 or 2 bases added to 3' end
    for 15 in range(4):
        progdel [i].dna_n [k] = bases [15] + progdel [i].dna
        k += 1
        for 13 in range(4):
            progdel [i].dna_n [k] = bases [15] + progdel [i].dna +
bases [13]
            k += 1
            for 13 in range(4):
                for m3 in range(4):
                    progdel [i].dna_n [k] = bases [15] + progdel [i].dna +
bases [13] + bases [m3]
                    k += 1
# One or two bases added to 3' only in this part
        for 13 in range(4):
            progdel [i].dna_n [k] = progdel [i].dna + bases [13]
            k += 1
            for 13 in range(4):
                for m3 in range(4):
                    progdel [i].dna_n [k] = progdel [i].dna + bases [13] +
bases [m3]
                    k += 1
# Two bases on 5' end combined with 1 or 2 bp on 3' end
        for 15 in range(4):
            for m5 in range(4):
                progdel [i].dna_n [k] = bases [15] + bases [m5] +
progdel [i].dna
                k += 1
                for 13 in range(4):
                    progdel [i] .dna_n [k] = bases [15] + bases [m5] +
progdel [i] .dna + bases [13]
                    k +=1
                    for 13 in range(4):
                        for m3 in range(4):
                            progdel [i].dna_n [k] = bases [15] + bases [m5] +
```

PYTHON Computer Program to Generate 68,374 DH Segments

```
progdel [i].dna + bases [13] + bases [m3]
                            k += 1
# Now translate in all 3 forwared reading frames
# Save unique peptide sequences
    for fr in range(3):
        piece = progdel [i] .dna
        piece = piece [fr:]
        tpiece = translate_dna(piece)
        progdel [i].prot [fr] = tpiece
        progdel [i].uprot.add(tpiece)
        for k in range(440):
            piece = progdel [i].dna_n [k]
            piece = piece [fr:]
            tpiece = translate_dna(piece)
            progdel [i].uprot.add(tpiece)
            progdel [i].prot [3+440*fr +k] = tpiece
    tot += len(progdel [i].uprot)
# Collect unique sequences with no ASN at last or next to last
position, no unpaired or consecutive CYS, no stops
unset = set( )
segm = [genes( ) for i in range(tot) ]
lux = 0
nn = 0
for i in range(n):
    k = 0
    for kk in progdel [i].uprot:
# Filter out sequences with undesired features, including
length being too short (under "minp"defined above)
        if (len(kk) <minp): continue
        if (kk [len(kk) –1] == "N" or kk [len(kk) –2] ==
"N"): continue
        if (kk.count("Z") > 0 or kk.count("CC") >0 or
kk.count("C") % 2 >0): continue
        unset.add(kk)
        lux1 = len(unset)
        if (lux1 > lux):
            segm [nn].name = progdel [i].name + "_" +
str(nn)
            segm [nn].seq = kk
            nn += 1
            lux = lux1
        k += 1
# Print out unique peptide sequences that pass all the filters
for i in range(nn):
    out1.write("%s\t%s\n" % (segm [i].name, segm [i] .seq))
```

Example 7. Deriving Theoretical Segment Pools of TN1 and N2 Segments

The libraries of this example are designed to, in some instances, have a greater diversity in their TN1 and N2 segments in comparison to other libraries known in the art. The diversity of the TN1 and N2 segments was increased by using the matching method described in Example 4 to deconvolute the CDRH3 sequences in the HPS into their constituent segments (i.e., TN1, DH, N2, and H3-JH), followed by extraction of "novel" TN1 and N2 segments in the manner described below. For the purposes of the invention, "novel" TN1 and N2 segments are TN1 and N2 segments that do not appear in a theoretical segment pool that is matched to a reference set of CDRH3 sequences. Following is an example of the method used to extract novel TN1 and N2 segments from the HPS. This method can be generalized to extract novel TN1 and N2 segments from any reference set of CDRH3 sequences, using any theoretical segment pool containing TN1, DH, N2, and/or H3-JH segments.

Table 9 provides the matching results for the reference CDRH3 sequence ERTINWGWGVYAFDI (SEQ ID NO: 8760) (Test Cases 5.1-5.4) from the HPS, using Theoretical Segment Pool 1 ("TSP1"). The best matches to the reference CDRH3 are four CDRH3 sequences, each within three amino acids of the reference CDRH3 sequence. In each of these matches, the TN1, DH, N2 and H3-JH segments are of length 4, 3, 3 and 5 amino acids, respectively. Thus the reference CDRH3 can be deconvoluted into the following segments: ERTI-NWG-WGW-YAFDI (SEQ ID NO: 8761) (i.e. [TN1]-[DH]-[N2]-[H3-JH], respectively). The DH and H3-JH segments from the reference CDRH3, NWG and YAFDI (SEQ ID NO: 4540) respectively, are identically present in TSP1. However, the TN1 (ERTI) (SEQ ID NO: 8718) and N2 (WGW) segments from the reference CDRH3 are absent in TSP1 and match TSP1 segments with one or more amino acid mismatches. These "novel" TN1 and N2 segments are extracted from the reference CDRH3 and considered for inclusion prospective theoretical segment pools and/or synthetic libraries. Additional novel TN1 and N2 segments were accumulated by applying this analysis to all members of the HPS. In order to robustly identify TN1 and N2 sequences, the extraction was performed only for those CDRH3 sequences in which the DH and H3-JH segments in the reference CDRH3 and TSP1 cumulatively return no more than 3 amino acid mismatches, implying that the DH and H3-JH segments of the reference CDRH3 had been reliably assigned.

Example 8. Calculation of Segment Usage Weights

Segment usage weights were calculated for their utility in determining which segments from the theoretical segment pools (e.g., TSP1 and TSP1 plus novel TN1 and N2 segments identified as described in Example 7) should be included in a synthetic library. Segment usage weights were obtained by utilization of the matching method described above and Equation 2:

$$w(i) = \frac{1}{S_m} \sum_{j=1}^{S_m} \frac{1}{g(j)} \sum_{k=1}^{g(j)} f_i(k)$$

Equation 2 where,
- $w(i)$: Weight for segment i. $0 \leq w(i) \leq 1$.
- $S_m$: Number of sequences (out of total S in the reference CDRH3 set) which contain one or more best matches with no more than m amino acid mismatches in the specified region of the reference CDRH3 sequence. Here, the mismatches are computed over the Kabat-CDRH3 region, but other fragments of the CDRH3 sequences may also be considered. A constant value of m=3 was used here, but other values may be used, or the value may depend on the length of the reference CDRH3 sequence.
- $g(j)$: Total number of degenerate segment combinations producing the best match to the reference CDRH3 sequence j.
- $f_i(k)$: Fractional amino acid identity of TN1, DH, N2 or H3-JH segment in degenerate match k, relative to the corresponding sequence fragment in the reference CDRH3 sequence j. The fractional amino acid identity equals zero if the segment does not appear in match k. Other definitions off such as amino acid similarity (e.g., based on physicochemical properties of the amino acids such as hydrophobicity), instead of identity, may be also used.

The procedure for calculating segment usage weights will be further exemplified below. In each of these examples, the best match combinations from TSP1 are provided for a single CDRH3 sequence ($S_m$=1) and the degeneracy (k) and fractional mismatch (f) dependent weight calculations are explained.

Example 8.1. Segment Usage Weights for Test Case 1 in Table 9

Refer to Test Case 1 in Table 9. The CDRH3 sequence RTAHHFDY (SEQ ID NO: 3660) is identically located in TSP1 (f=1, subscripts dropped for simplicity) via a unique segment combination (g=1). Table 18 provides the usage weights for the segments corresponding to the best match from TSP1 for the CDRH3 of Test Case 1.

Example 8.2. Segment Usage Weights for Test Cases 2.1 and 2.2 in Table 9

Refer to Test Cases 2.1 and 2.2 in Table 9. The CDRH3 sequence VGIVGAASY (SEQ ID NO: 3661) may be identically located in TSP1 (f=1) via two distinct segment combinations (g=2). Table 19 provides the usage weights for the segments corresponding to the best match from TSP1 for the CDRH3 of Test Cases 2.1 and 2.2.

Example 8.3. Segment Usage Weights for Test Case 3.1 in Table 9

Refer to Test Case 3.1 in Table 9. The CDRH3 sequence DRYSGHDLGY (SEQ ID NO: 3662) may be identically located in TSP1 via a unique segment combination (g=1) with a single amino acid difference. As provided below, the TN1, N2 and H3-JH segments match the corresponding reference sequence fragments identically, while four of the five DH amino acids match identically.

```
Sequence from the HPS:
                                      (SEQ ID NO: 3662)
DR-YSGHD-LG-Y Nearest Neighbor in TSP1:
                                      (SEQ ID NO: 8719)
DR-YSGYD-LG-Y
```

Thus, here
f=4/5 for the DH segment; and
=1 for the TN1, N2, and H3-JH segments (Table 20).

Example 8.4. Matching of Test Cases 4.1 and 4.2 in Table 9

Refer to test cases 4.1 and 4.2 in Table 9. The CDRH3 sequence GIAAADSNWLDP (SEQ ID NO: 3663) may be located in TSP1 via two distinct segment combinations (g=2), each with a single amino acid difference. As provided below, the TN1, DH and N2 segments match the corresponding reference sequence fragments identically, while five of the six H3-JH amino acids match identically.

```
Sequence from HPS:
                                      (SEQ ID NO: 3663)
(-)-GIAAA-D-SNWLDP Nearest Neighbor in TSP1:
                                      (SEQ ID NO: 8720)
(-)-GIAAA-D-SNWFDP
```

-continued

```
Sequence from HPS:
                                        (SEQ ID NO: 3663)
G-IAAA-D-SNWLDP Nearest Neighbor in TSP1:
                                        (SEQ ID NO: 8720)
G-IAAA-D-SNWFDP
Here, (-) represents the "empty" TN1 segment.
```

Applying Equation 2 results in the segment usage weights provided in Table 21.

Example 8.5. Calculating the Segment Usage Weights for Test Cases 1 to 4.2 of Table 9

Extending the individual calculations described above to simultaneously include all of Test Cases 1 to 4.2 of Table 9 results in the segment usage weights of Table 22.

Example 8.6. Calculating the Segment Usage Weights for Test Cases 5.1 to 5.4 of Table 9

Refer to the CDRH3 sequence ERTINWGWGVYAFDI (SEQ ID NO: 8760) and the novel TN1 and N2 segments extracted from the CDRH3 sequence, in Example 7. In this case, the novel TN1 and N2 segments (ERTI (SEQ ID NO: 8718) and WGV respectively), and the DH and H3-JH segments from TSP1 (NWG and YAFDI (SEQ ID NO: 4540) respectively) are each assigned usage weights of unity.

Figure 5:
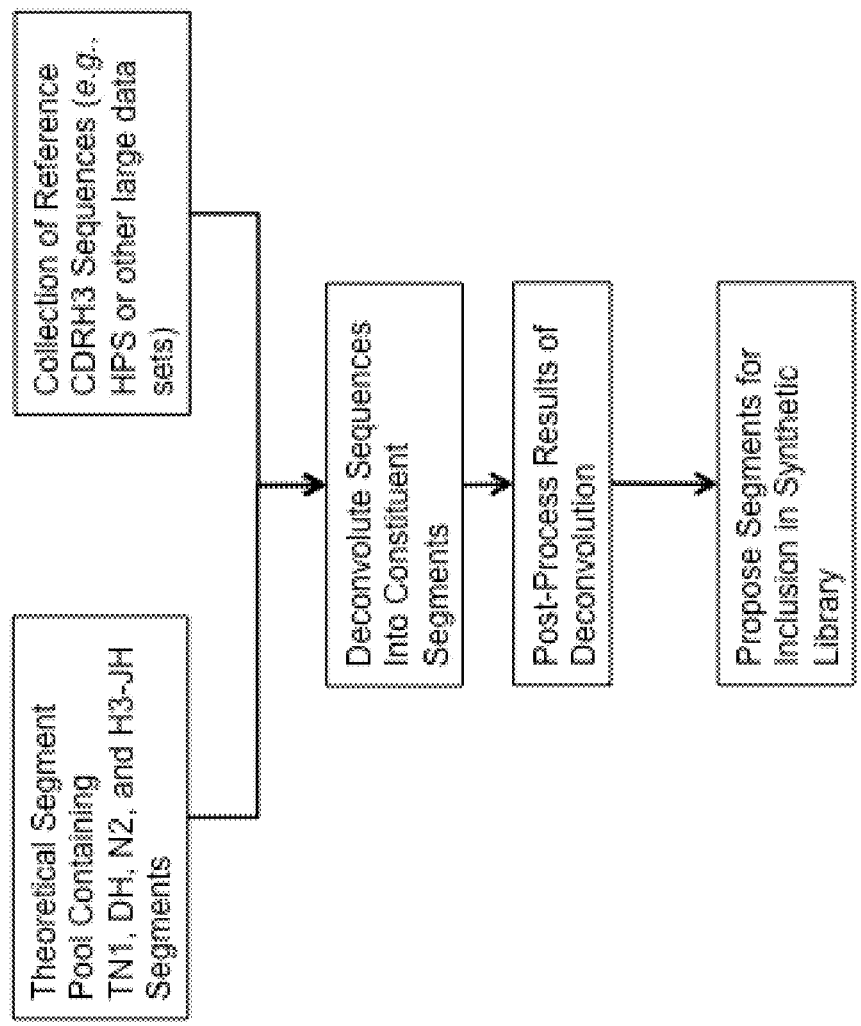
FIG. 5 shows the general schematic of an approach used to select segments from a theoretical segment pool for inclusion in a theoretical and/or synthetic library.

Example 9. Selection of TN1, DH, N2 and JH Segments for Inclusion in Synthetic Libraries FIG. 5 provides the general method used for the design of synthetic CDRH3 libraries. The method uses as input: (1) a theoretical segment pool containing TN1, DH, N2, and H3-JH segments (e.g., TSP plus novel TN1 and N2 segments); and (2) a collection of reference CDRH3 sequences (e.g., the HPS). From these inputs, a particular subset of segments from the theoretical segment pool is selected for inclusion in a physical CDRH3 library.

First, the best matches to the CDRH3s of the HPS were obtained, from within the TSP1 set, with or without the novel TN1 and N2 segments, using the matching method described above. This data was then used to compute the segment usage weights via Equation 2. Segments were prioritized for inclusion in the physical library based on their relative frequency of occurrence in the CDRH3 sequences of the HPS (as indicated by the segment usage weights), as well as other factors (more fully described below), such as hydrophobicity, alpha-helical propensity, and expressibility in yeast.

Example 9.1. Exemplary Library Design (ELD-1)

ELD-1 uses the HPS and the segments from TSP1 1 ($9.5 \times 10^9$ members) as inputs and produces an output of 100 TN1, 200 DH, 141 N2 and 100 H3-JH segments, each from TSP1, ranked in order by their usage weights in the HPS, to produce a library with theoretical complexity of $2.82 \times 10^8$. The segments corresponding to ELD-1 are provided in Table 23. Note that here the combination of all of the segments (i.e., TN1, DH, N2, and H3-JH), and the individual sets of segments (i.e., TN1 only, DH only, N2 only, and H3-JH only) each constitute theoretical segment pools.

Example 9.2. Exemplary Library Design 2 (ELD-2)

The inputs for this design are the HPS and the segments from TSP1 plus the novel TN1 and N2 segments extracted from the HPS (Example 7). The outputs are (1) 200 DH and 100 H3-JH segments, each from TSP1; and (2) 100 TN1 and 200 N2 segments including TN1 and N2 segments originally in TSP1 and those extracted from the sequences in the HPS. Applying the method described in Example 7 to extract novel TN1 and N2 segments (i.e., those not included in TSP1) resulted in the identification of 1,710 novel TN1 segments and 1,024 novel N2 segments. The segments corresponding to ELD-2 are provided in Table 24. Note that here the combination of all of the segments (i.e., TN1, DH, N2, and H3-JH), and the individual sets of segments (i.e., TN1 only, DH only, N2 only, and H3-JH only) each constitute theoretical segment pools. As in ELD-1, all segments in ELD-2 were selected for inclusion based solely on their usage weights in the HPS.

Example 9.3. Exemplary Library Design 3 (ELD-3)

The inputs for this design are identical to those for ELD-2. As in ELD-2, the outputs are (1) a set of 200 DH and 100 H3-JH segments, each from TSP1; and (2) a set of 100 TN1 and 200 N2 segments, including TN1 and N2 segments originally in TSP1 and those extracted from the sequences in the HPS (Example 7). However, the approach used for the selection of the segments for ELD-3 differs in two respects. First, selected physicochemical properties of the segments (hydrophobicity, isoelectric point, and alpha-helix propensity) were used, in addition to the segment usage weights, to prioritize segments for inclusion in the physical library. Hydrophobicity was used to de-prioritize hydrophobic DH segments that are empirically over-represented in poorly expressed antibodies isolated from yeast-based libraries. Isoelectric point and propensity for alpha-helix formation were utilized to identify segments located in regions of physicochemical property space that were relatively unexplored in CDRH3 libraries known in the art (e.g., U.S. Publication Nos. 2009/0181855 and 2010/0056386, and WO/2009/036379). Second, the segment usage weights were calculated via a bootstrap analysis of the HPS dataset. These methods are more fully described below. The segments corresponding to ELD-3 are provided in Table 25. Note that here the combination of all of the segments (i.e., TN1, DH, N2, and H3-JH), and the individual sets of segments (i.e., TN1 only, DH only, N2 only, and H3-JH only) each constitute theoretical segment pools.

Example 9.3.1. Generation of Segment Usage Weights Via Bootstrap Analysis

Bootstrap analysis (Efron & Tibshirani, *An Introduction to the Bootstrap*, 1994 Chapman Hill, N.Y.) is a widely used statistical procedure for estimating the variability of a statistic of a given sample. This estimate is based on the value of the statistic calculated for several sub-samples, equal in size to the original sample and derived from it via sampling with replacement. Members of the original sample are chosen at random to form the sub-samples, and are typically included multiple times in each sub-sample (hence, "sampling with replacement").

Here, the original sample is the HPS dataset with n=3,571 members and the statistic is the segment usage weight. One-thousand sub-samples, each with 3,571 members, were generated by randomly choosing sequences from the HPS dataset (no more than 10 repeats of a given sequence were allowed in each sub-sample). The matching method described above was then applied to each sub-sample, and the final segment usage weights were calculated as the average of the values obtained for the individual sub-samples. Average values derived via this bootstrap procedure are more robust than values calculated from the parent HPS dataset alone. Unless indicated otherwise, these average values of the 1,000 sub-samples were used in the selection of segments for ELD-3.

Example 9.3.2. Amino Acid Property Indices

The AAindex database, available online at world wide web at genome.jp/aaindex/, provides more than 500 numerical indices representing various physicochemical and biochemical properties of amino acids and pairs of amino acids. These properties include hydrophobicity, electrostatic behavior, secondary structure propensities and other characteristics, with several indices often available for a given property. The following three indices were chosen by starting with the well-understood Kyte-Doolittle hydropathy index (KYJT820101) and adding the indices most numerically de-correlated from it and each other. They thus potentially describe non-overlapping regions of amino acid property space and were used for analysis and selection of the DH and H3-JH segments for ELD-3:
1. KYTJ820101 (hydropathy index)
2. LEVM780101 (normalized frequency of alpha helix)
3. ZIMJ680104 (isoelectric point)

Figure 6:
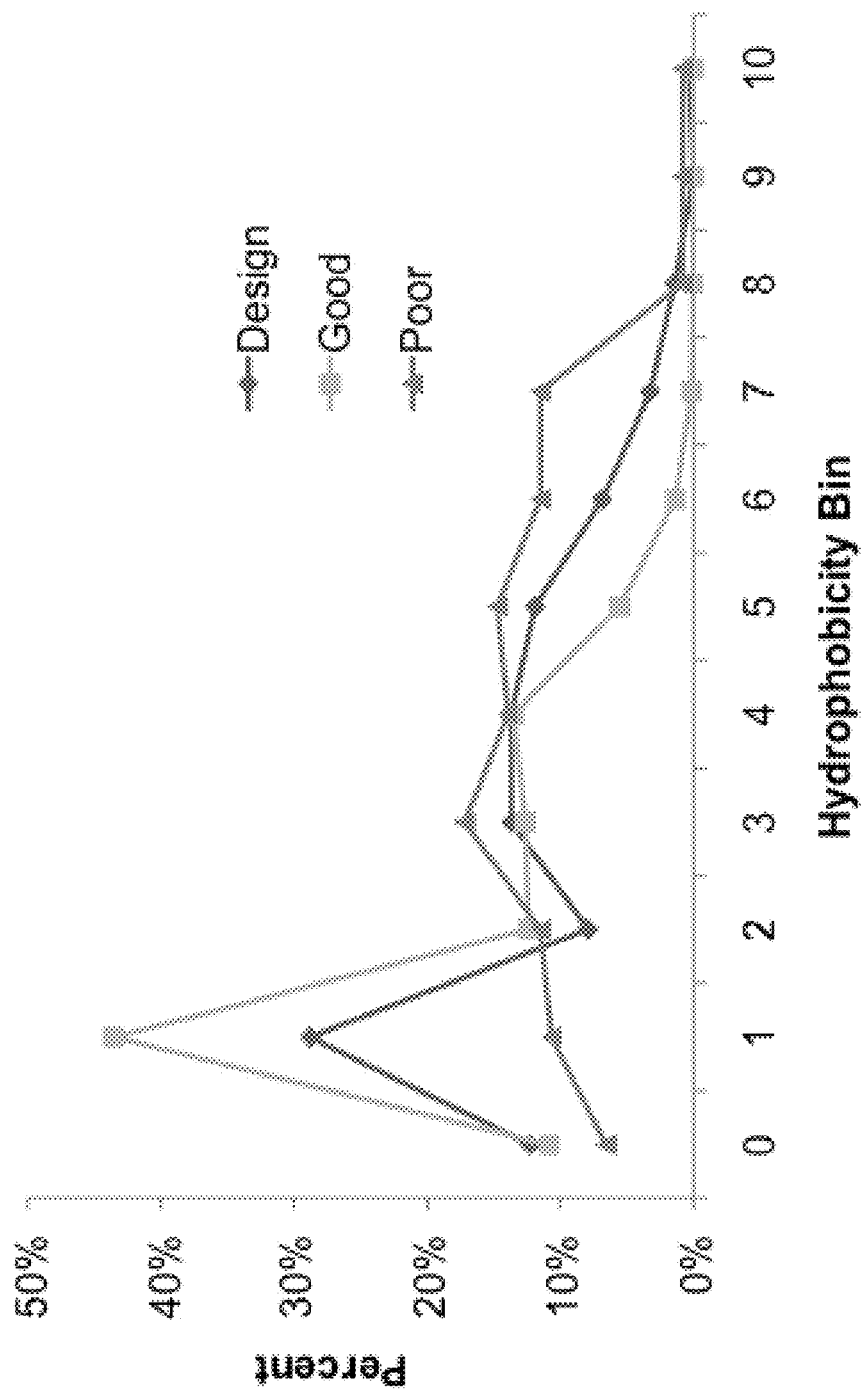
FIG. 6 shows the frequency of "Good" and "Poor" expressing CDRH3 sequences isolated from yeast-based libraries described in US 2009/0181855, and their comparison to the sequences contained in the library design described therein ("Design"), as a function of the DH segment hydrophobicity (increasing to the right).

Example 9.3.3. Hydrophobic DH Segments are Over-Represented in Poorly Expressed Antibodies Isolated from Yeast-Based Libraries Based on protein expression levels from approximately 1200 antibodies expressed in S. cerevisiae, antibodies were classified as either "Good" or "Poor" expressors. The CDRH3 sequence of each antibody in each category was examined to identify sequence features that correlated with the expression level. One such sequence feature is the hydrophobicity of the DH segments calculated using the KYTJ820101 index. FIG. 6 provides the frequency of "Good" and "Poor" expressors as a function of the DH segment hydrophobicity (increasing to the right). The distribution expected from the synthetic library used to isolate these antibodies is also provided as a reference ("Design"). DH segments with the highest hydrophobicity values (far right of the plot) are over-represented (relative to the expectation based on the design) among "Poor" expressors and under-represented among "Good" expressors. Similarly, hydrophilic DH segments (far left) are over-represented among "Good" expressors and under-represented among "Poor" expressors. From this data, it was inferred that the overall expressibility of the antibodies of the library may be improved by synthesizing CDRH3 sequences with fewer hydrophobic DH segments.

Example 9.3.4. Selection of the 200 DH Segments for Inclusion in ELD-3

A set of 71 DH segments from TSP1 were designated as "core" DH segments for automatic inclusion in ELD-3. These segments had the following desirable properties:
1. Fifty-three of seventy-one were present within the top 7% of DH segments rank-ordered by segment usage weights from the bootstrap analysis.
2. Eighteen of seventy-one were present within the top 7% of DH segments rank-ordered by usage weights derived from antibodies isolated from libraries expressed in S. cerevisiae.

The remaining 1,040 segments were designated as "non-core." To complete the set of 200 segments in ELD-3, 129 segments were chosen from the "non-core" pool of segments in the following manner:
1. Sixty-five segments were eliminated because they contain either (a) an Asn residue at the last or next-to-last position with the potential to form N-linked glycosylation motifs via combination with N2 amino acids or (b) the amino acid sequence NG, implicated in de-amidation.
2. Segments with higher than median values for the KYTJ820101 hydropathy index (median=2.9 for 1K DH) were eliminated from further consideration. In view of the known importance of Tyr for antigen recognition (Fellouse et al., PNAS, 2004, 101: 12467; and Hofstadter et al., J. Mol. Biol., 1999, 285: 805, each incorporated by reference in its entirety), segments containing at least one Tyr residue were retained unless located in the highest hydrophobicity quartile (KYTJ820101 value higher than 9.4). This eliminated 443 segments.
3. The final set of 129 segments was obtained by using an objective function that aimed to maximize the Euclidean distance, between the "core" and the remaining 443 "non-core" segments, in a multi-dimensional space defined by the following variables: (1) amino acid mismatches to nearest neighbor; and (2) values of the three physicochemical property indices.

Example 9.3.5. Selection of the 100 H3-JH Segments for Inclusion in ELD-3

One-hundred H3-JH segments were chosen for inclusion in ELD-3 in the following manner.
1. Twenty-eight H3-JH segments were selected after being experimentally validated in other libraries containing only these H3-JH segments (see U.S. Publication Nos. 2009/0181855 and 2010/0056386, and WO/2009/036379).
2. Fifty-seven segments were selected based on their presence within the top 25% of H3-JH segments rank-ordered by usage weights from the bootstrap analysis described above. These 57 H3-JH segments, plus the 28 H3-JH segments of (1) (i.e., 85 segments total) were designated as the "core" H3-JH segments, which, like the core DH segments, were automatically included in ELD-3.
4. Fifteen additional segments were chosen by using an objective function that aimed to maximize the Euclidian distance, between the "core" and the remaining 200 "non-core" segments, in a multi-dimensional space defined by the following variables: (1) amino acid mismatches to nearest neighbor; and (2) values of the three physicochemical property indices.

Example 9.3.6. Selection of 100 TN1 and 200 N2 Segments for Inclusion in ELD-3

TN1 and N2 segments were extracted from the sequences in each sub-sample of the bootstrap procedure, and the 100 TN1 and 200 N2 segments with the highest average segment usage weights were chosen for inclusion into the library, after elimination of sequences with undesirable motifs, namely Cys and Asn residues.

Example 9.3.7. Selection of Nucleotide Sequences to Encode the Segments Chosen for Inclusion in ELD-3

Each of the polypeptide segments chosen for inclusion in the library must be back translated (polypeptide to DNA) into a corresponding oligonucleotide sequence. While a large number of oligonucleotides could possibly encode each polypeptide segment, due to the degeneracy of the genetic code, certain constraints were imposed to select oligonucleotides that were more desirable. First, since ELD-3 was expressed in yeast (S. cerevisiae), codons that are rarely used in yeast were avoided. For example, of the six possible codons for Arg, three: CGA, CGC and CGG are used to encode yeast proteins at rates of under 10% (see, for example, Nakamura et al., Nucleic Acids Res., 2000, 28:292), and therefore those three codons were avoided to the extent possible. Second, since many antibodies are produced in Chinese Hamster Ovary (CHO) cells (after discovery e.g., in yeast), the CCG codon (encoding Pro) was also avoided, since it is rarely used by hamsters (Nakamura et al.)

A number of restriction enzymes are employed during the actual construction of the CDRH3 oligonucleotide library (see Example 10 of U.S. Pub. No. 2009/0181855). It is thus desirable to avoid the occurrence of recognition motifs for these restriction enzymes within the CDRH3 polynucleotide sequences. Codons are selected at the individual segment level to avoid introducing recognition motifs for restriction enzymes that may be used downstream. Since such motifs may also be generated by combinatorial assembly of the segments, the segment combinations are also checked and, whenever possible, codons are changed to eliminate the occurrence of such motifs. Specifically, three restriction enzymes were used during the construction of the currently exemplified CDRH3 library: BsrDI, BbsI, and AvrII. The first two are type II enzymes with non-palindromic recognition sites. The reverse strand of the oligonucleotides encoding the segments was checked explicitly for recognition sites for these two enzymes. In particular, the reverse strands were checked for the motifs GCAATG and CATTGC (for BsrDI) and GAAGAC and GTCTTC (for BbsI). The recognition motif for AvrII is palindromic so the oligonucleotides were only checked for the sequence CCTAGG. However, AvrII is used only to treat TN1 segments, and thus it is not necessary to evaluate its presence in the other segments or their combinations.

An additional constraint that was imposed to improve engineering of the polypeptide to polynucleotide conversion was avoidance of consecutive runs of 6 or more of the same type of base, as this is believed to increase errors during solid phase oligonucleotide synthesis. Therefore, DNA sequences for the segments of ELD-3 were chosen to avoid such motifs. The DNA sequences for the ELD-3 segments are included, with the respective polypeptide sequences, in Table 25. One of ordinary skill in the art will readily recognize that these methods can also be applied to any other library, any restriction sites, any number of nucleotide repeats, and/or to avoid the occurrence of any codons considered undesirable in any organism.

Example 10. Matching of ELD-3 to Human CDRH3 Datasets and Clinically Relevant Antibodies Among the objectives of the invention is to mimic the V-D-J recombination processes underlying the creation of the human CDRH3 repertoire in vivo, thereby increasing the diversity of the CDRH3 library in comparison to other libraries known in the art, while maintaining the human character of CDRH3. One measure of success is the extent to which collections of human reference CDRH3 sequences are represented identically, or via close matches (e.g., less than about 5, 4, 3, or 2 amino acid differences) in any library of the invention. We evaluated this metric using two human CDRH3 sequence reference datasets, both non-overlapping with each other and the HPS: (1) a collection of 666 human CDRH3 sequences (Lee et al., Immunogenetics, 2006, 57: 917; "Lee-666"); and (2) a collection of 3,000 human CDRH3 sequences randomly chosen from the over 200,000 sequences disclosed in Boyd et al., Science Translational Medicine, 2009, 1: 1-8 ("Boyd-3000"). The results of the random sample of the 3,000 human CDRH3 sequences from Boyd et al. was representative of the results of the same analysis as applied to all members of the Boyd et al. set (>200,000 CDRH3 sequences).

Figure 7:
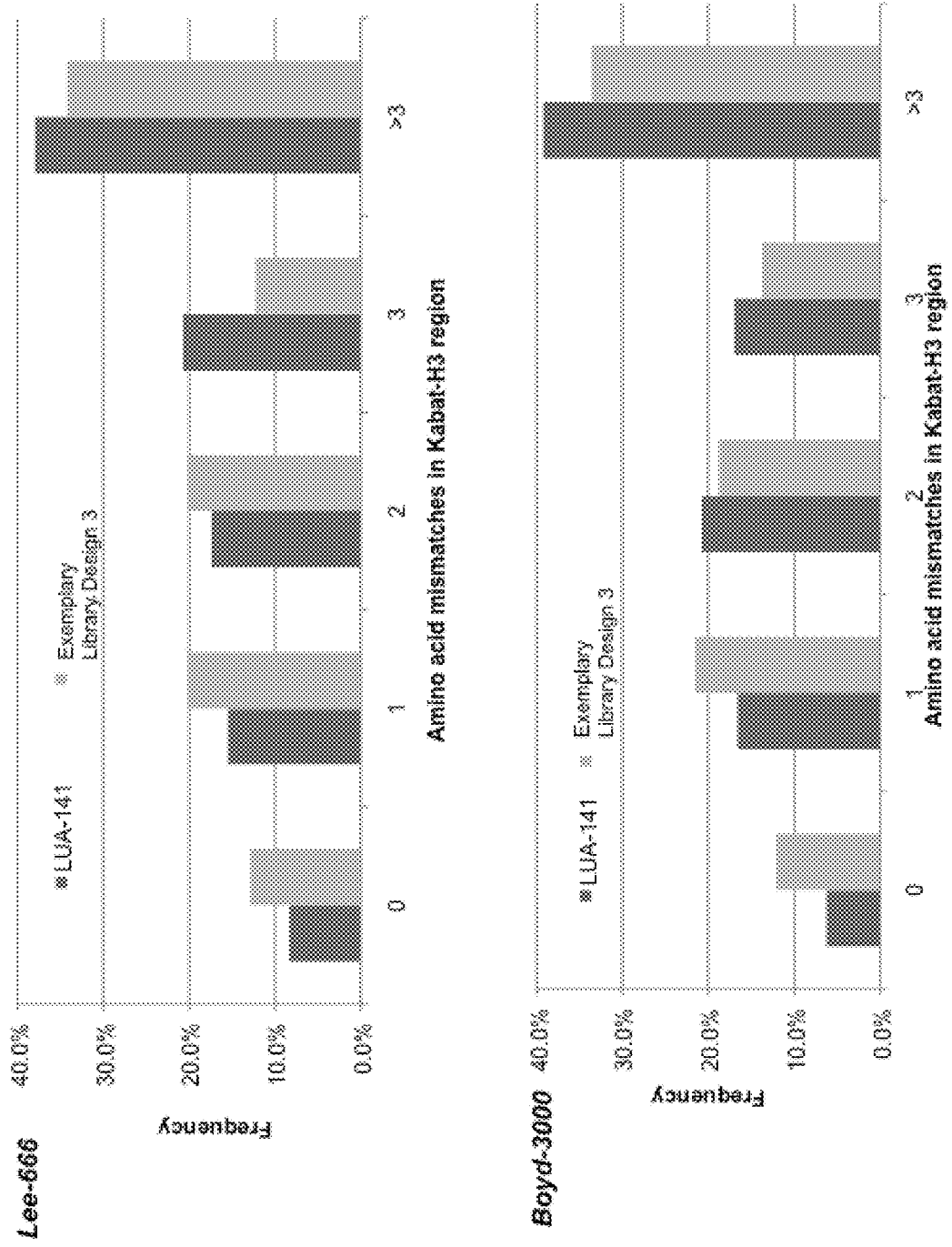
FIG. 7 shows the percentage of CDRH3 sequences in the LUA-141 library and Exemplary Library Design 3 (ELD-3) that match CDRH3 sequences from Lee-666 and Boyd-3000 with zero, one, two, three, or more than three amino acid mismatches.

FIG. 7 provides the percentage of CDRH3 sequences in two synthetic libraries, "LUA-141" and ELD-3, that match a sequence from the Lee-666 or Boyd-3000 sets with zero, one, two, three, or more than three amino acid mismatches. Here, "LUA-141" represents a library containing 212 TN1, 278 DH, 141 N2, and 28 H3-JH (see U.S. Publication No. 2009/0181855 for details). In particular, it is notable that ELD-3 exhibits a higher percentage of sequences (12.9% and 12.1% for the Lee-666 and Boyd-3000 sets, respectively) that identically match a reference CDRH3 sequence than LUA-141 (8.4% and 6.3% for the Lee-666 and Boyd-3000 sets, respectively). It is also notable that ELD-3 exhibits a higher cumulative percentage of human CDRH3 sequences found with no more than two amino acid mismatches (54.1% and 52.5% for the Lee-666 and Boyd-3000 sets, respectively) relative to LUA-141 (41.2% and 43.7% for the Lee-666 and Boyd-3000 sets, respectively).

Another metric by which antibody libraries can be evaluated is their ability to match "clinically relevant" reference CDRH3 sequences. FIG. 8 demonstrates that ELD-3 returns better matches to clinically relevant CDRH3 sequences than the LUA-141 library. Specifically, ELD-3 matches 34 of 55 (62%) clinically validated antibodies within one amino acid, while the LUA-141 library only matches 20 of 55 (37%).

Example 11. Comparison of ELD-3 to LUA-141

Figure 9:
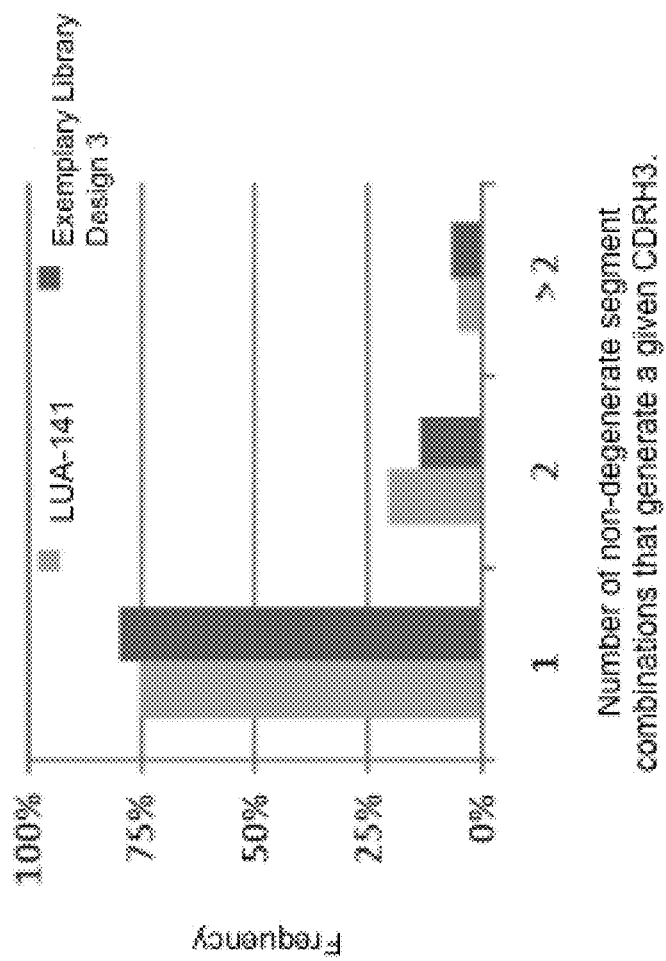
FIG. 9 shows that the combinatorial efficiency of Exemplary Library Design 3 (ELD-3) is greater than that of the LUA-141 library. Specifically, the ELD-3 segments are more likely to yield a unique CDRH3 than the LUA-141 library segments.

ELD-3 has 73 TN1, 92 DH, 119 N2, and 28 H3-JH in common with LUA-141. Thus, 94.5% of the sequences in ELD-3 ($4.0 \times 10^8$ members) are different from the LUA-141 library ($2.3 \times 10^8$ members). FIG. 9 demonstrates that the combinatorial efficiency of the segments in ELD-3 is greater than that of the segments in LUA-141. Specifically, the ELD-3 segments are more likely to yield a unique CDRH3 than the LUA-141 library segments. This is advantageous, because it allows one to synthesize libraries with increased CDRH3 diversity using fewer segments.

Figure 10:
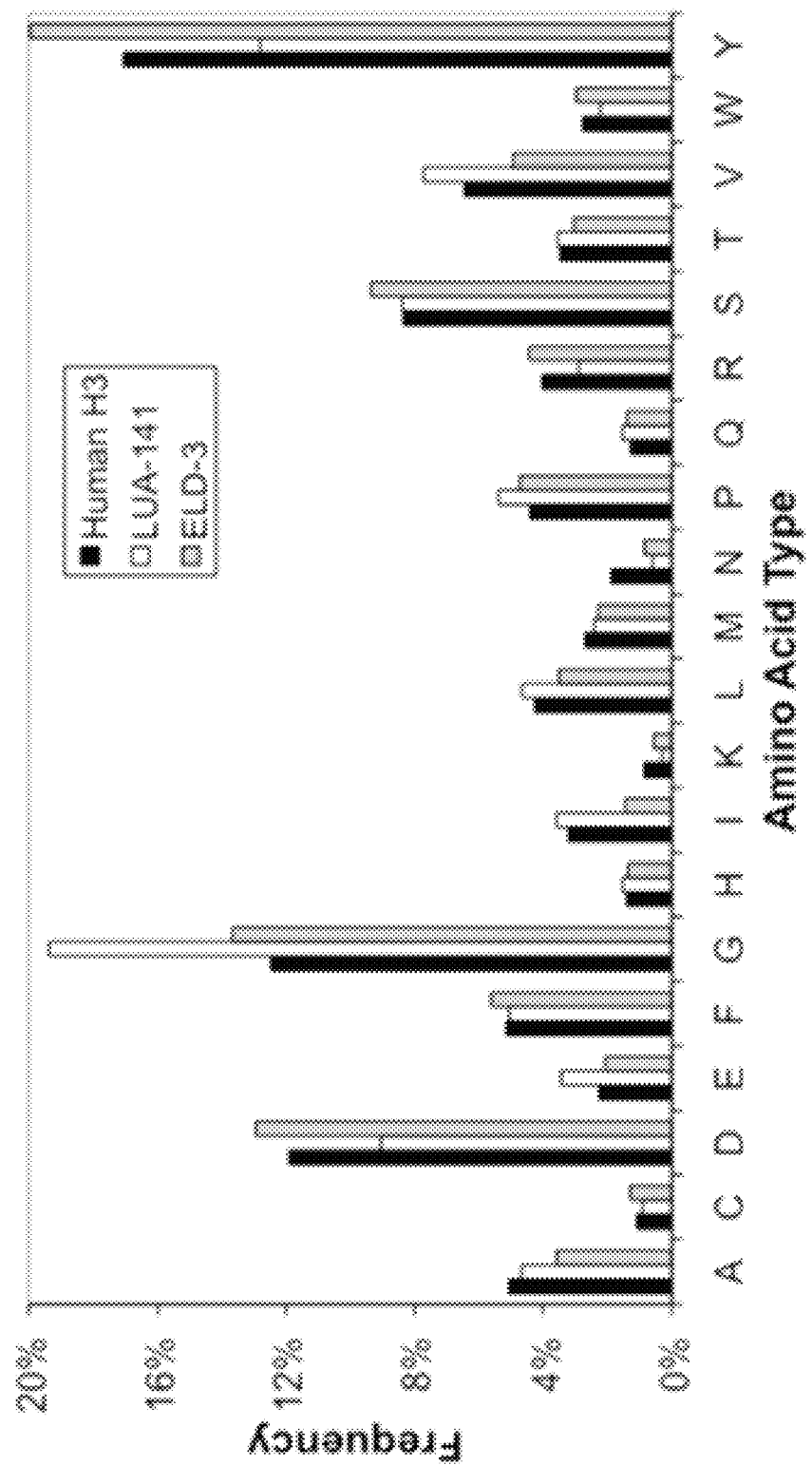
FIG. 10 shows the amino acid compositions of the Kabat-CDRH3s of LUA-141, Exemplary Library Design 3 (ELD-3), and Human CDRH3 sequences from the HPS (Human H3).

FIG. 10 provides the amino acid compositions of the Kabat-CDRH3s of LUA-141, ELD-3, and Human CDRH3 sequences from the HPS.

Figure 11:
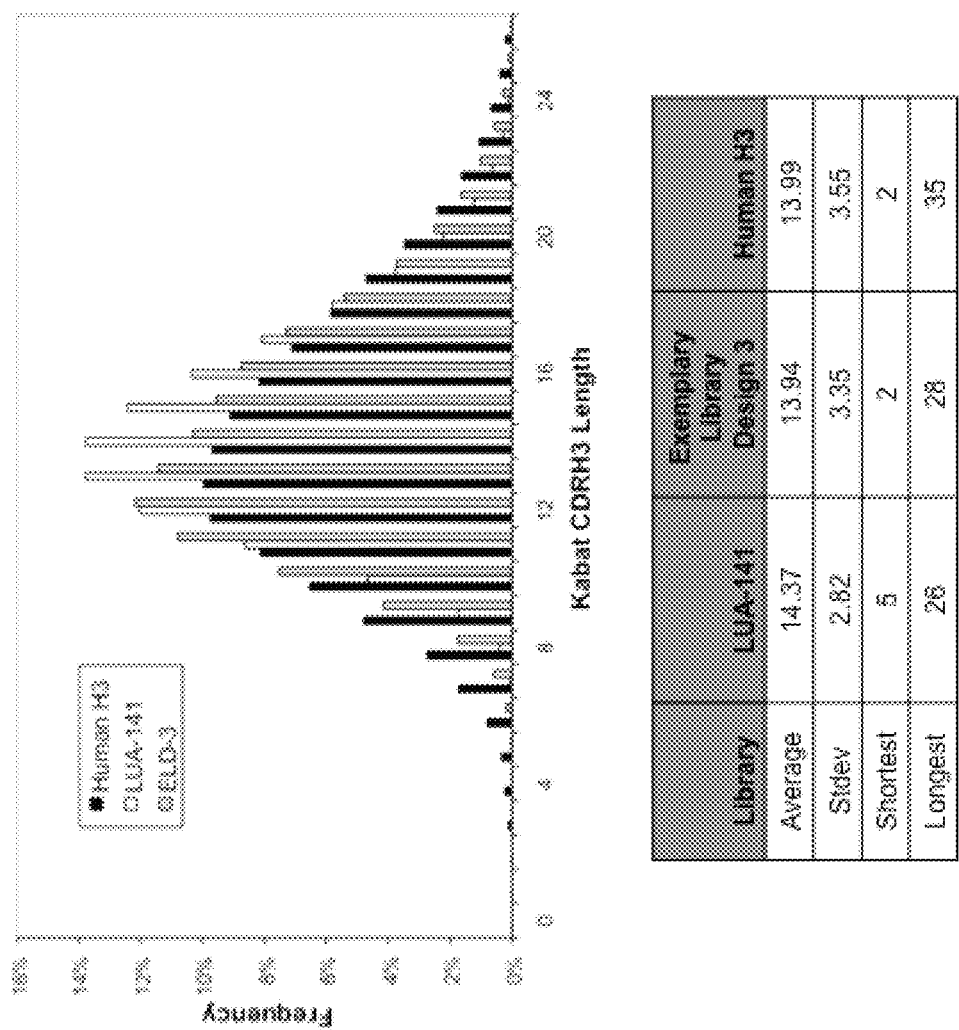
FIG. 11 shows the Kabat-CDRH3 length distribution of LUA-141, Exemplary Library Design 3 (ELD-3), and Human CDRH3 sequences from the HPS (Human H3).

FIG. 11 provides the Kabat-CDRH3 length distribution of LUA-141, ELD-3, and Human CDRH3 sequences from the HPS.

CDRH3 Libraries Synthesized with Degenerate Oligonucleotides

Example 12. Further Increasing CDRH3 Diversity by Utilizing Degenerate Oligonucleotides The methods described in this example extend the methods taught above, to produce CDRH3 libraries with more members than those of the libraries described above. In particular, one or two degenerate codons were introduced into the DH and or N2 polynucleotide segments, and (generally) no degenerate codon or one degenerate codon were introduced into the H3-JH segments. Segments with different numbers of degenerate codons are also contemplated; for example DH segments with 0, 1, 2, 3, 4, 5, 6, 7, 8, or more degenerate codons, and H3-JH segments with 0, 1, 2, 3, 4, 5, or more degenerate codons. This results in CDRH3 libraries containing greater than about $10^{11}$ (about $2\times10^{11}$) distinct CDRH3 amino acid sequences that closely reflect properties, such as length and composition among others, of a reference set of human CDRH3 sequences. As described below, the degenerate positions in the DH segments are usually, but not always, the very N- and/or C-terminal positions, or 5' and 3' end codons (i.e., not necessarily only the first or last base), respectively, when considering the corresponding oligonucleotide sequences. Degenerate codons were similarly used to synthesize N2 segments. Two hundred of the TN1 segments were as described in ELD-3, although libraries with degenerate TN1 segments, or with alternative choices of TN1 segment sequences, fall within the scope of the invention. An additional one hundred TN1 segments complete the set of 300 TN1 segments for this library. The amino acid and nucleotide sequences are listed in Table 26. It is also possible to use mixtures of trinucleotides instead of, or in addition to, degenerate oligonucleotides in order to allow amino acid type variation at one or more selected positions within "base" or "seed" segment sequences (defined below).

Example 13. Selection of DH Segments for Synthesis by Degenerate Oligonucleotides The segment usage weights were calculated for the 68K DH Theoretical Segment Pool by comparison to the sequences contained in Boyd et al. The DH segments with a length of three or more amino acids were ranked according to their segment usage weights (as described above), and the top 201 were designated as "seed" sequences. These seed sequences were then varied by selecting certain positions to incorporate degenerate codons. The positions selected for variance, the amino acids types to which they were varied, were determined by comparing the seed sequences to a reference set of 9,171 DH segments that were a subset of the 68K DH Theoretical Segment Pool. These 9,171 DH segments were selected because their segment usage weight in Boyd et al. was significant, meaning that the cumulative segment usage weight (Example 8) is at least 1.0.

Each of the 201 seed sequences was compared to each of the sequences in the reference set of 9,171 DH segments, and those of identical length and differing at a single position were further considered to inform possible variants of the seed. In this manner, the most variable position for each seed was identified and a set of candidate amino acid types was also identified for each position. Finally, a set of degenerate codons was considered, to identify the codon that most faithfully represented the set of candidate amino acid types for each particular position. Degenerate codons encoding stop codons, Cys residues, N-linked glycosylation motifs (i.e., NXS or NXT, where X is any amino acid type), or deamidation motifs (NG) were eliminated from consideration. This process generated 149 unique degenerate oligonucleotide sequences, which collectively encode 3,566 unique polypeptide sequences. Alternative designs generated according to the same principles were also considered, and those having a larger diversity (in terms of the number of unique polypeptide sequences) and smaller RMAX values (see below) were given preference for inclusion in the libraries of the invention. However, it is also conceivable that different criteria could be used to select DH segments from the 68K DH Theoretical Segment Pool, and that libraries including DH segments selected by these different criteria would also fall within the scope of the invention.

Because not all degenerate oligonucleotides encode an identical number of polypeptides, the latter do not occur with uniformly identical weights over the entirety of a given theoretical segment pool (i.e., TN1, DH, N2 and H3-JH) contained within a CDRH3 library of the invention. For example, an individual amino acid sequence X encoded by an oligonucleotide of total degeneracy 4 will have a "weight" of ¼, while another individual amino acid sequence, Y, encoded by an oligonucleotide of degeneracy 6 will have a weight of ⅙. Moreover, certain amino acid sequences could be encoded by more than one degenerate oligonucleotide, so their weights will be the sum of the individual contributions by each oligonucleotide. Within a given theoretical segment pool, the ratio of the weight of the most heavily weighted polypeptide to that of the least heavily weighted one, RMAX, is an important design criterion that one would ideally like to minimize. The RMAX value may be defined by length, or overall for all of the segments of any given type (i.e., all the DH segments, or all the H3-JH segments, and so on for the TN1, and/or the N2 segments). Table 27 lists the degenerate oligonucleotide sequences, while Table 28 lists the unique polypeptide sequences resulting from these oligonucleotides. These two tables include the DH dimer segments the design of which is detailed below.

Example 13.1. Selection of DH Dimer Segments

A different method was employed to design a set of degenerate oligonucleotides encoding DH dimer sequences. The method aimed to include all of the 45 dimer sequences in ELD-3 plus as many of the other 400 theoretically possible dimer sequences (i.e., 20 residues possible in each of 2 positions=20*20), minus segments containing Asn (N) residues and excessively hydrophobic dimers (i.e., any dimer combination comprising only F, I, L, M, and/or V residues). This design process ultimately yielded 35 degenerate oligonucleotide sequences encoding 213 unique peptide dimer sequences. As with the selection processes used for all of the other segments of the invention, one or ordinary skill in the art will readily recognize that other criteria could be used to select the DH dimer segments, and that libraries including these segments also fall within the scope of the invention.

Combining the DH dimer segments with the longer DH segments of Example 13, yielded the final set of DH segments of the currently exemplified library, encoded by a total of 184 oligonucleotides (35 encoding dimers and 149 encoding segments having three or more amino acids) versus the 200 oligonucleotides of ELD-3. The 184 oligonucleotides encode a total of 3,779 unique polypeptide sequences: 213 dimers and 3,566 longer segments of three amino acids or greater.

Example 14. Generation of Expanded N2 Diversity

As described above, ELD-3 contains 200 N2 segments. In the currently exemplified library, the empty N2 segment (i.e., no N2, so that the DH segments are joined directly to the H3-JH segments) and monomer N2 segments were the same as in ELD-3. However, degenerate oligonucleotides were used to generate sets of two-, three-, and four-mers that not only recapitulated all of the corresponding sequences in ELD-3 but also resulted in additional diversity. As with the DH segments, these degenerate oligonucleotides were designed to eliminate Asn (in unsuitable positions) and Cys residues, and stop codons. More specifically, Asn residues were allowed at the first position of trimers and at the first or second position of tetramers whenever the subsequent amino acid was not Gly and the next amino acid was not Ser or Thr, thus avoiding deamidation or N-linked glycosylation motifs within the candidate N2 segments. The N2 theoretical segment pool for the currently exemplified library contains one zero-mer (i.e., no N2 segment), 18 monomer, 279 dimer, 339 trimers, and 90 tetramer N2 amino acid sequences, or 727 segments in total. These amino acid sequences are encoded by 1, 18, 81, 36, and 10 oligonucleotides, respectively, for a total of 146 oligonucleotides. All but the first 19 oligonucleotides, those encoding the zero- and one-mers, are degenerate. Table 29 lists the 146 oligonucleotide sequences, while Table 30 lists the resulting 727 unique polypeptide sequences.

Example 15. Generation of Expanded H3-JH Diversity

Application of nucleotide-level progressive deletions on the 5' end of the human IGHJ polynucleotide segments down to the point where only the DNA sequence corresponding to FRM4 remained (i.e., no H3-JH remained), followed by systematic 1- or 2-bp completions on the same 5' end, resulted in 643 unique H3-JH peptide segments after translation ("643 H3-JH Set"). As done with the DH segments, it is possible to rank order each of the 643 segments by their usage weights obtained after comparison to the approximately 237,000 human sequences from Boyd et al., and the top 200 individual sequences, from those devoid of the undesired motifs described above, were chosen to provide the set of H3-JH segments for the currently exemplified library.

In an alternatively exemplified embodiment, 46 of the 200 H3-JH segments were designed with a two-fold degenerate codon in the first position (i.e., N-terminal or 5' end, respectively, at the peptide and oligonucleotide level), so that, overall, 200 oligonucleotides would encode 246 unique peptide sequences.

In yet other alternatively exemplified embodiments, further use of degenerate codons may be conceived to produce libraries encoded by 90, 100, 200 or more oligonucleotides representing up to 500 distinct polypeptide sequences. Preferably, but not necessarily, these up to 500 unique sequences could be a subset of the sequences in the 643 H3-JH reference set described above, or a subset of variants of these sequences. As exemplified above, H3-JH segments containing undesirable polypeptide motifs may be eliminated from the design. The oligonucleotide sequences for the JH segments are listed on Table 31, while the resulting unique polypeptide sequences are provided in Table 32. In Table 31, nucleotide sequences corresponding to the FRM4 region are also provided, but the "peptide length" value refers to the H3-JH portion only. For simplicity, only the H3-JH peptide sequences are included in Table 32.

Example 16. Extended Diversity Library Design (EDLD)

The TN1, DH, H3-JH, and N2 segments selected above, and provided in Tables 26 to 32, were combined to generate an Extended Diversity Library Design (EDLD) with theoretical diversity of about $2 \times 10^{11}$ (300 TN1×3,779 DH x 727 N2×246 H3-JH). The oligonucleotides encoding the selected segments were chosen according to the principles of Example 9.3.7.

Figure 12:
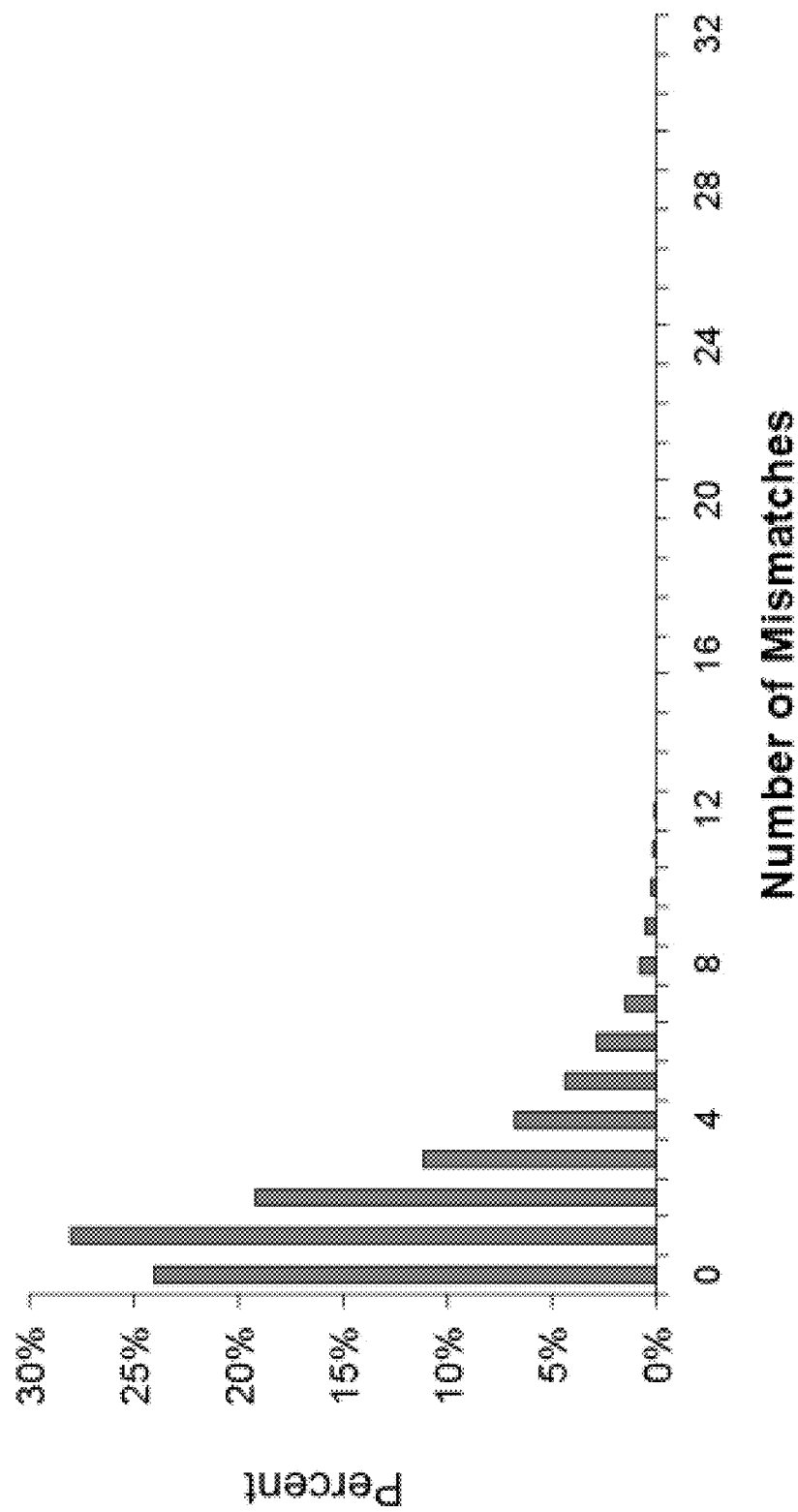
FIG. 12 shows the percentage of CDRH3 sequences in the Extended Diversity library that match CDRH3 sequences from Boyd et al. with zero to thirty-two amino acid mismatches
Figure 13:
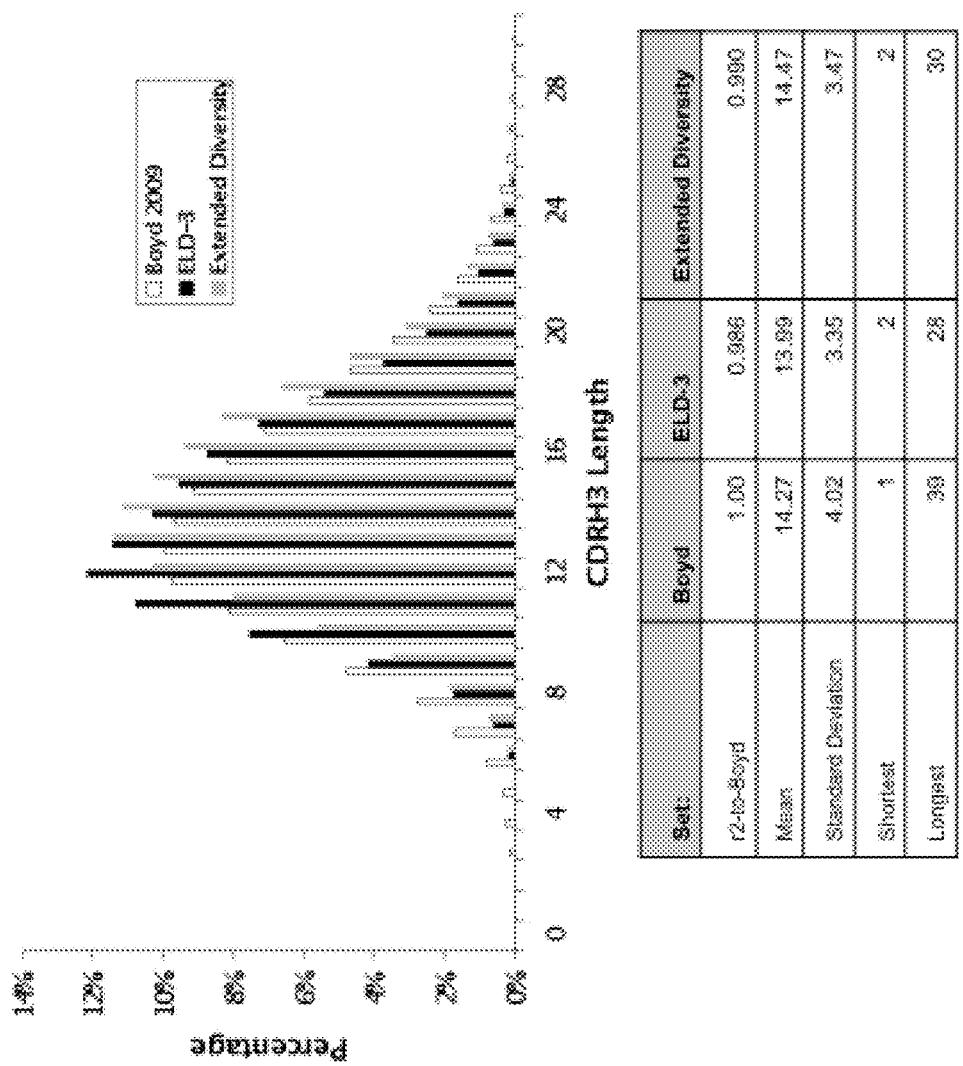
FIG. 13 shows the Kabat-CDRH3 length distribution of Exemplary Library Design 3 ("ELD-3"), the Extended Diversity Library Design ("Extended Diversity") and human CDRH3 sequences from the Boyd et al. data set ("Boyd 2009").
Figure 14:
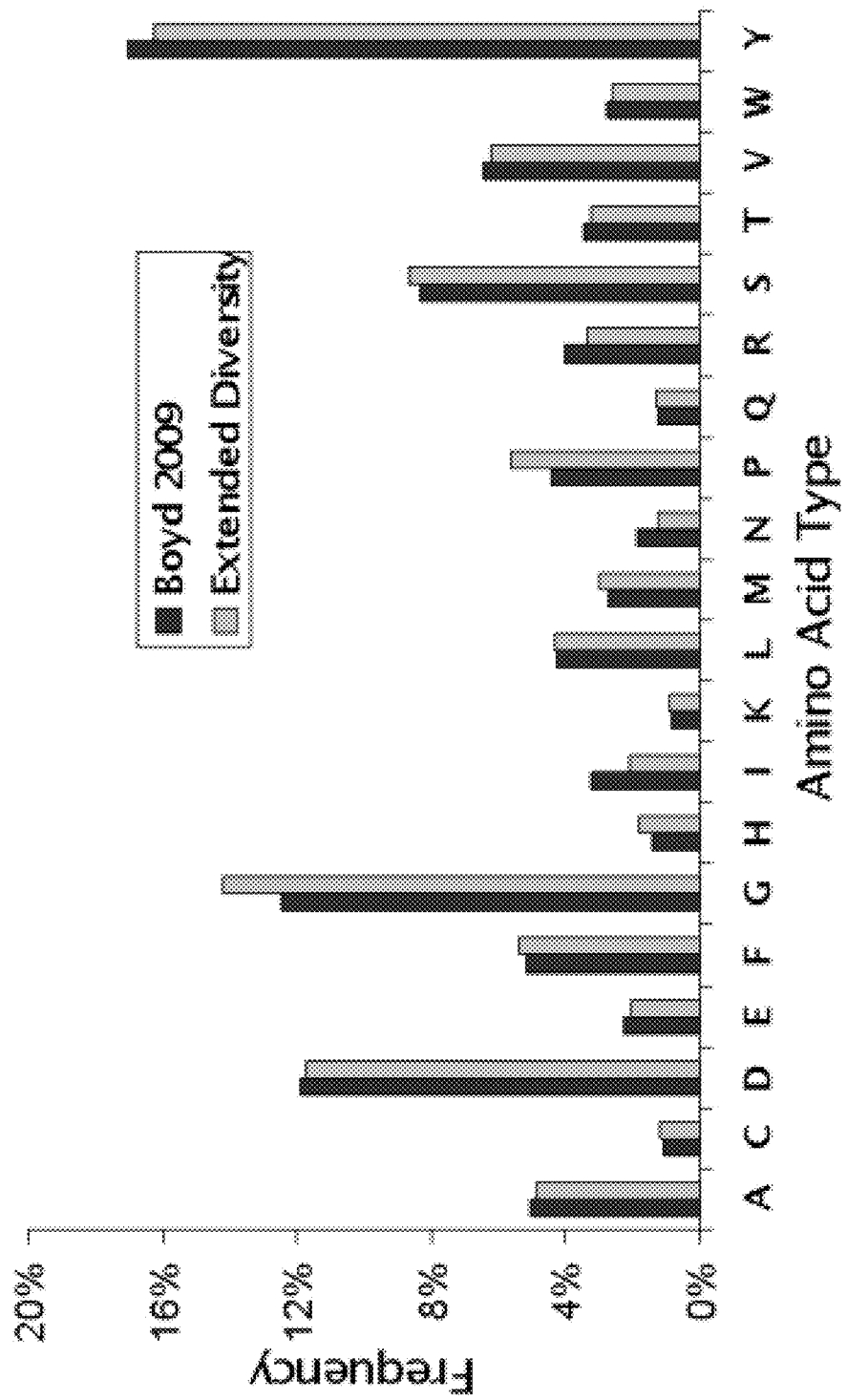
FIG. 14 shows the amino acid compositions of the Kabat-CDRH3s of the Extended Diversity Library Design ("Extended Diversity") and human CDRH3 sequences from the Boyd et al. dataset ("Boyd 2009").
Figure 15:
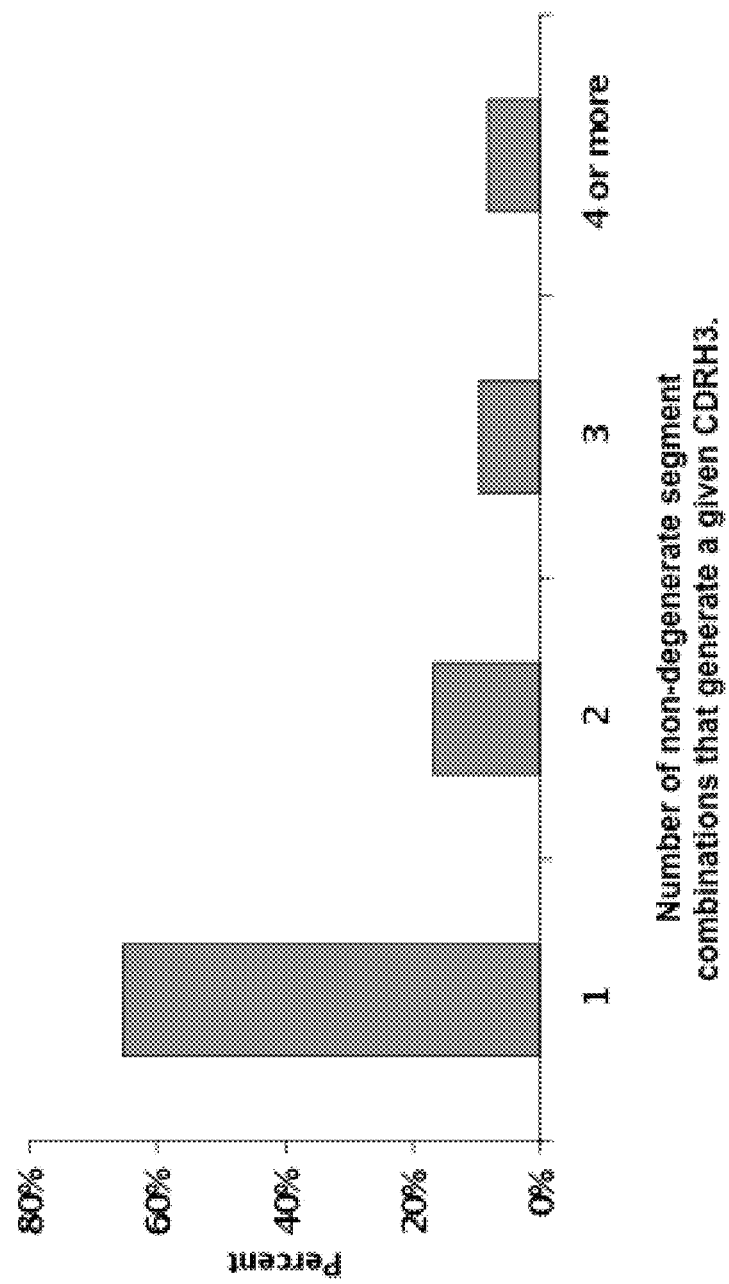
FIG. 15 shows the combinatorial efficiency of the Extended Diversity Library Design by matching 20,000 randomly selected sequences from the (same) design. About 65% of the sequences appear only once in the design and about 17% appear twice.

FIGS. 12-15 illustrate certain characteristics of this design indicating, for example, that about 50% of the approximately 237,000 CDRH3 sequences in Boyd et al. may be recapitulated by library sequences with either one or no mismatches (i.e., by summing the "0" and "1" bins of FIG. 12). The theoretical length distributions (FIG. 13) and amino acid compositions (FIG. 14) of these libraries also match closely the respective characteristics observed in the same set of human CDRH3 sequences. FIG. 15 shows the combinatorial efficiency of the Extended Diversity Library Design. Approximately 65% of the sequences appear only once in the design (i.e., are generated via one non-degenerate combination of segments). FIG. 8, previously presented, shows that the Extended Diversity Library Design outperforms both LUA-141 and ELD-3 in terms of matching to clinically relevant human antibody sequences.

Lengthy table referenced here

US10138478-20181127-T00001

Please refer to the end of the specification for access instructions.

Lengthy table referenced here

US10138478-20181127-T00002

Please refer to the end of the specification for access instructions.

Lengthy table referenced here

US10138478-20181127-T00003

Please refer to the end of the specification for access instructions.

Lengthy table referenced here

US10138478-20181127-T00004

Please refer to the end of the specification for access instructions.

Lengthy table referenced here

US10138478-20181127-T00005

Please refer to the end of the specification for access instructions.

Lengthy table referenced here

US10138478-20181127-T00006

Please refer to the end of the specification for access instructions.

Lengthy table referenced here
US10138478-20181127-T00007
Please refer to the end of the specification for access instructions.

Lengthy table referenced here
US10138478-20181127-T00008
Please refer to the end of the specification for access instructions.

Lengthy table referenced here
US10138478-20181127-T00009
Please refer to the end of the specification for access instructions.

Lengthy table referenced here
US10138478-20181127-T00010
Please refer to the end of the specification for access instructions.

Lengthy table referenced here
US10138478-20181127-T00011
Please refer to the end of the specification for access instructions.

Lengthy table referenced here
US10138478-20181127-T00012
Please refer to the end of the specification for access instructions.

Lengthy table referenced here
US10138478-20181127-T00013
Please refer to the end of the specification for access instructions.

Lengthy table referenced here
US10138478-20181127-T00014
Please refer to the end of the specification for access instructions.

Lengthy table referenced here
US10138478-20181127-T00015
Please refer to the end of the specification for access instructions.

Lengthy table referenced here
US10138478-20181127-T00016
Please refer to the end of the specification for access instructions.

Lengthy table referenced here
US10138478-20181127-T00017
Please refer to the end of the specification for access instructions.

Lengthy table referenced here
US10138478-20181127-T00018
Please refer to the end of the specification for access instructions.

Lengthy table referenced here
US10138478-20181127-T00019
Please refer to the end of the specification for access instructions.

Lengthy table referenced here
US10138478-20181127-T00020
Please refer to the end of the specification for access instructions.

Lengthy table referenced here
US10138478-20181127-T00021
Please refer to the end of the specification for access instructions.

Lengthy table referenced here
US10138478-20181127-T00022
Please refer to the end of the specification for access instructions.

Lengthy table referenced here
US10138478-20181127-T00023
Please refer to the end of the specification for access instructions.

Lengthy table referenced here
US10138478-20181127-T00024
Please refer to the end of the specification for access instructions.

Lengthy table referenced here

US10138478-20181127-T00025

Please refer to the end of the specification for access instructions.

Lengthy table referenced here

US10138478-20181127-T00026

Please refer to the end of the specification for access instructions.

Lengthy table referenced here

US10138478-20181127-T00027

Please refer to the end of the specification for access instructions.

Lengthy table referenced here

US10138478-20181127-T00028

Please refer to the end of the specification for access instructions.

Lengthy table referenced here

US10138478-20181127-T00029

Please refer to the end of the specification for access instructions.

Lengthy table referenced here

US10138478-20181127-T00030

Please refer to the end of the specification for access instructions.

Lengthy table referenced here

US10138478-20181127-T00031

Please refer to the end of the specification for access instructions.

Lengthy table referenced here

US10138478-20181127-T00032

Please refer to the end of the specification for access instructions.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

APPENDIX A

| GI NUMBERS OF 3,571 SEQUENCES IN THE HEALTHY PREIMMUNE SET (HPS) | | | |
|---|---|---|---|
| 33628 | 1052674 | 1685242 | 1770847 |
| 37745 | 1052676 | 1685246 | 1770848 |
| 37747 | 1052683 | 1685248 | 1770851 |
| 37749 | 1052685 | 1685250 | 1770852 |
| 37751 | 1052691 | 1685252 | 1770853 |
| 37753 | 1052692 | 1685254 | 1770854 |
| 37755 | 1052693 | 1685256 | 1770855 |
| 37757 | 1052695 | 1685258 | 1770860 |
| 37759 | 1154682 | 1685260 | 1770861 |
| 37761 | 1154691 | 1685264 | 1770865 |
| 37763 | 1154698 | 1685266 | 1770866 |
| 37765 | 1154699 | 1685268 | 1770867 |
| 37767 | 1154706 | 1770744 | 1770869 |
| 37769 | 1154710 | 1770746 | 1770870 |
| 37773 | 1154713 | 1770747 | 1770872 |
| 37777 | 1154715 | 1770751 | 1770874 |
| 38383 | 1154724 | 1770755 | 1770875 |
| 38391 | 1154754 | 1770756 | 1770876 |
| 38393 | 1154769 | 1770758 | 1770877 |
| 38397 | 1154770 | 1770759 | 1770878 |
| 38401 | 1154805 | 1770761 | 1770879 |
| 185292 | 1154807 | 1770763 | 1770880 |
| 264183 | 1154808 | 1770765 | 1770881 |
| 297147 | 1154809 | 1770766 | 1770882 |
| 306949 | 1154810 | 1770770 | 1770883 |
| 306951 | 1154811 | 1770771 | 1770884 |
| 306953 | 1154813 | 1770772 | 1770885 |
| 483332 | 1154818 | 1770775 | 1770887 |
| 483333 | 1154820 | 1770776 | 1770888 |
| 483335 | 1154822 | 1770777 | 1770891 |
| 483336 | 1154824 | 1770779 | 1770892 |
| 483338 | 1154825 | 1770780 | 1770893 |
| 483339 | 1154834 | 1770783 | 1770894 |
| 483348 | 1154837 | 1770784 | 1770895 |
| 483350 | 1154838 | 1770785 | 1770896 |
| 510999 | 1154839 | 1770789 | 1770898 |
| 547164 | 1154840 | 1770791 | 1770902 |
| 587252 | 1154841 | 1770792 | 1770904 |
| 587254 | 1154843 | 1770793 | 1770905 |
| 587266 | 1154844 | 1770794 | 1770906 |
| 587276 | 1154845 | 1770795 | 1770908 |
| 587278 | 1154847 | 1770796 | 1770909 |
| 587280 | 1154848 | 1770797 | 1770910 |
| 587286 | 1197299 | 1770799 | 1770911 |
| 587288 | 1197300 | 1770800 | 1770912 |
| 587291 | 1197304 | 1770801 | 1770913 |
| 587293 | 1197307 | 1770805 | 1770914 |
| 587295 | 1197308 | 1770806 | 1770915 |
| 587299 | 1197309 | 1770807 | 1770916 |
| 587301 | 1197312 | 1770808 | 1770918 |
| 587304 | 1197313 | 1770809 | 1770922 |
| 587306 | 1197314 | 1770810 | 1770932 |
| 587308 | 1197315 | 1770811 | 1770936 |
| 587311 | 1197316 | 1770812 | 1770937 |
| 587313 | 1197318 | 1770813 | 1770950 |
| 587315 | 1197319 | 1770814 | 1770952 |
| 587317 | 1197321 | 1770815 | 1770954 |
| 1052611 | 1197322 | 1770816 | 1770958 |
| 1052620 | 1197323 | 1770817 | 1770961 |
| 1052622 | 1197324 | 1770818 | 1770962 |
| 1052626 | 1197325 | 1770820 | 1770963 |
| 1052627 | 1197326 | 1770822 | 1770964 |
| 1052634 | 1197327 | 1770824 | 1770967 |
| 1052637 | 1197328 | 1770826 | 1770969 |
| 1052639 | 1495508 | 1770829 | 1770971 |
| 1052640 | 1495511 | 1770830 | 1770972 |
| 1052642 | 1495512 | 1770831 | 1770974 |
| 1052644 | 1495516 | 1770833 | 1770976 |
| 1052655 | 1495518 | 1770835 | 1770979 |
| 1052656 | 1592729 | 1770836 | 1770981 |
| 1052657 | 1685210 | 1770837 | 1770982 |
| 1052658 | 1685220 | 1770839 | 1770983 |
| 1052659 | 1685222 | 1770840 | 1770989 |
| 1052662 | 1685228 | 1770843 | 1770992 |
| 1052668 | 1685234 | 1770844 | 1770994 |
| 1052669 | 1685238 | 1770845 | 1770995 |
| 1052671 | 1685240 | 1770846 | 1770997 |

APPENDIX A-continued

GI NUMBERS OF 3,571 SEQUENCES IN THE HEALTHY PREIMMUNE SET (HPS)

| | | | |
|---|---|---|---|
| 1770998 | 1791142 | 3170752 | 3170974 |
| 1771002 | 1791144 | 3170754 | 3170978 |
| 1771004 | 1791152 | 3170756 | 3170980 |
| 1771008 | 1791154 | 3170758 | 3170984 |
| 1771010 | 1791160 | 3170760 | 3170986 |
| 1771014 | 1791164 | 3170762 | 3170988 |
| 1771016 | 1791176 | 3170764 | 3170990 |
| 1771017 | 1791182 | 3170766 | 3170992 |
| 1771018 | 1791184 | 3170768 | 3171006 |
| 1771022 | 1791186 | 3170772 | 3171008 |
| 1771026 | 1791190 | 3170774 | 3171010 |
| 1771027 | 1791194 | 3170778 | 3171016 |
| 1771029 | 1791196 | 3170782 | 3171018 |
| 1771033 | 1791200 | 3170784 | 3171020 |
| 1771034 | 1791204 | 3170786 | 3171022 |
| 1771035 | 1791206 | 3170788 | 3171024 |
| 1771036 | 1869905 | 3170794 | 3171026 |
| 1771038 | 1869907 | 3170796 | 3171028 |
| 1771039 | 1869912 | 3170802 | 3171030 |
| 1771042 | 1869913 | 3170808 | 3171038 |
| 1771044 | 1869915 | 3170810 | 3171040 |
| 1771045 | 1869918 | 3170812 | 3171042 |
| 1771055 | 1869919 | 3170816 | 3171044 |
| 1771057 | 1934921 | 3170820 | 3171242 |
| 1771058 | 2367538 | 3170822 | 3608440 |
| 1771059 | 2388836 | 3170824 | 3608462 |
| 1771060 | 2388837 | 3170826 | 3954953 |
| 1771061 | 2388839 | 3170830 | 3954955 |
| 1771063 | 2388840 | 3170832 | 4530538 |
| 1791008 | 2388841 | 3170834 | 4530544 |
| 1791010 | 2388842 | 3170836 | 4753741 |
| 1791012 | 2388843 | 3170840 | 4959477 |
| 1791018 | 2388846 | 3170842 | 4995315 |
| 1791020 | 2388847 | 3170844 | 4995317 |
| 1791026 | 2388848 | 3170846 | 4995319 |
| 1791028 | 2388851 | 3170848 | 4995321 |
| 1791030 | 2388852 | 3170852 | 4995323 |
| 1791032 | 2388853 | 3170854 | 4995325 |
| 1791034 | 2388856 | 3170856 | 4995327 |
| 1791036 | 2388859 | 3170858 | 4995329 |
| 1791040 | 2388861 | 3170862 | 4995331 |
| 1791042 | 2388862 | 3170864 | 4995333 |
| 1791046 | 2388863 | 3170866 | 4995335 |
| 1791050 | 2388864 | 3170868 | 4995337 |
| 1791052 | 2388865 | 3170870 | 4995339 |
| 1791054 | 2388868 | 3170872 | 4995341 |
| 1791058 | 2388871 | 3170874 | 4995343 |
| 1791060 | 2388873 | 3170876 | 4995345 |
| 1791062 | 2388875 | 3170878 | 4995347 |
| 1791064 | 2388876 | 3170880 | 4995349 |
| 1791072 | 2388878 | 3170882 | 4995351 |
| 1791074 | 2773082 | 3170884 | 4995353 |
| 1791076 | 3170658 | 3170890 | 4995355 |
| 1791078 | 3170662 | 3170894 | 4995357 |
| 1791080 | 3170664 | 3170898 | 4995359 |
| 1791082 | 3170668 | 3170902 | 4995361 |
| 1791084 | 3170670 | 3170908 | 4995365 |
| 1791086 | 3170686 | 3170910 | 4995367 |
| 1791088 | 3170688 | 3170916 | 4995375 |
| 1791090 | 3170692 | 3170918 | 4995383 |
| 1791096 | 3170694 | 3170922 | 4995385 |
| 1791098 | 3170696 | 3170924 | 4995389 |
| 1791100 | 3170702 | 3170926 | 4995391 |
| 1791104 | 3170704 | 3170930 | 4995393 |
| 1791106 | 3170712 | 3170932 | 4995397 |
| 1791108 | 3170714 | 3170934 | 4995399 |
| 1791110 | 3170716 | 3170936 | 4995400 |
| 1791112 | 3170720 | 3170938 | 4995404 |
| 1791114 | 3170722 | 3170944 | 4995406 |
| 1791116 | 3170726 | 3170946 | 4995408 |
| 1791118 | 3170728 | 3170954 | 4995410 |
| 1791122 | 3170730 | 3170958 | 4995418 |
| 1791124 | 3170734 | 3170960 | 4995422 |
| 1791130 | 3170736 | 3170964 | 4995426 |
| 1791132 | 3170738 | 3170966 | 4995428 |
| 1791134 | 3170740 | 3170968 | 4995430 |
| 1791136 | 3170748 | 3170970 | 4995432 |
| 4995434 | 5834089 | 6531600 | 8489286 |
| 4995436 | 5834091 | 6723523 | 8489289 |
| 4995438 | 5834093 | 6723525 | 8489291 |
| 4995440 | 5834095 | 6723527 | 11137164 |
| 4995442 | 5834097 | 6723531 | 11137170 |
| 4995446 | 5834099 | 6723535 | 11137172 |
| 4995456 | 5834101 | 6723537 | 11137174 |
| 4995462 | 5834103 | 6723543 | 11137178 |
| 4995466 | 5834105 | 6723545 | 11137183 |
| 4995470 | 5834107 | 6723549 | 11137186 |
| 4995474 | 5834109 | 6723551 | 11137188 |
| 4995476 | 5834113 | 6723558 | 11137196 |
| 4995478 | 5834115 | 6723565 | 11137200 |
| 4995480 | 5834119 | 6723581 | 11137205 |
| 4995482 | 5834121 | 6723583 | 11137215 |
| 4995484 | 5834123 | 6723595 | 11137219 |
| 4995486 | 5834125 | 6723597 | 11137229 |
| 4995488 | 5834127 | 6723599 | 11137231 |
| 4995490 | 5834129 | 7161042 | 11137242 |
| 4995492 | 5834131 | 7161061 | 11137251 |
| 4995494 | 5834133 | 7161129 | 11137253 |
| 4995496 | 5834135 | 7161136 | 11137261 |
| 4995498 | 5834137 | 7161164 | 11137262 |
| 4995500 | 5834139 | 8249510 | 11137274 |
| 4995502 | 5834141 | 8249514 | 11137276 |
| 4995504 | 5834143 | 8249518 | 11137279 |
| 4995506 | 5834145 | 8249524 | 11137281 |
| 4995508 | 5834147 | 8249528 | 11137283 |
| 4995510 | 5834149 | 8249538 | 11137285 |
| 4995512 | 5834151 | 8249546 | 11137289 |
| 4995514 | 5834153 | 8249552 | 11137290 |
| 4995516 | 5834155 | 8249554 | 11137293 |
| 4995520 | 5834159 | 8249558 | 11137295 |
| 4995524 | 5834161 | 8249560 | 11137298 |
| 4995530 | 5834163 | 8249562 | 11137301 |
| 4995535 | 5834165 | 8249566 | 11137303 |
| 4995537 | 5834169 | 8249568 | 11137305 |
| 4995539 | 5834175 | 8249608 | 11137307 |
| 4995549 | 5834177 | 8249622 | 11137309 |
| 4995555 | 5834179 | 8249632 | 11137313 |
| 4995557 | 5834183 | 8249650 | 11137315 |
| 4995563 | 5834185 | 8249652 | 11137317 |
| 4995569 | 5834187 | 8249654 | 11137319 |
| 4995575 | 5834191 | 8249656 | 11137322 |
| 4995581 | 5834193 | 8249662 | 11137326 |
| 4995589 | 5834195 | 8249674 | 11137329 |
| 4995591 | 5834197 | 8249682 | 11137333 |
| 5833973 | 5834199 | 8249698 | 11137335 |
| 5833980 | 5834201 | 8249712 | 11137339 |
| 5833984 | 5834203 | 8249716 | 11137343 |
| 5833986 | 5834205 | 8249718 | 11137348 |
| 5834003 | 5834207 | 8249730 | 11137350 |
| 5834011 | 5834209 | 8249738 | 11137352 |
| 5834015 | 5834213 | 8249740 | 11137354 |
| 5834019 | 5834215 | 8249744 | 11137359 |
| 5834031 | 6013039 | 8249754 | 11137361 |
| 5834035 | 6013043 | 8249756 | 11137363 |
| 5834037 | 6013045 | 8249760 | 11137365 |
| 5834039 | 6531445 | 8249772 | 11137367 |
| 5834041 | 6531457 | 8249778 | 11137369 |
| 5834043 | 6531461 | 8249784 | 11137371 |
| 5834047 | 6531465 | 8249786 | 11137373 |
| 5834049 | 6531481 | 8249788 | 11137375 |
| 5834051 | 6531489 | 8249790 | 11137377 |
| 5834053 | 6531493 | 8249812 | 11137379 |
| 5834055 | 6531495 | 8249816 | 11137382 |
| 5834057 | 6531507 | 8249826 | 11137386 |
| 5834059 | 6531509 | 8249828 | 11137388 |
| 5834065 | 6531511 | 8249838 | 11137392 |
| 5834069 | 6531513 | 8250248 | 11137399 |
| 5834071 | 6531517 | 8250255 | 11137403 |
| 5834073 | 6531521 | 8489274 | 11137407 |
| 5834075 | 6531525 | 8489276 | 11137411 |
| 5834077 | 6531533 | 8489278 | 11137413 |
| 5834079 | 6531537 | 8489280 | 11137415 |
| 5834081 | 6531539 | 8489282 | 11137418 |
| 5834083 | 6531554 | 8489284 | 11137420 |

APPENDIX A-continued

GI NUMBERS OF 3,571 SEQUENCES IN THE HEALTHY PREIMMUNE SET (HPS)

| | | | | | | | |
|---|---|---|---|---|---|---|---|
| 11137422 | 13172069 | 21702275 | 47846518 | 49523837 | 54779258 | 54780723 | 145910938 |
| 11137426 | 13172073 | 21702277 | 47846520 | 49523841 | 54779260 | 54780731 | 145910942 |
| 11137428 | 13172083 | 21702281 | 47846524 | 49523843 | 54779262 | 54780733 | 145910945 |
| 11137430 | 13172091 | 21702282 | 47846526 | 49523849 | 54779264 | 54780735 | 145910949 |
| 11137432 | 13172093 | 21702287 | 47846528 | 49523851 | 54779266 | 54780741 | 145910952 |
| 11137439 | 13172099 | 21702289 | 47846530 | 49523853 | 54779268 | 54780745 | 145910955 |
| 11137441 | 13172117 | 21702291 | 47846532 | 49523855 | 54779270 | 54780753 | 145910958 |
| 11137445 | 13172125 | 21702293 | 47846534 | 49523861 | 54779272 | 54780757 | 145910966 |
| 11137448 | 13172129 | 21702295 | 47846538 | 49523865 | 54779274 | 54780759 | 145910969 |
| 11137450 | 13172133 | 21702297 | 47846540 | 49523871 | 54779276 | 54780761 | 145910972 |
| 11137452 | 13172135 | 21702299 | 47846542 | 49523873 | 54779278 | 54780763 | 145910975 |
| 11137454 | 13172137 | 21702301 | 47846544 | 49523879 | 54779280 | 54780765 | 145910983 |
| 11137460 | 13172141 | 21702303 | 47846546 | 49523881 | 54779282 | 54780767 | 145910986 |
| 11137462 | 13172143 | 21702305 | 47846548 | 49523887 | 54779284 | 54780771 | 145910989 |
| 11137467 | 13172147 | 21702307 | 47846550 | 49523895 | 54779286 | 54780775 | 145910992 |
| 11137470 | 13172149 | 21702309 | 47846558 | 49523905 | 54779288 | 54780777 | 145910995 |
| 11137474 | 13172151 | 21702311 | 47846562 | 49523919 | 54779290 | 54780779 | 145910998 |
| 11137476 | 13172155 | 21702313 | 47846564 | 49523921 | 54779292 | 54780781 | 145911001 |
| 11137480 | 13172157 | 21702314 | 47846566 | 49523923 | 54779296 | 54780783 | 145911004 |
| 11137482 | 13172159 | 21702315 | 47846570 | 49523927 | 54779298 | 54780785 | 145911013 |
| 11137487 | 13172163 | 23337033 | 47846572 | 49523929 | 54779300 | 54780787 | 145911017 |
| 11137494 | 13172169 | 27370812 | 47846574 | 49523931 | 54779302 | 54780791 | 145911020 |
| 11137500 | 13172177 | 31076438 | 47846578 | 49523946 | 54779306 | 54780793 | 145911023 |
| 11137502 | 13623574 | 33873883 | 47846580 | 49523950 | 54779308 | 54780795 | 145911026 |
| 11137507 | 14289029 | 33989177 | 47846582 | 54779136 | 54779310 | 54780801 | 145911029 |
| 11137509 | 14289035 | 37987904 | 47846586 | 54779140 | 54779314 | 54780803 | 145911032 |
| 13171905 | 14289037 | 37987932 | 47846588 | 54779142 | 54779316 | 54780805 | 145911038 |
| 13171909 | 14289049 | 37987938 | 47846590 | 54779144 | 54779318 | 54780807 | 145911041 |
| 13171911 | 14289057 | 37987960 | 47846594 | 54779146 | 54779320 | 54780809 | 145911044 |
| 13171913 | 14289061 | 37987970 | 47846596 | 54779148 | 54779322 | 54780815 | 145911047 |
| 13171915 | 14289065 | 39644659 | 47846598 | 54779150 | 54779324 | 54780817 | 145911050 |
| 13171917 | 14289067 | 39645530 | 47846600 | 54779152 | 54779328 | 54780821 | 145911053 |
| 13171921 | 14289071 | 47846366 | 47846602 | 54779156 | 54779330 | 54780825 | 145911061 |
| 13171923 | 14289073 | 47846370 | 47846604 | 54779158 | 54779332 | 54780827 | 145911064 |
| 13171925 | 14289079 | 47846372 | 47846606 | 54779160 | 54779334 | 54780831 | 145911072 |
| 13171927 | 14289097 | 47846376 | 47846612 | 54779162 | 54779336 | 54780833 | 145911075 |
| 13171929 | 14289099 | 47846378 | 47846614 | 54779166 | 54779338 | 54780835 | 145911081 |
| 13171931 | 14289109 | 47846380 | 47846618 | 54779168 | 54779340 | 54780837 | 145911086 |
| 13171935 | 14289111 | 47846386 | 47846620 | 54779170 | 54779342 | 54780839 | 145911090 |
| 13171937 | 16075408 | 47846388 | 47846626 | 54779172 | 54779344 | 54780841 | 145911092 |
| 13171939 | 16075410 | 47846394 | 47846632 | 54779174 | 54779350 | 54780843 | 145911096 |
| 13171941 | 16075412 | 47846398 | 47846644 | 54779178 | 54779354 | 54780845 | 145911102 |
| 13171945 | 16075414 | 47846416 | 47846646 | 54779180 | 54779356 | 54780847 | 145911105 |
| 13171947 | 16075416 | 47846418 | 47846658 | 54779182 | 54779358 | 54780853 | 145911108 |
| 13171949 | 16075418 | 47846420 | 47846660 | 54779184 | 54779360 | 54780857 | 145911111 |
| 13171951 | 16075420 | 47846422 | 47846664 | 54779186 | 54779362 | 54780859 | 145911133 |
| 13171953 | 16075422 | 47846426 | 47846666 | 54779188 | 54779364 | 54780861 | 145911150 |
| 13171955 | 16075424 | 47846428 | 47846674 | 54779190 | 54780155 | 54780863 | 145911156 |
| 13171957 | 16075426 | 47846430 | 47846678 | 54779192 | 54780163 | 55228577 | 145911159 |
| 13171959 | 16075428 | 47846432 | 47846680 | 54779194 | 54780167 | 55228579 | 145911162 |
| 13171961 | 16075430 | 47846434 | 47846684 | 54779196 | 54780171 | 55228584 | 145911165 |
| 13171965 | 16075432 | 47846438 | 47846690 | 54779198 | 54780177 | 55228638 | 145911171 |
| 13171967 | 16075434 | 47846442 | 47846692 | 54779200 | 54780179 | 55228640 | 145911174 |
| 13171969 | 16075436 | 47846446 | 47846696 | 54779204 | 54780185 | 55228646 | 145911177 |
| 13171971 | 16075438 | 47846448 | 47846698 | 54779206 | 54780187 | 55228650 | 145911180 |
| 13171973 | 16075440 | 47846450 | 47846716 | 54779208 | 54780191 | 55228651 | 145911183 |
| 13171975 | 16075442 | 47846456 | 47846718 | 54779210 | 54780193 | 55228652 | 145911186 |
| 13171977 | 16075444 | 47846458 | 47846724 | 54779212 | 54780209 | 60688113 | 145911190 |
| 13171981 | 16075448 | 47846466 | 47846728 | 54779214 | 54780211 | 74095346 | 145911193 |
| 13171987 | 16075450 | 47846468 | 47846730 | 54779218 | 54780213 | 74095348 | 145911199 |
| 13171999 | 16075452 | 47846472 | 47846734 | 54779220 | 54780227 | 74095350 | 145911202 |
| 13172003 | 16075454 | 47846476 | 47846750 | 54779222 | 54780229 | 74095355 | 145911205 |
| 13172005 | 16075456 | 47846478 | 47846752 | 54779224 | 54780235 | 74095358 | 145911214 |
| 13172007 | 16075458 | 47846482 | 47846756 | 54779226 | 54780237 | 91979763 | 145911217 |
| 13172009 | 16075460 | 47846484 | 47846762 | 54779228 | 54780239 | 91979789 | 145911220 |
| 13172013 | 16075464 | 47846486 | 47846764 | 54779230 | 54780243 | 91979839 | 145911223 |
| 13172019 | 16075466 | 47846488 | 47846768 | 54779232 | 54780247 | 91979849 | 145911226 |
| 13172021 | 16076074 | 47846490 | 47846778 | 54779234 | 54780251 | 111918091 | 145911235 |
| 13172025 | 16076286 | 47846492 | 47846782 | 54779236 | 54780253 | 111918116 | 145911238 |
| 13172027 | 17511791 | 47846494 | 47846784 | 54779238 | 54780259 | 111918127 | 145911248 |
| 13172033 | 18044958 | 47846498 | 47846786 | 54779240 | 54780709 | 111918184 | 145911257 |
| 13172037 | 19171939 | 47846506 | 49256420 | 54779242 | 54780711 | 111918251 | 145911287 |
| 13172043 | 19550754 | 47846508 | 49256426 | 54779244 | 54780713 | 111918262 | 145911291 |
| 13172045 | 19848531 | 47846510 | 49258105 | 54779248 | 54780715 | 111918647 | 145911294 |
| 13172053 | 19848533 | 47846512 | 49523831 | 54779250 | 54780717 | 121488404 | 145911298 |
| 13172061 | 19848543 | 47846514 | 49523833 | 54779252 | 54780719 | 145910925 | 145911301 |
| 13172065 | 19848545 | 47846516 | 49523835 | 54779256 | 54780721 | 145910934 | 145911305 |

APPENDIX A-continued

GI NUMBERS OF 3,571 SEQUENCES IN THE
HEALTHY PREIMMUNE SET (HPS)

| | | | |
|---|---|---|---|
| 145911308 | 145911823 | 145912707 | 145913746 |
| 145911311 | 145911832 | 145912717 | 145913752 |
| 145911314 | 145911840 | 145912725 | 145913757 |
| 145911317 | 145911849 | 145912735 | 145913766 |
| 145911320 | 145911857 | 145912744 | 145913772 |
| 145911323 | 145911883 | 145912753 | 145913777 |
| 145911326 | 145911892 | 145912760 | 145913782 |
| 145911329 | 145911914 | 145912780 | 145913787 |
| 145911332 | 145911936 | 145912790 | 145913792 |
| 145911335 | 145911938 | 145912799 | 145913797 |
| 145911338 | 145911940 | 145912814 | 145913803 |
| 145911341 | 145911942 | 145912824 | 145913808 |
| 145911344 | 145911944 | 145912844 | 145913813 |
| 145911347 | 145911946 | 145912853 | 145913840 |
| 145911350 | 145911948 | 145912861 | 145913852 |
| 145911353 | 145911950 | 145912868 | 145913856 |
| 145911356 | 145911953 | 145912879 | 145913867 |
| 145911359 | 145911959 | 145912888 | 145913875 |
| 145911362 | 145911968 | 145912898 | 145913879 |
| 145911365 | 145911983 | 145912909 | 145913883 |
| 145911368 | 145911992 | 145912919 | 145913888 |
| 145911371 | 145912001 | 145912930 | 145913893 |
| 145911374 | 145912009 | 145912940 | 145913898 |
| 145911377 | 145912023 | 145912949 | 145913902 |
| 145911384 | 145912037 | 145912958 | 145913915 |
| 145911388 | 145912044 | 145912978 | 145913919 |
| 145911391 | 145912059 | 145912996 | 145913921 |
| 145911394 | 145912100 | 145913026 | 145913923 |
| 145911397 | 145912107 | 145913035 | 145913927 |
| 145911400 | 145912114 | 145913042 | 145913929 |
| 145911403 | 145912123 | 145913066 | 145913932 |
| 145911407 | 145912132 | 145913107 | 145913943 |
| 145911410 | 145912152 | 145913138 | 145913955 |
| 145911413 | 145912167 | 145913155 | 145913961 |
| 145911416 | 145912176 | 145913181 | 145913965 |
| 145911421 | 145912186 | 145913209 | 145913969 |
| 145911427 | 145912211 | 145913219 | 145913973 |
| 145911436 | 145912220 | 145913232 | 145913977 |
| 145911442 | 145912229 | 145913236 | 145913980 |
| 145911451 | 145912238 | 145913241 | 145913984 |
| 145911457 | 145912249 | 145913248 | 145913988 |
| 145911466 | 145912260 | 145913257 | 145913991 |
| 145911482 | 145912278 | 145913268 | 145913995 |
| 145911491 | 145912308 | 145913278 | 145914000 |
| 145911498 | 145912353 | 145913288 | 145914004 |
| 145911502 | 145912361 | 145913297 | 145914011 |
| 145911510 | 145912371 | 145913308 | 145914017 |
| 145911517 | 145912381 | 145913344 | 145914020 |
| 145911523 | 145912399 | 145913354 | 145914023 |
| 145911536 | 145912409 | 145913377 | 145914026 |
| 145911544 | 145912418 | 145913386 | 145914038 |
| 145911553 | 145912436 | 145913394 | 145914045 |
| 145911561 | 145912446 | 145913404 | 145914049 |
| 145911568 | 145912456 | 145913415 | 145914056 |
| 145911576 | 145912466 | 145913425 | 145914060 |
| 145911585 | 145912470 | 145913433 | 145914063 |
| 145911597 | 145912479 | 145913470 | 145938277 |
| 145911604 | 145912495 | 145913480 | 145938293 |
| 145911611 | 145912504 | 145913489 | 145938315 |
| 145911618 | 145912508 | 145913518 | 145938332 |
| 145911621 | 145912528 | 145913528 | 145938348 |
| 145911655 | 145912547 | 145913539 | 145938356 |
| 145911663 | 145912566 | 145913549 | 145938362 |
| 145911679 | 145912575 | 145913569 | 145938375 |
| 145911687 | 145912587 | 145913578 | 145938384 |
| 145911695 | 145912589 | 145913588 | 145938391 |
| 145911703 | 145912591 | 145913596 | 145938403 |
| 145911713 | 145912595 | 145913608 | 145938411 |
| 145911722 | 145912598 | 145913620 | 145938421 |
| 145911746 | 145912614 | 145913640 | 145938426 |
| 145911748 | 145912624 | 145913650 | 145938430 |
| 145911750 | 145912635 | 145913660 | 145938438 |
| 145911752 | 145912647 | 145913670 | 145938446 |
| 145911754 | 145912674 | 145913682 | 145938454 |
| 145911768 | 145912682 | 145913687 | 145938462 |
| 145911786 | 145912691 | 145913722 | 145938470 |
| 145911795 | 145912700 | 145913730 | 145938490 |
| 145938504 | 145939392 | 145940316 | 145940902 |
| 145938513 | 145939407 | 145940325 | 145940907 |
| 145938531 | 145939416 | 145940332 | 145940912 |
| 145938537 | 145939432 | 145940340 | 145940917 |
| 145938553 | 145939449 | 145940354 | 145940921 |
| 145938562 | 145939459 | 145940362 | 145940926 |
| 145938570 | 145939470 | 145940370 | 145940940 |
| 145938577 | 145939475 | 145940379 | 145941075 |
| 145938596 | 145939484 | 145940387 | 145941079 |
| 145938621 | 145939501 | 145940399 | 145941083 |
| 145938629 | 145939514 | 145940404 | 145941090 |
| 145938639 | 145939566 | 145940411 | 145941097 |
| 145938647 | 145939578 | 145940416 | 145941111 |
| 145938674 | 145939586 | 145940428 | 145941118 |
| 145938680 | 145939593 | 145940439 | 145941131 |
| 145938689 | 145939602 | 145940441 | 145941134 |
| 145938698 | 145939609 | 145940445 | 145941137 |
| 145938706 | 145939634 | 145940448 | 145941143 |
| 145938713 | 145939643 | 145940450 | 145941151 |
| 145938721 | 145939651 | 145940452 | 145941158 |
| 145938730 | 145939657 | 145940456 | 145941167 |
| 145938737 | 145939670 | 145940461 | 145941176 |
| 145938755 | 145939678 | 145940468 | 145941194 |
| 145938771 | 145939686 | 145940482 | 145941226 |
| 145938808 | 145939694 | 145940489 | 145941231 |
| 145938830 | 145939699 | 145940494 | 145941239 |
| 145938837 | 145939704 | 145940498 | 145941247 |
| 145938865 | 145939707 | 145940508 | 145941255 |
| 145938874 | 145939711 | 145940510 | 145941262 |
| 145938892 | 145939718 | 145940515 | 145941276 |
| 145938899 | 145939724 | 145940520 | 145941296 |
| 145938906 | 145939730 | 145940530 | 145941328 |
| 145938916 | 145939738 | 145940535 | 145941336 |
| 145938926 | 145939747 | 145940541 | 145941349 |
| 145938944 | 145939753 | 145940547 | 145941358 |
| 145938952 | 145939760 | 145940552 | 145941365 |
| 145938969 | 145939766 | 145940557 | 145941373 |
| 145938986 | 145939768 | 145940567 | 145941380 |
| 145938995 | 145939770 | 145940573 | 145941388 |
| 145939005 | 145939776 | 145940583 | 145941393 |
| 145939023 | 145939778 | 145940593 | 145941399 |
| 145939030 | 145939782 | 145940597 | 145941425 |
| 145939044 | 145939788 | 145940602 | 145941459 |
| 145939053 | 145939805 | 145940613 | 145941466 |
| 145939061 | 145939817 | 145940631 | 145941474 |
| 145939069 | 145939824 | 145940636 | 145941483 |
| 145939083 | 145939834 | 145940645 | 145941488 |
| 145939085 | 145939844 | 145940650 | 145941499 |
| 145939087 | 145939858 | 145940656 | 145941505 |
| 145939093 | 145939865 | 145940662 | 145941512 |
| 145939095 | 145939872 | 145940675 | 145941518 |
| 145939097 | 145939879 | 145940681 | 145941539 |
| 145939106 | 145939900 | 145940700 | 145941544 |
| 145939132 | 145939910 | 145940706 | 145941550 |
| 145939147 | 145939921 | 145940711 | 145941558 |
| 145939155 | 145939940 | 145940727 | 145941571 |
| 145939161 | 145939949 | 145940735 | 145941577 |
| 145939169 | 145939970 | 145940742 | 145941588 |
| 145939181 | 145939986 | 145940748 | 145941597 |
| 145939189 | 145940002 | 145940756 | 145941605 |
| 145939197 | 145940029 | 145940762 | 145941618 |
| 145939206 | 145940036 | 145940774 | 145941634 |
| 145939215 | 145940043 | 145940783 | 145941639 |
| 145939231 | 145940052 | 145940789 | 145941644 |
| 145939237 | 145940070 | 145940797 | 145941650 |
| 145939252 | 145940091 | 145940804 | 145941657 |
| 145939271 | 145940115 | 145940818 | 145941669 |
| 145939285 | 145940124 | 145940825 | 145941674 |
| 145939302 | 145940133 | 145940832 | 145941680 |
| 145939309 | 145940152 | 145940838 | 145941685 |
| 145939317 | 145940167 | 145940846 | 145941698 |
| 145939331 | 145940173 | 145940853 | 145941704 |
| 145939338 | 145940190 | 145940858 | 145941717 |
| 145939346 | 145940218 | 145940865 | 145941724 |
| 145939356 | 145940226 | 145940877 | 145941731 |
| 145939367 | 145940239 | 145940884 | 145941745 |
| 145939384 | 145940269 | 145940891 | 145941752 |

APPENDIX A-continued

GI NUMBERS OF 3,571 SEQUENCES IN THE HEALTHY PREIMMUNE SET (HPS)

| | | | |
|---|---|---|---|
| 145941758 | 159034235 | 159034347 | 159034453 |
| 145941764 | 159034236 | 159034348 | 159034455 |
| 145941791 | 159034238 | 159034349 | 159034460 |
| 145941806 | 159034239 | 159034350 | 159034461 |
| 145941819 | 159034240 | 159034354 | 159034462 |
| 145941822 | 159034241 | 159034355 | 159034463 |
| 145941824 | 159034242 | 159034356 | 159034464 |
| 145941828 | 159034243 | 159034358 | 159034465 |
| 145941837 | 159034244 | 159034359 | 159034466 |
| 145941854 | 159034245 | 159034362 | 159034467 |
| 145941863 | 159034249 | 159034364 | 159034468 |
| 145941877 | 159034250 | 159034365 | 159034471 |
| 145941886 | 159034252 | 159034366 | 159034472 |
| 145941908 | 159034253 | 159034367 | 159034474 |
| 145941915 | 159034254 | 159034368 | 159034476 |
| 145941933 | 159034258 | 159034369 | 159034479 |
| 145942086 | 159034259 | 159034370 | 159034481 |
| 145942146 | 159034260 | 159034372 | 159034482 |
| 145942158 | 159034262 | 159034373 | 159034484 |
| 145942175 | 159034266 | 159034375 | 159034485 |
| 145942206 | 159034267 | 159034376 | 159034486 |
| 145942223 | 159034268 | 159034378 | 159034490 |
| 145942261 | 159034273 | 159034379 | 159034492 |
| 145942265 | 159034274 | 159034381 | 159034493 |
| 145942309 | 159034276 | 159034383 | 159034494 |
| 145942383 | 159034277 | 159034384 | 159034495 |
| 145942405 | 159034278 | 159034385 | 159034497 |
| 145942487 | 159034279 | 159034386 | 159034499 |
| 145942497 | 159034280 | 159034387 | 159034500 |
| 145942506 | 159034282 | 159034388 | 159034501 |
| 145942509 | 159034283 | 159034389 | 159034502 |
| 145942544 | 159034284 | 159034390 | 159034503 |
| 145942565 | 159034285 | 159034392 | 159034504 |
| 145942606 | 159034286 | 159034393 | 159034511 |
| 148717962 | 159034287 | 159034395 | 159034512 |
| 148717964 | 159034288 | 159034396 | 159034515 |
| 148717966 | 159034290 | 159034397 | 159034516 |
| 148910865 | 159034291 | 159034398 | 159034518 |
| 159034187 | 159034293 | 159034399 | 159034521 |
| 159034188 | 159034296 | 159034400 | 159034522 |
| 159034189 | 159034297 | 159034402 | 159034523 |
| 159034190 | 159034298 | 159034403 | 159034524 |
| 159034191 | 159034299 | 159034404 | 159034526 |
| 159034192 | 159034300 | 159034405 | 159034527 |
| 159034193 | 159034301 | 159034408 | 159034529 |
| 159034194 | 159034302 | 159034410 | 159034530 |
| 159034195 | 159034303 | 159034414 | 159034531 |
| 159034196 | 159034304 | 159034415 | 159034532 |
| 159034197 | 159034305 | 159034417 | 159034534 |
| 159034198 | 159034306 | 159034419 | 159034535 |
| 159034200 | 159034307 | 159034420 | 159034536 |
| 159034202 | 159034308 | 159034421 | 159034537 |
| 159034203 | 159034309 | 159034422 | 159034538 |
| 159034204 | 159034310 | 159034423 | 159034539 |
| 159034205 | 159034311 | 159034424 | 159034540 |
| 159034207 | 159034313 | 159034425 | 159034541 |
| 159034208 | 159034315 | 159034426 | 159034542 |
| 159034209 | 159034316 | 159034429 | 159034543 |
| 159034211 | 159034318 | 159034430 | 159034545 |
| 159034212 | 159034320 | 159034431 | 159034546 |
| 159034213 | 159034323 | 159034433 | 159034547 |
| 159034214 | 159034324 | 159034434 | 159034549 |
| 159034215 | 159034325 | 159034435 | 159034550 |
| 159034216 | 159034328 | 159034436 | 159034552 |
| 159034217 | 159034329 | 159034438 | 159034554 |
| 159034218 | 159034330 | 159034439 | 159034556 |
| 159034219 | 159034331 | 159034440 | 159034559 |
| 159034222 | 159034335 | 159034441 | 159034562 |
| 159034223 | 159034337 | 159034443 | 159034563 |
| 159034224 | 159034339 | 159034444 | 159034564 |
| 159034225 | 159034340 | 159034445 | 159034565 |
| 159034226 | 159034341 | 159034446 | 159034566 |
| 159034227 | 159034342 | 159034447 | 159034568 |
| 159034228 | 159034343 | 159034448 | 159034570 |
| 159034230 | 159034344 | 159034449 | 159034571 |
| 159034231 | 159034345 | 159034450 | 159034572 |
| 159034233 | 159034346 | 159034451 | 159034573 |
| 159034575 | 159034697 | 159034801 | 159034904 |
| 159034576 | 159034698 | 159034802 | 159034905 |
| 159034578 | 159034699 | 159034804 | 159034906 |
| 159034580 | 159034700 | 159034805 | 159034907 |
| 159034581 | 159034701 | 159034809 | 159034908 |
| 159034582 | 159034704 | 159034811 | 159034909 |
| 159034584 | 159034705 | 159034812 | 159034910 |
| 159034587 | 159034706 | 159034813 | 159034911 |
| 159034588 | 159034708 | 159034815 | 159034912 |
| 159034589 | 159034709 | 159034816 | 159034913 |
| 159034591 | 159034710 | 159034817 | 159034914 |
| 159034596 | 159034711 | 159034818 | 159034917 |
| 159034599 | 159034712 | 159034819 | 159034918 |
| 159034600 | 159034713 | 159034820 | 159034919 |
| 159034601 | 159034714 | 159034821 | 159034920 |
| 159034602 | 159034717 | 159034822 | 159034923 |
| 159034604 | 159034718 | 159034823 | 159034925 |
| 159034607 | 159034720 | 159034824 | 159034926 |
| 159034609 | 159034721 | 159034825 | 159034928 |
| 159034611 | 159034722 | 159034827 | 159034929 |
| 159034612 | 159034725 | 159034828 | 159034931 |
| 159034613 | 159034726 | 159034829 | 159034934 |
| 159034617 | 159034728 | 159034831 | 159034935 |
| 159034619 | 159034729 | 159034832 | 159034936 |
| 159034620 | 159034730 | 159034833 | 159034937 |
| 159034621 | 159034731 | 159034834 | 159034938 |
| 159034622 | 159034732 | 159034835 | 159034939 |
| 159034625 | 159034733 | 159034837 | 159034940 |
| 159034626 | 159034734 | 159034838 | 159034942 |
| 159034628 | 159034736 | 159034839 | 159034945 |
| 159034629 | 159034737 | 159034840 | 159034946 |
| 159034631 | 159034738 | 159034842 | 159034947 |
| 159034632 | 159034741 | 159034843 | 159034948 |
| 159034634 | 159034742 | 159034844 | 159034950 |
| 159034635 | 159034743 | 159034845 | 159034952 |
| 159034636 | 159034744 | 159034846 | 159034953 |
| 159034637 | 159034745 | 159034847 | 159034954 |
| 159034638 | 159034747 | 159034848 | 159034955 |
| 159034640 | 159034748 | 159034849 | 159034957 |
| 159034641 | 159034749 | 159034852 | 159034959 |
| 159034642 | 159034750 | 159034853 | 159034961 |
| 159034643 | 159034751 | 159034856 | 159034962 |
| 159034647 | 159034752 | 159034858 | 159034963 |
| 159034648 | 159034754 | 159034859 | 159034964 |
| 159034649 | 159034756 | 159034860 | 159034965 |
| 159034650 | 159034758 | 159034861 | 159034967 |
| 159034651 | 159034759 | 159034862 | 159034970 |
| 159034652 | 159034760 | 159034863 | 159034971 |
| 159034653 | 159034762 | 159034864 | 159034973 |
| 159034654 | 159034763 | 159034866 | 159034974 |
| 159034657 | 159034764 | 159034869 | 159034975 |
| 159034658 | 159034765 | 159034871 | 159034976 |
| 159034659 | 159034766 | 159034872 | 159034978 |
| 159034660 | 159034767 | 159034874 | 159034980 |
| 159034661 | 159034768 | 159034876 | 159034981 |
| 159034664 | 159034771 | 159034877 | 159034982 |
| 159034665 | 159034773 | 159034879 | 159034983 |
| 159034668 | 159034774 | 159034880 | 159034984 |
| 159034669 | 159034778 | 159034882 | 159034985 |
| 159034672 | 159034779 | 159034883 | 159034987 |
| 159034673 | 159034780 | 159034885 | 159034988 |
| 159034676 | 159034781 | 159034886 | 159034989 |
| 159034677 | 159034782 | 159034887 | 159034991 |
| 159034678 | 159034783 | 159034888 | 159034992 |
| 159034679 | 159034784 | 159034889 | 159034993 |
| 159034680 | 159034786 | 159034890 | 159034995 |
| 159034681 | 159034787 | 159034892 | 159034996 |
| 159034683 | 159034788 | 159034893 | 159034997 |
| 159034686 | 159034789 | 159034894 | 159034998 |
| 159034687 | 159034790 | 159034895 | 159035002 |
| 159034688 | 159034791 | 159034897 | 159035003 |
| 159034689 | 159034793 | 159034898 | 159035005 |
| 159034690 | 159034794 | 159034899 | 159035007 |
| 159034692 | 159034795 | 159034900 | 159035008 |
| 159034693 | 159034796 | 159034901 | 159035009 |
| 159034695 | 159034798 | 159034902 | 159035010 |
| 159034696 | 159034799 | 159034903 | 159035013 |

APPENDIX A-continued

GI NUMBERS OF 3,571 SEQUENCES IN THE
HEALTHY PREIMMUNE SET (HPS)

| | | | |
|---|---|---|---|
| 159035014 | 159035117 | 159035234 | 159035362 |
| 159035015 | 159035118 | 159035235 | 159035363 |
| 159035016 | 159035120 | 159035238 | 159035364 |
| 159035017 | 159035122 | 159035239 | 159035366 |
| 159035018 | 159035123 | 159035240 | 159035368 |
| 159035021 | 159035124 | 159035241 | 159035369 |
| 159035022 | 159035125 | 159035242 | 159035370 |
| 159035023 | 159035126 | 159035245 | 159035372 |
| 159035024 | 159035128 | 159035247 | 159035373 |
| 159035025 | 159035129 | 159035250 | 159035374 |
| 159035026 | 159035130 | 159035253 | 159035378 |
| 159035027 | 159035131 | 159035256 | 159035380 |
| 159035028 | 159035133 | 159035257 | 159035382 |
| 159035031 | 159035134 | 159035260 | 159035384 |
| 159035033 | 159035135 | 159035261 | 159035385 |
| 159035034 | 159035136 | 159035262 | 159035386 |
| 159035035 | 159035137 | 159035263 | 159035390 |
| 159035036 | 159035138 | 159035264 | 159035391 |
| 159035038 | 159035139 | 159035265 | 159035393 |
| 159035039 | 159035140 | 159035267 | 159035394 |
| 159035040 | 159035143 | 159035268 | 159035395 |
| 159035041 | 159035145 | 159035269 | 159035400 |
| 159035042 | 159035146 | 159035270 | 159035401 |
| 159035043 | 159035147 | 159035272 | 159035402 |
| 159035044 | 159035149 | 159035273 | 159035403 |
| 159035045 | 159035150 | 159035274 | 159035404 |
| 159035046 | 159035151 | 159035275 | 159035405 |
| 159035047 | 159035152 | 159035277 | 159035406 |
| 159035049 | 159035155 | 159035279 | 159035407 |
| 159035050 | 159035158 | 159035280 | 159035408 |
| 159035051 | 159035159 | 159035282 | 159035413 |
| 159035052 | 159035160 | 159035284 | 159035418 |
| 159035053 | 159035162 | 159035285 | 159035420 |
| 159035054 | 159035163 | 159035287 | 159035422 |
| 159035055 | 159035164 | 159035288 | 159035423 |
| 159035056 | 159035166 | 159035289 | 159035424 |
| 159035057 | 159035170 | 159035290 | 159035425 |
| 159035058 | 159035172 | 159035292 | 159035426 |
| 159035060 | 159035173 | 159035293 | 159035427 |
| 159035061 | 159035174 | 159035294 | 159035430 |
| 159035063 | 159035175 | 159035296 | 159035432 |
| 159035064 | 159035176 | 159035299 | 159035433 |
| 159035065 | 159035177 | 159035302 | 159035435 |
| 159035066 | 159035179 | 159035303 | 159035436 |
| 159035067 | 159035180 | 159035305 | 159035437 |
| 159035072 | 159035181 | 159035307 | 159035439 |
| 159035073 | 159035182 | 159035308 | 159035441 |
| 159035074 | 159035183 | 159035309 | 159035445 |
| 159035075 | 159035185 | 159035310 | 159035446 |
| 159035076 | 159035186 | 159035312 | 159035447 |
| 159035079 | 159035187 | 159035313 | 159035449 |
| 159035080 | 159035188 | 159035314 | 159035450 |
| 159035081 | 159035191 | 159035315 | 159035451 |
| 159035083 | 159035192 | 159035316 | 159035452 |
| 159035084 | 159035193 | 159035318 | 159035453 |
| 159035085 | 159035194 | 159035319 | 159035454 |
| 159035086 | 159035195 | 159035320 | 159035456 |
| 159035087 | 159035199 | 159035321 | 159035457 |
| 159035089 | 159035201 | 159035323 | 159035458 |
| 159035090 | 159035204 | 159035327 | 159035459 |
| 159035092 | 159035205 | 159035329 | 159035461 |
| 159035097 | 159035206 | 159035330 | 159035463 |
| 159035100 | 159035207 | 159035331 | 159035464 |
| 159035101 | 159035208 | 159035334 | 159035466 |
| 159035102 | 159035209 | 159035335 | 159035468 |
| 159035103 | 159035210 | 159035338 | 159035470 |
| 159035104 | 159035211 | 159035342 | 159035472 |
| 159035106 | 159035212 | 159035343 | 159035473 |
| 159035108 | 159035213 | 159035344 | 159035475 |
| 159035109 | 159035215 | 159035346 | 159035476 |
| 159035110 | 159035218 | 159035348 | 159035477 |
| 159035111 | 159035221 | 159035349 | 159035479 |
| 159035112 | 159035224 | 159035350 | 159035483 |
| 159035113 | 159035226 | 159035351 | 159035484 |
| 159035114 | 159035227 | 159035353 | 159035490 |
| 159035115 | 159035230 | 159035360 | 159035492 |
| 159035116 | 159035232 | 159035361 | 159035493 |

APPENDIX A-continued

GI NUMBERS OF 3,571 SEQUENCES IN THE
HEALTHY PREIMMUNE SET (HPS)

| | | | |
|---|---|---|---|
| 159035496 | 159035605 | 162950148 | 162950323 |
| 159035497 | 159035609 | 162950152 | 162950325 |
| 159035498 | 159035610 | 162950188 | 162950326 |
| 159035499 | 159035611 | 162950189 | 162950327 |
| 159035501 | 159035612 | 162950191 | 162950328 |
| 159035502 | 159035614 | 162950199 | 162950329 |
| 159035503 | 159035618 | 162950202 | 162950330 |
| 159035507 | 159035619 | 162950204 | 162950333 |
| 159035508 | 159035624 | 162950205 | 162950334 |
| 159035512 | 159035626 | 162950210 | 162950335 |
| 159035513 | 159035627 | 162950211 | 162950337 |
| 159035514 | 159035628 | 162950213 | 162950338 |
| 159035515 | 159035630 | 162950227 | 162950339 |
| 159035516 | 159035631 | 162950241 | 162950341 |
| 159035519 | 159035632 | 162950243 | 162950342 |
| 159035520 | 159035633 | 162950244 | 162950343 |
| 159035523 | 159035634 | 162950245 | 162950344 |
| 159035524 | 159035636 | 162950248 | 162950345 |
| 159035525 | 159035637 | 162950249 | 162950347 |
| 159035526 | 159035638 | 162950250 | 162950348 |
| 159035527 | 159035640 | 162950251 | 162950350 |
| 159035528 | 159035641 | 162950252 | 162950352 |
| 159035529 | 159035642 | 162950253 | 162950353 |
| 159035531 | 159035644 | 162950254 | 162950355 |
| 159035532 | 159035646 | 162950255 | 162950359 |
| 159035533 | 159035649 | 162950257 | 162950360 |
| 159035535 | 159035650 | 162950258 | 162950361 |
| 159035536 | 159035653 | 162950260 | 162950363 |
| 159035537 | 159035655 | 162950261 | 162950365 |
| 159035538 | 159035656 | 162950263 | 162950367 |
| 159035541 | 159035658 | 162950265 | 162950369 |
| 159035542 | 159035659 | 162950266 | 162950372 |
| 159035546 | 159035661 | 162950267 | 162950373 |
| 159035548 | 159035662 | 162950269 | 162950374 |
| 159035549 | 159035663 | 162950270 | 162950375 |
| 159035550 | 159035664 | 162950272 | 162950377 |
| 159035552 | 162950025 | 162950273 | 162950381 |
| 159035553 | 162950028 | 162950275 | 162950382 |
| 159035554 | 162950034 | 162950277 | 162950384 |
| 159035556 | 162950035 | 162950278 | 162950385 |
| 159035557 | 162950039 | 162950279 | 162950386 |
| 159035559 | 162950043 | 162950282 | 162950387 |
| 159035560 | 162950050 | 162950284 | 162950388 |
| 159035562 | 162950051 | 162950285 | 162950390 |
| 159035563 | 162950052 | 162950286 | 162950391 |
| 159035564 | 162950054 | 162950287 | 162950392 |
| 159035565 | 162950055 | 162950288 | 162950393 |
| 159035566 | 162950057 | 162950289 | 162950394 |
| 159035567 | 162950065 | 162950290 | 162950396 |
| 159035568 | 162950067 | 162950291 | 162950397 |
| 159035569 | 162950077 | 162950292 | 162950398 |
| 159035570 | 162950097 | 162950293 | 162950399 |
| 159035571 | 162950098 | 162950294 | 162950400 |
| 159035573 | 162950100 | 162950295 | 162950401 |
| 159035574 | 162950111 | 162950296 | 162950404 |
| 159035575 | 162950114 | 162950297 | 162950405 |
| 159035576 | 162950115 | 162950298 | 162950406 |
| 159035577 | 162950120 | 162950299 | 162950408 |
| 159035581 | 162950121 | 162950300 | 162950410 |
| 159035582 | 162950123 | 162950301 | 162950411 |
| 159035583 | 162950125 | 162950302 | 162950416 |
| 159035584 | 162950126 | 162950303 | 162950418 |
| 159035585 | 162950127 | 162950305 | 162950419 |
| 159035586 | 162950128 | 162950306 | 162950420 |
| 159035589 | 162950129 | 162950308 | 162950421 |
| 159035590 | 162950130 | 162950309 | 162950423 |
| 159035591 | 162950132 | 162950310 | 162950425 |
| 159035592 | 162950133 | 162950311 | 162950426 |
| 159035593 | 162950134 | 162950312 | 162950428 |
| 159035594 | 162950137 | 162950313 | 162950430 |
| 159035595 | 162950138 | 162950314 | 162950431 |
| 159035596 | 162950139 | 162950315 | 162950432 |
| 159035597 | 162950140 | 162950316 | 162950433 |
| 159035598 | 162950141 | 162950317 | 162950434 |
| 159035602 | 162950143 | 162950318 | 162950435 |
| 159035603 | 162950146 | 162950319 | 162950437 |
| 159035604 | 162950147 | 162950321 | 162950438 |

APPENDIX A-continued

GI NUMBERS OF 3,571 SEQUENCES IN THE HEALTHY PREIMMUNE SET (HPS)

| | | | | | |
|---|---|---|---|---|---|
| 162950439 | 162950566 | 162950674 | | 162950503 | 162950615 |
| 162950440 | 162950568 | 162950675 | | 162950504 | 162950617 |
| 162950441 | 162950570 | 162950676 | | 162950514 | 162950618 |
| 162950442 | 162950571 | 162950685 | | 162950515 | 162950619 |
| 162950444 | 162950572 | 162950686 | | 162950516 | 162950620 |
| 162950445 | 162950573 | 162950688 | | 162950517 | 162950621 |
| 162950446 | 162950574 | 162950689 | | 162950518 | 162950622 |
| 162950447 | 162950575 | 162950691 | | 162950519 | 162950626 |
| 162950449 | 162950577 | 162950692 | | 162950520 | 162950627 |
| 162950450 | 162950578 | 162950693 | | 162950522 | 162950628 |
| 162950451 | 162950579 | 162950694 | | 162950525 | 162950629 |
| 162950453 | 162950580 | 162950695 | | 162950526 | 162950631 |
| 162950454 | 162950581 | 162950696 | | 162950527 | 162950632 |
| 162950456 | 162950582 | 162950697 | | 162950528 | 162950633 |
| 162950461 | 162950583 | 162950698 | | 162950529 | 162950634 |
| 162950463 | 162950584 | 162950710 | | 162950530 | 162950635 |
| 162950464 | 162950585 | 162950714 | | 162950531 | 162950640 |
| 162950465 | 162950586 | 162950716 | | 162950532 | 162950641 |
| 162950466 | 162950587 | 162950720 | | 162950534 | 162950642 |
| 162950467 | 162950589 | 162950724 | | 162950535 | 162950644 |
| 162950469 | 162950590 | 162950725 | | 162950536 | 162950645 |
| 162950470 | 162950591 | 162950726 | | 162950537 | 162950646 |
| 162950471 | 162950592 | 162950728 | | 162950539 | 162950647 |
| 162950474 | 162950593 | 162950729 | | 162950540 | 162950649 |
| 162950476 | 162950594 | 194719560 | | 162950542 | 162950650 |
| 162950481 | 162950596 | 194719575 | | 162950543 | 162950651 |
| 162950483 | 162950597 | 218454113 | | 162950546 | 162950652 |
| 162950484 | 162950598 | 218454117 | | 162950547 | 162950654 |
| 162950485 | 162950599 | 219937557 | | 162950551 | 162950655 |
| 162950487 | 162950600 | | | 162950552 | 162950656 |
| 162950489 | 162950602 | | | 162950555 | 162950659 |
| 162950490 | 162950604 | | | 162950556 | 162950660 |
| 162950491 | 162950605 | | | 162950557 | 162950661 |
| 162950492 | 162950606 | | | 162950558 | 162950662 |
| 162950493 | 162950609 | | | 162950559 | 162950665 |
| 162950494 | 162950610 | | | 162950562 | 162950666 |
| 162950496 | 162950611 | | | 162950564 | 162950671 |
| 162950498 | 162950613 | | | 162950565 | 162950673 |
| 162950500 | 162950614 | | | | |

LENGTHY TABLES

The patent contains a lengthy table section. A copy of the table is available in electronic form from the USPTO web site (http://seqdata.uspto.gov/?pageRequest=docDetail&DocID=US10138478B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10138478B2). An electronic copy of the "Sequence Listing" will also be available from the USPTO upon request and payment of the fee set forth in 37 CFR 1.19(b)(3).

The invention claimed is:

1. A method of making a library comprising synthetic polynucleotides that encode an antibody heavy chain containing at least about $10^4$ unique antibody CDRH3 amino acid sequences, wherein each of the polynucleotides encoding the at least about $10^4$ unique antibody CDRH3 amino acid sequences has an antibody CDRH3 amino acid sequence represented by the following formula:

[TN1]-[DH]-[N2]-[H3-JH], the method comprising:
(a) providing a theoretical segment pool containing TN1, DH, N2, and H3-JH segments, wherein, the DH segments are provided according to the following steps:
  (i) obtaining a set of polynucleotide sequences of human IGHD genes and alleles;
  (ii) progressively deleting one or more nucleotide bases from the polynucleotide sequences of (i) on either or both of the 5' and 3' ends;
  (iii) systematically adding 0, 1 and/or 2 or more nucleotides to the 5' and/or 3' ends of the polynucleotide sequences from (ii);
  (iv) translating the polynucleotide sequences of (iii) and selecting unique amino acid sequences to thereby provide the DH theoretical segment pool;
(b) providing a reference set of preimmune CDRH3 sequences having sequence diversities and length diversities similar to naturally occurring human antibody sequences before these sequences have undergone negative selection and/or hypermutation;
(c) utilizing combinations of the TN1, DH, N2, and H3-JH segments contained in the theoretical segment pool of (a) to identify the closest match(es) to each CDRH3 sequence in the reference set of (b);
(d) selecting segments from the closest match(es) identified in step (c) for inclusion in a library comprising synthetic polynucleotides that encode an antibody heavy chain; and
(e) synthesizing the synthetic polynucleotides that encode an antibody heavy chain;
wherein the diversity of the polynucleotides encoding the at least about $10^4$ unique antibody CDRH3 amino acid sequences is created by polynucleotides having CDRH3 sequences that are different from the CDRH3 sequences of other polynucleotides; and
wherein the antibody heavy chain is a variable domain with framework (FRM) and complementary determining regions (CDR) comprising FRMH1-CDRH1-FRMH2-CDRH2-FRMH3-CDRH3-FRMH4.

2. The method of claim 1, wherein the segments selected for inclusion in the synthetic library are selected according to their segment usage weight in the reference set of CDRH3 sequences.

3. The method of claim 1, wherein the segments selected for inclusion in the synthetic library are selected according to one or more physicochemical properties.

4. The method of claim 1, further comprising selecting additional TN1 and N2 segments occurring in the reference set but not in the theoretical segment pool.

5. The method of claim 1, wherein stop codons are reduced or eliminated from the library.

6. The method of claim 1, wherein the unpaired Cys residues, N-linked glycosylation motifs, and deamidation motifs are reduced or eliminated in the translation products of the library.

7. The method of claim 1, wherein the theoretical segment pool contains TN1 segments corresponding to any of the TN1 polypeptides of Tables 10 and 18-26, or a polypeptide produced by translation of any of the TN1-encoding polynucleotides of Tables 25-26.

8. The method of claim 1, wherein the theoretical segment pool contains DH segments corresponding to any of the DH polypeptides of Tables 11, 17-25 and 28, or a polypeptide produced by translation of any of the DH-encoding polynucleotides of Tables 16, 25 and 27.

9. The method of claim 1, wherein the theoretical segment pool contains N2 segments corresponding to any of the N2 polypeptides of Tables 12, 18-25 and 30, or a polypeptide produced by translation of any of the N2-encoding polynucleotides of Tables 25 and 29.

10. The method of claim 1, wherein the theoretical segment pool contains H3-JH segments corresponding to any of the H3-JH polypeptides of Tables 13, 15, 18-25 and 32, or a polypeptide produced by translation of any of the H3-JH-encoding polynucleotides of Tables 14, 25 and 31.

11. The method of claim 1, wherein step (ii) includes progressively deleting nucleotide bases until 1, 2, 3, 4, 5, 6, 7, 8, 9, 10, 11, 12, 13, 14, or 15 remain.

12. The method of claim 3, wherein step (iii) includes:
A) addition of 0, 1 or 2 nucleotides to the 5' and/or 3'-ends of the polynucleotide sequences from (ii);
B) addition of 1 or 2 nucleotides at both the 5' and/or 3'-ends of the polynucleotide sequences from (ii);
C) addition of 1 nucleotide on the 5' end combined with 1 or 2 nucleotides on the 3' end of the polynucleotide sequences from (ii);
D) addition of 1 or 2 nucleotides to the 3' end only of the polynucleotide sequences from (ii); and/or
E) addition of 2 nucleotides on the 5' end combined with 1 or 2 nucleotides on the 3' end of the polynucleotide sequences from (ii).

13. The method of claim 1, wherein the unique sequences of (iv) do not have stop codons, unpaired Cys residues, deamidation motifs, or Asn in the last or next to last position that can lead to N-linked glycosylation motifs.

14. A method of making a library comprising synthetic polynucleotides that encode an antibody heavy chain containing at least about $10^4$ unique antibody CDRH3 amino acid sequences, wherein each of the polynucleotides encoding the at least about $10^4$ unique antibody CDRH3 amino acid sequences has an antibody CDRH3 amino acid sequence represented by the following formula:

[TN1]-[DH]-[N2]-[H3-JH], the method comprising:
(a) providing a theoretical segment pool containing TN1, DH, N2, and H3-JH segments, wherein the DH segments are provided according to the following steps:
  (i) obtaining a set of polynucleotide sequences of human IGHD genes and alleles;
  (ii) translating the polynucleotide sequences of (i), wherein translation of a partial codon containing two untranslated bases is completed to produce a full codon if the two bases encode a single amino acid regardless of the third position;
  (iii) progressively deleting amino acid sequences of (ii) at their N- and/or C-termini until at least two amino acids remain; and
  (iv) collecting unique sequences from (iii) that contain 2 or more amino acids to thereby provide the DH theoretical segment pool;

(b) providing a reference set of preimmune CDRH3 sequences having sequence diversities and length diversities similar to naturally occurring human antibody sequences before these sequences have undergone negative selection and/or hypermutation;
(c) utilizing combinations of the TN1, DH, N2, and H3-JH segments contained in the theoretical segment pool of (a) to identify the closest match(es) to each CDRH3 sequence in the reference set of (b);
(d) selecting segments from the closest match(es) identified in step (c) for inclusion in a library comprising synthetic polynucleotides that encode an antibody heavy chain; and
(e) synthesizing the synthetic polynucleotides that encode an antibody heavy chain;

wherein the diversity of the polynucleotides encoding the at least about $10^4$ unique antibody CDRH3 amino acid sequences is created by polynucleotides having CDRH3 sequences that are different from the CDRH3 sequences of other polynucleotides; and wherein the antibody heavy chain is a variable domain with framework (FRM) and complementary determining regions (CDR) comprising FRMH1-CDRH1-FRMH2-CDRH2-FRMH3-CDRH3-FRMH4.

15. The method of claim 14, wherein the unique sequences of (iv) do not have a stop codon, unpaired Cys residue, N-linked glycosylation motifs, or deamidation motifs.

16. The method of claim 14, wherein the theoretical segment pool contains DH segments corresponding to any of the DH polypeptides of Tables 11, 17-25 and 28, or a polypeptide produced by translation of any of the DH-encoding polynucleotides of Tables 16, 25 and 27.

17. A method of making a library comprising synthetic polynucleotides that encode an antibody heavy chain containing at least about $10^4$ unique antibody CDRH3 amino acid sequences, wherein each of the polynucleotides encoding the at least about $10^4$ unique antibody CDRH3 amino acid sequences has an antibody CDRH3 amino acid sequence represented by the following formula:

[TN1]-[DH]-[N2]-[H3-JH], the method comprising:
(a) providing a theoretical segment pool containing TN1, DH, N2, and H3-JH segments, wherein DH is a polypeptide corresponding to any of the DH polypeptides of Tables 11, 17-25 and 28, or a polypeptide produced by translation of any of the DH-encoding polynucleotides of Tables 16, 25 and 27;
(b) providing a reference set of preimmune CDRH3 sequences having sequence diversities and length diversities similar to naturally occurring human antibody sequences before these sequences have undergone negative selection and/or hypermutation;
(c) utilizing combinations of the TN1, DH, N2, and H3-JH segments contained in the theoretical segment pool of (a) to identify the closest match(es) to each CDRH3 sequence in the reference set of (b);
(d) selecting segments from the closest match(es) identified in step (c) for inclusion in a library comprising synthetic polynucleotides that encode an antibody heavy chain; and
(e) synthesizing the synthetic polynucleotides that encode an antibody heavy chain;

wherein the diversity of the polynucleotides encoding the at least about $10^4$ unique antibody CDRH3 amino acid sequences is created by polynucleotides having CDRH3 sequences that are different from the CDRH3 sequences of other polynucleotides; and wherein the antibody heavy chain is a variable domain with framework (FRM) and complementary determining regions (CDR) comprising FRMH1-CDRH1-FRMH2-CDRH2-FRMH3-CDRH3-FRMH4.

* * * * *

UNITED STATES PATENT AND TRADEMARK OFFICE
CERTIFICATE OF CORRECTION

| | |
|---|---|
| PATENT NO. | : 10,138,478 B2 |
| APPLICATION NO. | : 15/151626 |
| DATED | : November 27, 2018 |
| INVENTOR(S) | : Maximiliano Vasquez, Arvind Sivasubramanian and Michael Feldhaus |

It is certified that error appears in the above-identified patent and that said Letters Patent is hereby corrected as shown below:

In the Claims

Column 94, Claim 12, Line 24, delete "The method of claim 3" and insert --The method of claim 1--.

Signed and Sealed this
Nineteenth Day of February, 2019

Andrei Iancu
*Director of the United States Patent and Trademark Office*